United States Patent [19]

Krapcho et al.

[11] Patent Number: 5,596,097
[45] Date of Patent: Jan. 21, 1997

[54] HETERO-ANNULATED INDAZOLES

[75] Inventors: A. Paul Krapcho, Shelburne, Vt.; Ernesto Menta, Milan, Italy; Ambrogio Oliva, Varese, Italy; Silvano Spinelli, Monza, Italy

[73] Assignees: The University of Vermont, Burlington, Vt.; Boehringer Mannheim Italia, S.p.A., Monza, Italy

[21] Appl. No.: 207,130

[22] Filed: Mar. 8, 1994

[51] Int. Cl.⁶ ..................... A61K 31/47; C07D 471/06
[52] U.S. Cl. ............................................. 544/125; 546/64
[58] Field of Search ................... 544/125; 546/64; 514/287, 232.8

*Primary Examiner*—David B. Springer
*Attorney, Agent, or Firm*—Nikaido, Marmelstein, Murray & Oram, LLP

[57] ABSTRACT

This invention is directed to heteroannulated indazoles namely to 2,5-disubstituted quinolino-, isoquinolino-, phthalazino-, and quinoxalino- annulated indazole-6(2H)-ones and related mono N-oxides.

These compounds have been shown to have antitumor activity.

6 Claims, No Drawings

HETERO-ANNULATED INDAZOLES

BACKGROUND OF THE INVENTION

1. Field of the Invention

This invention is directed to hetero-annulated indazoles namely to 2,5-disubstituted quinolino-, isoquinolino-, phthalazino-, and quinoxalino- annulated indazole-6(2H)-ones and related mono N-oxides.

These compounds have been shown to have antitumor activity.

2. Background

Certain 1,4-bis[(aminoalkyl)amino]anthracene-9,10-diones have been reported which show antitumor activity in clinical trials. Of particular interest has been ametantrone, 1,4-bis{[2-(2-hydroxyethylamino)ethyl]}{anthracene-9,10-dione and mitoxantrone, 5,8-dihydroxy-1,4-bis{[2-(2-hydroxyethylamino)ethyl]aminoanthracene-9,10-dione [Zee-Cheng et al., *J. Med. Chem.* 21, 291–4 (1978); Cheng et al., "Progress in Medicinal Chemistry", Ellis, G.P. and West, G.B., eds.; Elsevier: Amsterdam, 1983, vol 20, pp. 83 and references cited therein]. Mitoxantrone is a broad spectrum oncolytic agent, whose activity is similar to that of the anthracycline antibiotic doxorubicin. Clinical trials have demonstrated that mitoxantrone has particularly promising activity in the treatment of advanced breast cancer, acute leukemia and lymphoma [Legha, *Drugs of Today* 20,629 (1984)]. Although animal studies have demonstrated a diminished cardiotoxicity in comparison to doxorubicin, some clinical cardiotoxicity has been observed also with mitoxantrone, mostly in patients previously treated with doxorubicin (R. Stuart Harris et al., *Lancet,* 219, (1984) and references cited therein).

Ametantrone has been reported to be, in animals, about 10-fold less potent and cardiotoxic than mitoxantrone. Because a delayed toxicity is observed only with mitoxantrone after administration of the two drugs by the i.p. route to non-tumor bearing rats at equieffective antitumor dosages, it is suggested that the presence of the 5,8-dihydroxy substitution in mitoxantrone might be implicated in the delayed deaths [Corbett et al., *Cancer Chemother, Pharmacol.,* 6, 161 (1981) ].

In addition, both mitoxantrone and ametantrone have a remarkable myelodepressive toxicity and both compounds show cross-resistance to cell hystotypes developing resistance against doxorubicin mediated by overexpression of glycoprotein P. Such a resistance, which is named multidrug resistance, involves a number of antitumor antibiotics, among which amsacrine and podophyllotoxinic derivatives, and it is one of the main reasons for therapeutical failures in the treatment of solid tumors with said antibiotics.

In an attempt to overcome the above mentioned drawbacks some chromophore modified anthracenediones have been prepared. For example, E.P. Patent Application 103, 381 discloses 2-aminoalkyl-5-aminoalkylamino substituted anthra[1,9-cd]pyrazol-6(2H)-ones (anthrapyrazoles) which are claimed to have antitumor activity. The antitumor activity of said compounds in a number of preclinical models have been reported by H. D. Hollis Showalter et al. (J. Med. Chem., 30, 121–131, (1987)). However anthrapyrazoles are not devoid of toxic side effects, with severe leukopenia (W.H.O. grade 3 and 4) and neutropenia (W.H.O. grade 4) being dose limiting in phase I and phase II clinical trials with the anthrapyrazole CI-941 (I.E. Smith et al., J. Clin. Oncol. 9, 2141–2147, (1991)). Moreover a marked nephrotoxicity is associated with CI-941 treatmnent in the rat (D. Campling and M. E. C. Robbins, Nephrotoxicity, Peter H. Dekker Bach editor, pag 345–352, (1991), New York); see Chemical Abstract 116:294 n, (1992) and these authors suggest that renal injury may be a clinical problem with anthrapyrazole therapy. In addition recent reports [Drugs of the Future, 17, 725, (1992); Judson, I.R. et al., Proc. Amer. Assoc. Cancer Res., 32, abstr 1059, (1991)]indicate that the anthrapyrazole CI 941 induces irreversible cardiotoxicity in humans, although no symptons of cardiac failure or acute cardiac events have been reported.

Therefore the search for newer active analogues is still highly desiderable.

We have now discovered that the introduction of one or two nitrogen atoms in the positions 7, 8, 9 or 10 of the above mentioned anthra[1,9-cd]pyrazol-6(2H)-ones provides 2,5-disubstituted quinolino-, isoquinolino-, phthalazino-, and quinoxalino-annulated indazole-6(2H)-ones and the related mono N-oxides, which are endowed with marked antitumor activity.

BRIEF SUMMARY OF THE INVENTION

The compounds of the invention have the formula (I)

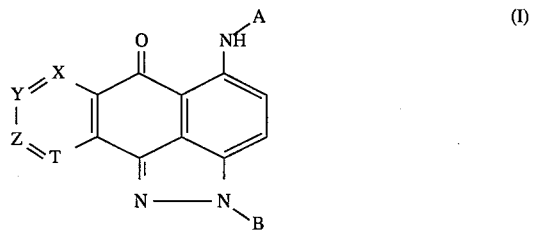

at least one of X,Y,Z and T is nitrogen (=N—) or N-oxide [=N(O)—] functionality and the others are selected from the group consisting of =CH—, =C(—O—P)—or =N—, with the following provisios:

not more than one of X, Y, Z and T can be =C(—O—P)—or =N(O)—;

not more than two of X, Y, Z, and T can be =N—;

X and T can not be =N(O)—;

Y and Z can not be =C(—O—P)—;

X and Z can not be simultaneously =N—;

Y and T can not be simultaneously =N—;

P is selected from the group consisting of hydrogen, methyl, benzyl, 4-methoxybenzyl; A and B are the same or different and are selected from the group of $C_1$–$C_{10}$ alkyl; $C_2$–$C_{10}$ alkyl having one or two substituents selected from the group consisting of $OR_1$ and —$NR_2R_3$; $C_2$–$C_{10}$ alkyl interrupted by one or two oxygen atoms or by one —$NR_4$— group, and said $C_2$–$C_{10}$ alkyl is optionally substituted by one or two hydroxy (OH) or —$NR_2R_3$ groups;

$R_1$ is selected from the group consisting of hydrogen, $C_1$–$C_6$ alkyl, —$S(O_2)R_5$, $C_2$–$C_6$ alkyl optionally substituted by —$NR_2R_3$;

$R_2$ and $R_3$ may be the same or different and are selected from the group consisting of hydrogen, $C_1$–$C_{10}$ alkyl, $C_2$–$C_{10}$ substituted with one or two hydroxy (OH) groups, or $R_2$ and $R_3$ taken together with the nitrogen atom to which they are bound form a 5- or 6-member aromatic or non-aromatic heterocyclic ring which optionally contains another heteroatom such as sulfur, oxygen or nitrogen;

$R_4$ is selected from the group consisting of hydrogen, $C_1$–$C_{10}$ alkyl, $C_2$–$C_{10}$ hydroxyalkyl, $C_2$–$C_{10}$ alkyl substituted with —$NR_2R_3$;

$R_5$ is selected from the group consisting of $C_1$–$C_{10}$ alkyl, phenyl, phenylalkyl, as free bases and their salts with pharmaceutically acceptable acids.

The present invention also concerns the tautomeric forms, the single enantiomers and diastereoisomers of the compounds of formula (I), as well as mixtures thereof.

The present invention also concerns the non-toxic salts of the compounds of formula (I) with acids acceptable for pharmaceutical and veterinary use such as those obtained by addition of inorganic acids like hydrochloric, hydrobromic, sulfuric, phosphoric, pyrophosphoric acid and/or of organic acids such as acetic, propionic, citric, benzoic, lactic, maleic, fumaric, succinic, tartaric, glutamic, aspartic, gluconic, ascorbic acids and the like.

DETAILED DESCRIPTION OF THE INVENTION

In compounds (I) the term "phenyl" means phenyl rings which can optionally contain substituents such as ($C_1$–$C_4$)alkyl groups, $CF_3$, halogen atoms, nitro, amino, acetylamino, formylamino, dimethylamino, diethylamino, hydroxy, methoxy and ethoxy groups.

Preferred examples of $C_1$–$C_{10}$ alkyl groups are methyl, ethyl, n-propyl, sec-propyl, n-butyl, sec-butyl, tert-butyl, n-pentyl, n-hexyl.

Preferred examples of phenylalkylis 4-methylphenyl. When in compounds of formula (I) A and B are a $C_2$–$C_{10}$ alkyl interrupted by one or two oxygen atoms or by one —$NR_4$—group and optionally substituted by one or two hydroxy or —$NR_2R_3$ groups, at least two carbon atoms are preferably interposed between said oxygen atoms and/or the —N—$R_4$—and —$NR_2R_3$ groups.

When in compounds of formula (I) the —$NR_2R_3$ substituent is a 5–6 member aromatic or not aromatic heterocyclic ring which may contain another heteroatom such as sulfur, oxygen and nitrogen, preferred examples of said heterocyclic rings are 1-imidazolyl, 4-hydroxy-1-imidazolyl, 2-imino-1(3H)-imidazolyl, 1-pyrrolyl, 1-tetrahydropyrrolyl, 1-pyrazolyl, 4-morpholinyl, 1-piperidinyl, 1-piperazinyl, 1-(4-methyl)-piperazinyl, 1-(4-benzyl)-piperazinyl.

Preferred compounds of the invention are those of formula (I) where X, Y, Z and T have the following values of Table 1.

TABLE 1

| X | Y | Z | T | COMPOUNDS OF FORMULA I | NAME OF THE HETEROCYCLIC SYSTEM |
|---|---|---|---|---|---|
| CH | CH | CH | N | | quino[8,7,6-cd]indazole-(2H)-one |
| N | CH | CH | CH | | quino[5,6,7-cd]indazole-6(2H)-one |
| CH | CH | N | CH | | isoquino[8,7,6-cd]indazole-6(2H)-one |

TABLE 1-continued

| X | Y | Z | T | COMPOUNDS OF FORMULA I | NAME OF THE HETEROCYCLIC SYSTEM |
|---|---|---|---|---|---|
| CH | CH | N(O) | CH | | isoquino[8,7,6-cd]indazole-6(2H)-one-9-oxide |
| CH | N | CH | CH | | isoquino[5,6,7-cd]indazole-6(2H)-one |
| CH | N(O) | CH | CH | | isoquino[5,6,7-cd]indazole-6(2H)-one-8-oxide |
| C(OH) | CH | N | CH | | 7-hydroxyisoquino[8,7,6-cd]indazole-6(2H)-one |
| CH | N | CH | C(OH) | | 10-hydroxyisoquino[5,6,7-cd]indazole-6(2H)-one |

TABLE 1-continued

| X | Y | Z | T | COMPOUNDS OF FORMULA I | NAME OF THE HETEROCYCLIC SYSTEM |
|---|---|---|---|---|---|
| N | CH | CH | N | 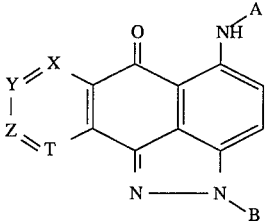 | quinoxalino[5,6,7-cd]indazole-6(2H)-one |
| CH | N | N | CH | 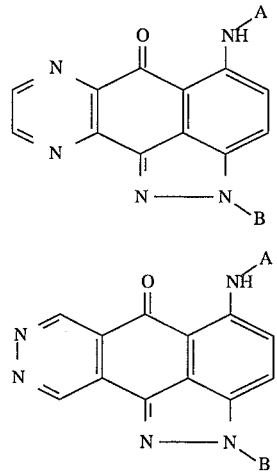 | phthalazino[5,6,7-cd]indazole-6(2H)-one |

Most preferred compounds are those according to formula (I) wherein X, Y, Z, and T are as above defined and A and B are independently selected from the group consisting of:

residue of formula —(CH$_2$)$_p$—NH$_2$ wherein p is the integer 2 or 3;

residue of formula —(CH$_2$)$_p$—NR$_2$R$_3$ wherein p is as above defined and both R$_2$ and R$_3$ are methyl or ethyl or 2-hydroxyethyl;

residue of formula —(CH$_2$)$_p$—NR$_2$R$_3$ wherein p is as above defined and R$_2$ is hydrogen and R$_3$ is methyl;

residue of formula —(CH$_2$)$_p$—NR$_2$R$_3$ wherein p is as above defined and NR$_2$R$_3$ is 4-morpholinyl, 1-piperidinyl, 1-piperazinyl, 1-imidazolyl;

residue of formula —(CH$_2$)$_p$—OH wherein p is as above defined residue of formula —(CH$_2$)$_p$—NH—(CH$_2$)$_q$—OH wherein p and q are independently an integer selected from group consisting of 2 or 3;

Specific examples of the preferred compounds of this invention are reported in table 2 and have the following chemical names:

(1) 2-[2-[(2-hydroxyethyl)amino]ethyl]-5-[[2-[(2-hydroxyethyl)amino]ethyl]amino]isoquino[8,7,6-cd]indazole-6(2H)-one;
(2) 2-[2-[(2-hydroxyethyl)amino]ethyl]-5-[(3-aminopropyl)amino]isoquino[8,7,6-cd]indazole-6(2H)-one;
(3) 2-[2-[(2-hydroxyethyl)amino]ethyl]-5-[(2-amino-ethyl)amino]isoquino[8,7,6-cd]indazole-6(2H)-one;
(4) 2-[2-[(2-hydroxyethyl)amino]ethyl]-5-[[2-methylamino)ethyl]amino]isoquino[8,7,6-cd]indazole-6(2H)-one;
(5) 2-[2-[(2-hydroxyethyl)amino]ethyl]-5-[[2-(dimethylamino)ethyl]amino]isoquino[8,7,6-cd]indazole-6(2H)-one;
(6) 2-[2-[(2-hydroxyethyl)amino]ethyl]-5-[[2-[(2-hydroxyethyl)amino]ethyl]amino]isoquino[5,6,7-cd)indazole-6(2H)-one;
(7) 2-[2-[(2-hydroxyethyl)amino]ethyl]-5-[(3-aminopropyl)amino]isoquino[5,6,7-cd]indazole-6(2H)-one;
(8) 2-[2-[(2-hydroxyethyl)amino]ethyl]-5-[(2-aminoethyl)amino]isoquino[5,6,7-cd]indazole-6(2H)-one;
(9) 2-[2-[(2-hydroxyethyl)amino]ethyl]-5-[[2-(methylamino)ethyl]amino]isoquino[5,6,7-cd]indazole-6(2H)-one;
(10) 2-[2-[(2-hydroxyethyl)amino]ethyl]-5-[[2-dimethylamino)ethyl]amino]isoquino[5,6,7-cd]indazole-6(2H)-one;
(11) 5-[[2-[(2-hydroxyethyl)amino]ethyl]amino]-2-[2-(dimethylamino)ethyl]isoquino[8,7,6-cd]indazole-6(2H)-one;
(12) 5-[(3-aminopropyl)amino]-2-[2-(dimethylamino)ethyl]isoquino[8,7,6-cd]indazole-6(2H)-one;
(13) 5-[(2-aminoethyl)amino]-2-[2-[2-(dimethylamino)ethyl]isoquino[8,7,6-cd]indazole-6(2H)-one;
(14) 5-[[2-(methylamino)ethyl]amino]-2-[2-dimethylamino)ethyl]isoquino[8,7,6-cd]indazole-6(2H)-one;
(15) 5-[[2-(dimethylamino)ethyl]amino]-2-[2-(dimethylamino)ethyl]isoquino[8,7,6-cd]indazole-6(2H)-one;
(16) 5-[[2-[(2-hydroxyethyl)amino[ethyl[amino]-2-[2-(dimethylamino)ethyl]isoquino[5,6,7-cd]indazole-6(2H)-one;
(17) 5-[(3-aminopropyl)amino]-2-[2-(dimethylamnio)ethyl]isoquino[5,6,7-cd]indazole-6(2H)-one;
(18) 5-[(2-aminoethyl)amino]-[2-(dimethylamino)ethyl]isoquino[5,6,7-cd]indazole-6(2H)-one;
(19) 5-[[2-(methylamino)ethyl]amino]-2-[2-(dimethylamino)ethyl]isoquino[5,6,7-cd]indazole-6(2H)-one;

(20) 5-[[2-(dimethylamino)ethyl]amino]-2-[2-(dimethylamino)ethyl]isoquino[5,6,7-cd]indazole-6(2H)-one;
(21) 2-[2-aminoethyl]-5-[[2[(2-hydroxyethyl)amino]ethyl]amino]isoquino[8,7,6-cd]indazole-6(2H)-one;
(22) 2-[2-aminoethyl]-5-[(3-aminopropyl)amino]isoquino[8,7,6-cd]indazole-6(2H-one;
(23) 2-[2-aminoethyl]-5-[(2-aminoethyl)amino[isoquino[8,7,6-cd]indazole-6(2H)-one;
(24) 2-[2-aminoethyl]-5-[[2-(methylamino)ethyl]amino]isoquino[8,7,6-cd]indazole-6(2H)-one;
(25) 2-[2-aminoethyl]-5-[[2-(dimethylamino)ethyl]amino]isoquino[8,7,6-cd]indazole-6(2H)-one;
(26) 2-[3-aminopropyl]-5-[[2-[(2-hydroxyethyl)amino]ethyl]amino]isoquino[8,7,6-cd]indazole-6(2H)-one;
(27) 2-[3-aminopropyl]-5-[(3-aminopropyl)amino]isoquino[8,7,6-cd]indazole-6(2H-one;
(28) 2-[3-aminopropyl]-5[(2-amino)ethyl)amino]isoquino[8,7,6-cd]indazole-6(2H)-one;
(29) 2-[3-aminopropyl]-5-[[2-(methylamino)ethyl]amino]isoquino]8,7,6-cd]indazole-6(2H)-one;
(30) 2-[3-aminopropyl]-5-[[2-(dimethylamino)ethyl]amino]isoquino[8,7,6-cd]indazole-6(2H)-one;
(31) 5-[[2-[(2-hydroxyethyl)amino]ethyl]amino]-2-[3-aminopropyl]isoquino[5,6,7-cd]indazole-6(2H)-one;
(32) 5-[[2-[(2-hydroxyethyl)amino]ethyl]amino]-2-[2-aminoethyl]isoquino[5,6,7-cd)indazole-6(2H)-one;
(33) 2-[(2-methylamino)ethyl]-5-[[2-[(2-hydroxyethyl)amino]ethyl]amino]isoquino[8,7,6-cd]indazole-6(2H)-one;
(34) 2-[(2-methylamino)ethyl]-5-[(3-aminopropyl)amino]isoquino[8,7,6-cd]indazole-6(2H)-one;
(35) 2-[(2-methylamino)ethyl]-5-[(2-aminoethyl)amino]isoquino[8,7,6-cd]indazole-6(2H)-one;
(36) 2-[(2-methylamino)ethyl]-5-[[2-(methylamino)ethyl]amino]isoquino[8,7,6-cd]indazole-6(2H)-one;
(37) 2-[(2-methylamino)ethyl]-5-[[2-(dimethylamino)ethyl]amino]isoquino[8,7,6-cd]indazole-6(2H)-one;
(38) 2-[(2-methylamino)ethyl]-5-[[2-[(2-hydroxyethyl)amino]ethyl]amino]isoquino[5,6,7-cd]indazole-6(2H)-one;
(39) 2-[(2-methylamino)ethyl]-5-[(3-aminopropyl)amino]isoquino[5,6,7-cd]indazole-6(2H)-one;
(40) 2-[(2-amino)ethyl]-5-[(2-aminoethyl)amino]isoquino[5,6,7-cd)indazole-6(2H)-one;
(41) 2-[(2-methylamino)ethyl]-5-[[2-(methylamino)ethyl]amino]isoquino]5,6,7-cd]indazole-6(2H)-one;
(42) 2-[(2-methylamino)ethyl]-5-[[2-(dimethylamino)ethyl]amino]isoquino[5,6,7-cd]indazole-6(2H)-one;
(43) 2-methyl-5-[[2-(dimethylamino)ethyl]amino]isoquino[8,7,6-cd]indazole-6(2H)-one;
(44) 2-methyl-5-[[2-(dimethylamino)ethyl]amino]isoquino[5,6,7-cd]indazole-6(2H)-one;
(45) 2-[2-(dimethylamino)ethyl]-5-[[2-(diethylamino)ethyl]amino]isoquino[8,7,6-cd]indazole-6(2H)-one;
(46) 2-[2-(dimethylamino)ethyl]-5-[[2-(4'-morpholinyl)ethyl]amino]isoquino[8,7,6-cd]indazole-6(2H)-one;
(47) 2-[2-(dimethylamino)ethyl]-5-[[3-(dimethylamino)propyl]amino]isoquino[8,7,6-cd]indazole-6(2H)-one;
(48) 2-[2-(dimethylamino)ethyl]-5-[[2-(1'-piperidinyl)ethyl]amino]isoquino[8,7,6-cd]indazole-6(2H)-one;
(49) 2-[2-(dimethylamino)ethyl]-5-[[2-(1'-piperazinyl)ethyl]amino]isoquino[8,7,6-cd]indazole -6(2H)-one;
(50) 2-[2-(dimethylamino)ethyl]-5-[[2-(1'-imidazolyl)ethyl]amino]isoquino[8,7,6-cd]indazole-6(2H)-one;
(51) 2-[2-(dimethylamino)ethyl]-5-[2-(hydroxyethyl)amino]isoquino[8,7,6-cd]indazole-6(2H)-one;
(52) 2-[2-(dimethylamino)ethyl]-5-[[2-[N-bis(2-hydroxyethyl)amino]ethyl]amino]isoquino[8,7,6-cd]indazole-6(2H)-one;
(53) 2-[2-aminoethyl]-5-[[2-(diethylamino)ethyl]amino]isoquino[8,7,6-cd]indazole-6(2H)-one;
(54) 2-[2-aminoethyl]-5-[[2-(4'-morpholinyl)ethyl]amino]isoquino[8,7,6-cd[indazole-6(2H)-one;
(55) 2-[2-aminoethyl]-5-[[2-[N-bis(2-hydroxyethyl)amino]ethyl]amino]isoquino[8,7,6-cd]indazole-6(2H)-one;
(56) 2-[2-hydroxyethyl]-5-[(2-aminoethyl)amino]isoquino[8,7,6-cd]indazole-6(2H)-one;
(57) 2-[2-hydroxyethyl]-5-[[2-(dimethylamino)ethyl]amino]isoquino[8,7,6-cd]indazole-6(2H)-one;
(58) 2-methyl-5-[[2-(dimethylamino)ethyl]amino]-7-hydroxyisoquino[8,7,6-cd]indazole-6(2H)-one;
(59) 2-[2-(dimethylamino)ethyl]-5-[[2-(dimethylamino)ethyl]amino]-7-hydroxyisoquino[8,7,6-cd]indazole-6(2H)-one;
(60) 2-methyl-5-[[2-(dimethylamino)ethyl]amino]-10-hydroxyisoquino[5,6,7-cd]indazole-6(2H)-one;
(61) 2-[2-aminoethyl]-5-[3-dimethylamino)propyl]amino]-10-hydroxyisoquino[5,6,7-cd]indazole-6(2H)-one
(62) 2-[2-(dimethylamino)ethyl]-5-[[2-(dimethylamino)ethyl]amino]-10-hydroxyisoquino[5,6,7-cd]indazole-6(2H)-one;
(63) 2-[2-aminoethyl]-5-[(2-aminoethyl)amino]-10-hydroxyisoquino[5,6,7-cd]indazole-6(2H)-one;
(64) 2-[2-aminoethyl]-5-[[2-(dimethylamino)ethyl]amino]-10-hydroxyisoquino[5,6,7-cd]indazole-6(2H)-one;
(65) 2-methyl-5-[[2-(dimethylamino)ethyl]amino]isoquino[8,7,6-cd]indazole-6(2H)-one-9-oxide;
(66) 2-[2-aminoethyl]-5-[3-dimethylamino)propyl]amino]isoquino[8,7,6-cd]indazole-6(2H)-one-9-oxide
(67) 2-[2-(dimethylamino)ethyl]-5-[[2-(dimethylamino)ethyl]amino]isoquino[8,7,6-cd]indazole-6(2H)-one-9-oxide;
(68) 2-[2-aminoethyl]-5-[(2-aminoethyl)amino]isoquino[8,7,6-cd]indazole-6(2H)-one-9-oxide;
(69) 2-[2-aminoethyl]-5-[[2-(dimethylamino)ethyl]amino]isoquino[8,7,6-cd]indazole-6(2H)-one-9-oxide;
(70) 2-methyl-5-[[2-(dimethylamino)ethyl]amino]isoquino[5,6,7-cd]indazole-6(2H)-one-8-oxide;
(71) 2-[2-aminoethyl]-5-[[2-(dimethylamino)ethyl]amino]isoquino[5,6,7-cd]indazole-6(2H)-one-8-oxide;
(72) 2-[2-(dimethylamino)ethyl]-5-[[2-(dimethylamino)ethyl]amino]isoquino[5,6,7-cd]indazole-6(2H)-one-8-oxide;
(73) 2-methyl-5-[[2-(dimethylamino)ethyl]amino]quino[8,7,6-cd]indazole-6(2H)-one;
(74) 2-[2-aminoethyl]-5-[[2-(dimethylamino)ethyl]amino]quino[8,7,6-cd]indazole-6(2H)-one;
(75) 2-[2-(dimethylamino)ethyl]-5-[[2-(dimethylamino)ethyl]amino]quino[8,7,6-cd]indazole-6(2H)-one;
(76) 2-[2-aminoethyl]-5-[(2-aminoethyl)amino]quino[8,7,6-cd]indazole-6(2H)-one;
(77) 2-[2-aminoethyl]-5-[[2-(methylamino)ethyl]amino]quino[8,7,6-cd]indazole-6(2H)-one;
(78) 2-methyl-5-[[2-(dimethylamino)ethyl]amino]quino[5,6,7-cd]indazole-6(2H)-one;
(79) 2-[3-(dimethylamino)propyl]-5-[[2-(dimethylamino)ethyl]amino]isoquino[8,7,6-cd]indazole-6(2H)-one;
(80) 2-[2-(dimethylamino)ethyl]-5-[[2-(dimethylamino)ethyl]amino]quino[5,7,6-cd]indazole-6(2-H)-one;
(81) 2-[2-aminoethyl]-5-[(2-aminoethyl)amino]quino[5,6,7-cd]indazole-6(2H)-one;
(82) 2-[2-aminoethyl]-5-[[2-(dimethylamino)ethyl]amino]quino[5,6,7-cd]indazole-6(2H)-one;
(83) 2-methyl-5-[[2-(dimethylamino)ethyl]amino]quinoxalino[5,6,7-cd]indazole-6(2H)-one;
(84) 2-[2-aminoethyl]-5-[[2-(dimethylamino)ethyl]amino]quinoxalino[5,6,7-cd]indazole-6(2H)-one;

(85) 2-[2-(dimethylamino)ethyl]-5-[[2-(dimethylamino)ethyl]amino]quinoxalino[5,6,7-cd]indazole-6(2H)-one;
(86) 2-[2-aminoethyl]-5-[(2-aminoethyl)amino]quinoxalino[5,6,7-cd]indazole-6(2H)-one;
(87) 2-[2-aminoethyl]-5-[[2-(methylamino)ethyl]amino]quinoxalino[5,6,7-cd]indazole-6(2H)-one;
(88) 2-methyl-5-[[2-(dimethylamino)ethyl]amino]phthalazino[5,6,7-cd]indazole-6(2H)-one;
(89) 2-[2-aminoethyl]-5-[[2-(dimethylamino)ethyl]amino]phthalazino[5,6,7-cd]indazole-6(2H)-one;
(90) 2-[2-(dimethylamino)ethyl]-5-[[2-(dimethylamino)ethyl]amino]phthalazino[5,6,7-cd]indazole-6(2H)-one;
(91) 2-[2-aminoethyl]-5-[(2-aminoethyl)amino]phthalazino [5,6,7-cd]indazole-6(2H)-one;
(92) 2-[2-bis[N-(2-hydroxyethyl)amino]ethyl-5-[[2-(dimethylamino)ethyl]amino]isoquino[8,7,6-cd]indazole-6(2H)-one;

TABLE 2

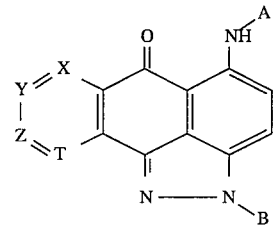

(I)

| No. | T | Y | Z | X | A | B |
|---|---|---|---|---|---|---|
| 1 | CH | C | N | CH | $CH_2CH_2NHCH_2CH_2OH$ | $CH_2CH_2NHCH_2CH_2OH$ |
| 2 | CH | C | N | CH | $CH_2CH_2CH_2NH_2$ | $CH_2CH_2NHCH_2CH_2OH$ |
| 3 | CH | C | N | CH | $CH_2CH_2NH_2$ | $CH_2CH_2NHCH_2CH_2OH$ |
| 4 | CH | C | N | CH | $CH_2CH_2NHCH_3$ | $CH_2CH_2NHCH_2CH_2OH$ |
| 5 | CH | C | N | CH | $CH_2CH_2N(CH_3)_2$ | $CH_2CH_2NHCH_2CH_2OH$ |
| 6 | CH | N | C | CH | $CH_2CH_2NHCH_2CH_2OH$ | $CH_2CH_2NHCH_2CH_2OH$ |
| 7 | CH | N | C | CH | $CH_2CH_2CH_2NH_2$ | $CH_2CH_2NHCH_2CH_2OH$ |
| 8 | CH | N | C | CH | $CH_2CH_2NH_2$ | $CH_2CH_2NHCH_2CH_2OH$ |
| 9 | CH | N | C | CH | $CH_2CH_2NHCH_3$ | $CH_2CH_2NHCH_2CH_2OH$ |
| 10 | CH | N | C | CH | $CH_2CH_2N(CH_3)2$ | $CH_2CH_2NHCH_2CH_2OH$ |
| 11 | CH | C | N | CH | $CH_2CH_2NHCH_2CH_2OH$ | $CH_2CH_2N(CH_3)_2$ |
| 12 | CH | C | N | CH | $CH_2CH_2CH_2NH_2$ | $CH_2CH_2N(CH_3)_2$ |
| 13 | CH | C | N | CH | $CH_2CH_2NH_2$ | $CH_2CH_2N(CH_3)_2$ |
| 14 | CH | C | N | CH | $CH_2CH_2NHCH_3$ | $CH_2CH_2N(CH_3)_2$ |
| 15 | CH | C | N | CH | $CH_2CH_2N(CH_3)_2$ | $CH_2CH_2N(CH_3)_2$ |
| 16 | CH | N | C | CH | $CH_2CH_2NHCH_2CH_2OH$ | $CH_2CH_2N(CH_3)_2$ |
| 17 | CH | N | C | CH | $CH_2CH_2CH_2NH_2$ | $CH_2CH_2N(CH_3)_2$ |
| 18 | CH | N | C | CH | $CH_2CH_2NH_2$ | $CH_2CH_2N(CH_3)_2$ |
| 19 | CH | N | C | CH | $CH_2CH_2NHCH_3$ | $CH_2CH_2N(CH_3)_2$ |
| 20 | CH | N | C | CH | $CH_2CH_2N(CH_3)_2$ | $CH_2CH_2N(CH_3)_2$ |
| 21 | CH | C | N | CH | $CH_2CH_2NHCH_2CH_2OH$ | $CH_2CH_2NH_2$ |
| 22 | CH | C | N | CH | $CH_2CH_2CH_2NH_2$ | $CH_2CH_2NH_2$ |
| 23 | CH | C | N | CH | $CH_2CH_2NH_2$ | $CH_2CH_2NH_2$ |
| 24 | CH | C | N | CH | $CH_2CH_2NHCH_3$ | $CH_2CH_2NH_2$ |
| 25 | CH | C | N | CH | $CH_2CH_2N(CH_3)_2$ | $CH_2CH_2NH_2$ |
| 26 | CH | C | N | CH | $CH_2CH_2NHCH_2CH_2OH$ | $CH_2CH_2CH_2NH_2$ |
| 27 | CH | C | N | CH | $CH_2CH_2NH_2$ | $CH_2CH_2CH_2NH_2$ |
| 29 | CH | C | N | CH | $CH_2CH_2NHCH_3$ | $CH_2CH_2CH_2NH_2$ |
| 30 | CH | C | N | CH | $CH_2CH_2N(CH_3)_2$ | $CH_2CH_2CH_2NH_2$ |
| 31 | CH | N | C | CH | $CH_2CH_2NHCH_2CH_2OH$ | $CH_2CH_2CH_2NH_2$ |
| 32 | CH | N | C | CH | $CH_2CH_2NHCH_2CH_2OH$ | $CH_2CH_2NH_2$ |
| 33 | CH | C | N | CH | $CH_2CH_2NHCH_2CH_2OH$ | $CH_2CH_2NHCH_3$ |
| 34 | CH | C | N | CH | $CH_2CH_2CH_2NH_2$ | $CH_2CH_2NHCH_3$ |
| 35 | CH | C | N | CH | $CH_2CH_2NH_2$ | $CH_2CH_2NHCH_3$ |
| 36 | CH | C | N | CH | $CH_2CH_2NHCH_3$ | $CH_2CH_2NHCH_3$ |
| 37 | CH | C | N | CH | $CH_2CH_2N(CH_3)_2$ | $CH_2CH_2NHCH_3$ |
| 38 | CH | N | C | CH | $CH_2CH_2NHCH_2CH_2OH$ | $CH_2CH_2NHCH_3$ |
| 39 | CH | N | C | CH | $CH_2CH_2CH_2NH_2$ | $CH_2CH_2NHCH_3$ |
| 40 | CH | N | C | CH | $CH_2CH_2NH_2$ | $CH_2CH_2NH_2$ |
| 41 | CH | N | C | CH | $CH_2CH_2NHCH_3$ | $CH_2CH_2NHCH_3$ |
| 42 | CH | N | C | CH | $CH_2CH_2N(CH_3)_2$ | $CH_2CH_2NHCH_3$ |
| 43 | CH | C | N | CH | $CH_2CH_2N(CH_3)_2$ | $CH_3$ |
| 44 | CH | N | C | CH | $CH_2CH_2N(CH_3)_2$ | $CH_3$ |
| 45 | CH | CH | N | CH | $CH_2CH_2N(CH_2CH_3)_2$ | $CH_2CH_2N(CH_3)_2$ |
| 46 | CH | CH | N | CH | $CH_2CH_2N(CH_2CH_2)_2O$ | $CH_2CH_2N(CH_3)_2$ |
| 47 | CH | CH | N | CH | $CH_2CH_2CH_2N(CH_3)_2$ | $CH_2CH_2N(CH_3)_2$ |
| 48 | CH | CH | N | CH | $CH_2CH_2N(CH_2CH_2)_2CH_2$ | $CH_2CH_2N(CH_3)_2$ |
| 49 | CH | CH | N | CH | $CH_2CH_2N(CH_2CH_2)_2NH$ | $CH_2CH_2N(CH_3)_2$ |
| 50 | CH | CH | N | CH | $CH_2CH_2$-(1-Imidazolyl) | $CH_2CH_2N(CH_3)_2$ |
| 51 | CH | CH | N | CH | $CH_2CH_2OH$ | $CH_2CH_2N(CH_3)_2$ |
| 52 | CH | CH | N | CH | $CH_2CH_2N(CH_2CH_2OH)_2$ | $CH_2CH_2N(CH_3)_2$ |

TABLE 2-continued

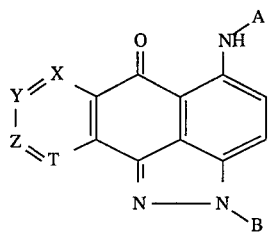

(I)

| No. | T | Y | Z | X | A | B |
|---|---|---|---|---|---|---|
| 53 | CH | CH | N | CH | CH$_2$CH$_2$N(CH$_2$CH$_3$)$_2$ | CH$_2$CH$_2$NH$_2$ |
| 54 | CH | CH | N | CH | CH$_2$CH$_2$N(CH$_2$CH$_2$)$_2$O | CH$_2$CH$_2$NH$_2$ |
| 55 | CH | CH | N | CH | CH$_2$CH$_2$N(CH$_2$CH$_2$OH)$_2$ | CH$_2$CH$_2$NH$_2$ |
| 56 | CH | CH | N | CH | CH$_2$CH$_2$NH$_2$ | CH$_2$CH$_2$OH |
| 57 | CH | CH | N | CH | CH$_2$CH$_2$N(CH$_3$)$_2$ | CH$_2$CH$_2$OH |
| 58 | CH | CH | N | C(OH) | CH$_2$CH$_2$N(CH$_3$)$_2$ | CH$_3$ |
| 59 | CH | CH | N | C(OH) | CH$_2$CH$_2$N(CH$_3$)$_2$ | CH$_2$CH$_2$N(CH$_3$)$_2$ |
| 60 | C(OH) | N | CH | CH | CH$_2$CH$_2$N(CH$_3$)$_2$ | CH$_3$ |
| 61 | C(OH) | N | CH | CH | CH$_2$CH$_2$CH$_2$N(CH$_3$)$_2$ | CH$_2$CH$_2$NH$_2$ |
| 62 | C(OH) | N | CH | CH | CH$_2$CH$_2$N(CH$_3$)$_2$ | CH$_2$CH$_2$N(CH$_3$)$_2$ |
| 63 | C(OH) | N | CH | CH | CH$_2$CH$_2$NH$_2$ | CH$_2$CH$_2$NH$_2$ |
| 64 | C(OH) | N | CH | CH | CH$_2$CH$_2$N(CH$_3$)$_2$ | CH$_2$CH$_2$NH$_2$ |
| 65 | CH | CH | N(O) | CH | CH$_2$CH$_2$N(CH$_3$)$_2$ | CH$_3$ |
| 66 | CH | CH | N(O) | CH | CH$_2$CH$_2$CH$_2$N(CH$_3$)$_2$ | CH$_2$CH$_2$NH$_2$ |
| 67 | CH | CH | N(O) | CH | CH$_2$CH$_2$N(CH$_3$)$_2$ | CH$_2$CH$_2$N(CH$_3$)$_2$ |
| 68 | CH | CH | N(O) | CH | CH$_2$CH$_2$NH$_2$ | CH$_2$CH$_2$NH$_2$ |
| 69 | CH | CH | N(O) | CH | CH$_2$CH$_2$N(CH$_3$)$_2$ | CH$_2$CH$_2$NH$_2$ |
| 70 | CH | N(O) | CH | CH | CH$_2$CH$_2$N(CH$_3$)$_2$ | CH$_3$ |
| 71 | CH | N(O) | CH | CH | CH$_2$CH$_2$N(CH$_3$)$_2$ | CH$_2$CH$_2$NH$_2$ |
| 72 | CH | N(O) | CH | CH | CH$_2$CH$_2$N(CH$_3$)$_2$ | CH$_2$CH$_2$N(CH$_3$)$_2$ |
| 73 | N | CH | CH | CH | CH$_2$CH$_2$N(CH$_3$)$_2$ | CH$_3$ |
| 74 | N | CH | CH | CH | CH$_2$CH$_2$N(CH$_3$)$_2$ | CH$_2$CH$_2$NH$_2$ |
| 75 | N | CH | CH | CH | CH$_2$CH$_2$N(CH$_3$)$_2$ | CH$_2$CH$_2$N(CH$_3$)$_2$ |
| 76 | N | CH | CH | CH | CH$_2$CH$_2$NH$_2$ | CH$_2$CH$_2$NH$_2$ |
| 77 | N | CH | CH | CH | CH$_2$CH$_2$NHCH$_3$ | CH$_2$CH$_2$NH$_2$ |
| 78 | CH | CH | CH | N | CH$_2$CH$_2$N(CH$_3$)$_2$ | CH$_3$ |
| 79 | CH | CH | N | CH | CH$_2$CH$_2$NH$_2$ | CH$_2$CH$_2$CH$_2$N(CH$_3$)$_2$ |
| 80 | CH | CH | CH | N | CH$_2$CH$_2$N(CH$_3$)$_2$ | CH$_2$CH$_2$N(CH$_3$)$_2$ |
| 81 | CH | CH | CH | N | CH$_2$CH$_2$NH$_2$ | CH$_2$CH$_2$NH$_2$ |
| 82 | CH | CH | CH | N | CH$_2$CH$_2$N(CH$_3$)$_2$ | CH$_2$CH$_2$NH$_2$ |
| 83 | N | CH | CH | N | CH$_2$CH$_2$N(CH$_3$)$_2$ | CH$_3$ |
| 84 | N | CH | CH | N | CH$_2$CH$_2$N(CH$_3$)$_2$ | CH$_2$CH$_2$NH$_2$ |
| 85 | N | CH | CH | N | CH$_2$CH$_2$N(CH$_3$)$_2$ | CH$_2$CH$_2$N(CH$_3$)$_2$ |
| 86 | N | CH | CH | N | CH$_2$CH$_2$NH$_2$ | CH$_2$CH$_2$NH$_2$ |
| 87 | N | CH | CH | N | CH$_2$CH$_2$NHCH$_3$ | CH$_2$CH$_2$NH$_2$ |
| 88 | CH | N | N | CH | CH$_2$CH$_2$N(CH$_3$)$_2$ | CH$_3$ |
| 89 | CH | N | N | CH | CH$_2$CH$_2$N(CH$_3$)$_2$ | CH$_2$CH$_2$NH$_2$ |
| 90 | CH | N | N | CH | CH$_2$CH$_2$N(CH$_3$)$_2$ | CH$_2$CH$_2$N(CH$_3$)$_2$ |
| 91 | CH | N | N | CH | CH$_2$CH$_2$NH$_2$ | CH$_2$CH$_2$NH$_2$ |
| 92 | CH | CH | N | CH | CH$_2$CH$_2$N(CH$_3$)$_2$ | CH$_2$CH$_2$N(CH$_2$CH$_2$OH)$_2$ |

In a first embodiment of this invention, the compounds of formula (I) can be prepared by the process depicted in scheme 1 and involving the reaction (reaction a) of a compound of formula (III):

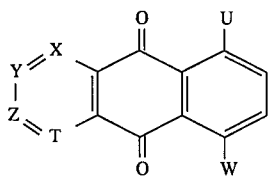

(III)

where X,Y,Z, and T are as above defined, U is selected from the group consisting of F, Cl, OTs (OTs being the p-toluenesulfonyloxy group), W is F or Cl with the proviso that U and W can not simultaneously be Cl, with a hydrazine of formula (IV):

H$_2$N—NH—B'  (IV)

where B' has the same meanings as B is defined in formula (I), or B' is a group that can be converted into B by removal of protective groups for the primary or secondary amines and hydroxy groups optionally present in B", to give a compound of formula (II):

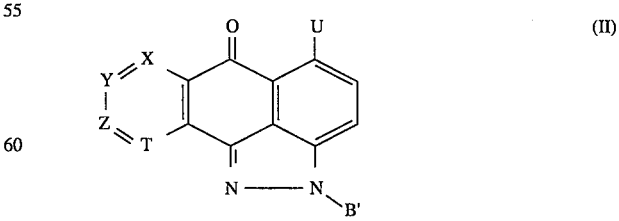

(II)

which then is reacted (reaction b) with a compound of formula (V)

H$_2$N—A'  (V)

where A' has the same meanings as A is defined in formula (I), or A' is a group that can be converted into A by removal of protective groups for the primary or secondary amines or hydroxy groups optionally present in A', to give the compounds of formula (I'):

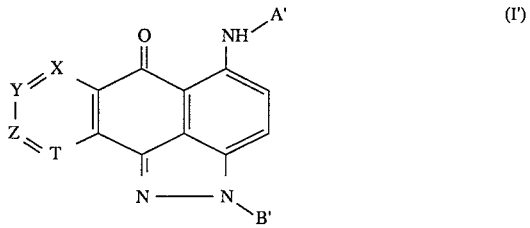

(I')

When A' and/or B' are different from A and/or B, compounds of formula (I') are converted to compounds of formula I by removal of the protective groups for the primary and or secondary amines or hydroxy groups optionally present in A' and/or B'.

Compounds of formula (I) wherein one of X, Y, Z, and T is C(O—P) and wherein P is methyl, benzyl or 4-methoxybenzyl can be converted in compounds of formula (I) wherein P is hydrogen by removal of the methyl, benzyl or 4-methoxybenzyl groups.

In a further embodiment of this invention, the compounds of formula (I) can be obtained by the multistep process depicted in scheme 2 involving the reaction (reaction c) of a compound of formula (III'):

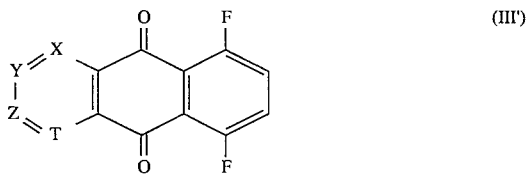

(III')

where X, Y, Z, and T are as above defined, with an amine of formula (V), to give a compound of formula (VI)

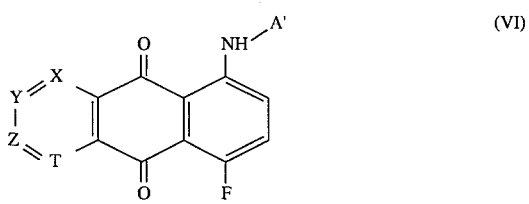

(VI)

which is then reacted (reaction d) with a hydrazine of formula (IV) to give the compounds of formula (I') which are then optionally deprotected as above to give the compounds of formula (I).

Protective groups for the primary and/or secondary amines optionally present in A' and/or B' which can advantageously be used for the preparation of compounds of formula (I) are represented by ($C_1$-$C_3$)acyl-derivatives (preferably acetyl-derivatives), ($C_1$-$C_4$) alkoxycarbonyl-derivatives (preferably tert-butoxycarbonyl-derivatives) and by ($C_7$-$C_{10}$)aralkyloxycarbonyl-derivatives (preferably benzyloxycarbonyl-derivatives).

In a preferred embodiment of this invention compounds of formula I where X is as above defined, one of Z or Y are N or N(O) and the other is CH, and T is CH, are prepared by reaction of a compound of formula III":

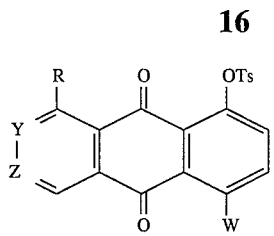

(III")

where R is H or O—P and P and W are as above defined, with a hydrazine of formula (IV) to give a compound of formula (II').

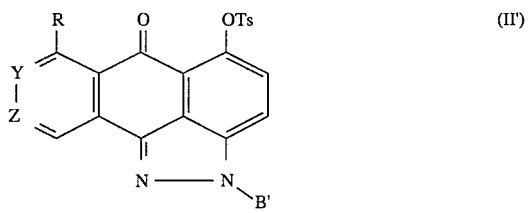

(II')

Compounds of formula (II') are then reacted with a compound of formula (V) to give a compound of formula (I'), which step is followed by removal of the protective groups for the primary and secondary amines or hydroxy groups optionally present in A' and/or B', to give a compound of formula (I) where X is as above defined, one of Z or Y are N or N(O) and the other is CH, and T is CH.

In another preferred embodiment of this invention compounds of formula (I) wherein X and Z are CH, Y is N or N(O) and T is as above defined are preferably prepared by reaction of a compound of formula (III'''):

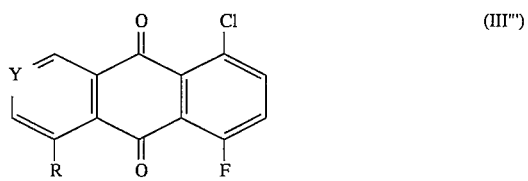

(III''')

where R is H or O—P and P is as above defined, with a hydrazine of formula (IV) to give a compound of formula (II"):

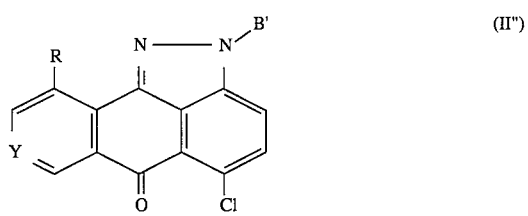

(II")

Compounds of formula (II") are then reacted with a compound of formula (V) to give a compound of formula (I'), which step is followed by removal of the protective groups for the primary and secondary amines or hydroxy groups optionally present in A' and/or B', to give a compound of formula (I) wherein X and Z are CH, Y is N or N(O) and T is as above defined.

The reaction of compounds (III) with the hydrazines (IV) can be performed by heating compounds (III) with a stoichiometric amount of hydrazines (IV) or an excess of hydrazines (IV). The reaction is usually performed in an inert solvent such as methylene chloride, chloroform, 1,1,1-trichloroethane, dimethoxyethane, tetrahydrofuran, dimethylsulfoxide, dimethylformamide, pyridine, picoline, and mixtures thereof, or if it is desired, using compound (IV) itself as the solvent, optionally in the presence of an inorganic base such as an alkaline or alkaline-earth carbonate or hydrogen carbonate or an organic base such as a trialkylamine, at a temperature from −20° C. to the reflux temperature of the solvent.

Preferably the reaction is carried out in a solvent such as pyridine, tetrahydrofuran, dimethylsulfoxide, or N,N,N',N'-tetramethylethylenediamine, using from 2 to 10 equivalents of compound (IV) for 1 equivalent of compound (III), and working at a temperature ranging from 5° C. to 50° C.

When, in a particular embodiment of this invention, a compound of formula (III") is reacted with a hydrazine of formula (IV), the reaction is preferably performed with a molar ratio between compounds (III") and (IV) of 1:1.05 to 1:1.25 and by using tetrahydrofuran as solvent at a temperature ranging from room temperature to 50° C.

The reaction of the compounds of formula (II) with the compounds of formula (V) can be performed by heating compounds (II) with a stoichiometric amount of amine (V) or an excess of amine (V). The reaction is usually performed in an inert solvent such as methylene chloride, chloroform, 1,1,1-trichloroethane, dimethoxyethane, tetrahydrofuran, dimethylsulfoxide, dimethylformamide, pyridine, picoline, and mixtures thereof, or, if it is desired, using compound (V) itself as the solvent, optionally in the presence of an inorganic base such as an alkaline or alkaline-earth carbonate or hydrogen carbonate or an organic base such as a trialkylamine, at a temperature from 0° C. to the reflux temperature of the solvent.

Preferably the reaction is carried out in a solvent such as pyridine, chloroform, or dimethylsulfoxide, using from 2 to 10 equivalents of compound (V) for 1 equivalent of compound (II), and working at a temperature ranging from room temperature to 100° C.

The reaction of a compound of formula (III') with an amine of formula (V), to give a compound of formula (VI) is performed using a stoichiometric amount or a slight molar excess of the compound of formula (V). The reaction is usually performed in an inert solvent such as methylene chloride, chloform, 1,1,1-trichloroethane, dimethoxyethane, tetrahydrofuran, dimethylsulfoxide, dimethylformamide, pyridine, picoline and mixture thereof, optionally in the presence of an inorganic base such as an alkaline or alkaline-hearth carbonate or hydrogen carbonate or an organic base such as a trialkylamine, at a temperature from 0° C. to the reflux temperature of the solvent.

Preferably the reaction is carried out in a solvent such as pyridine, chloroform, or dimethylsulfoxide at room temperature.

The reaction of compounds of formula (VI) with hydrazines (IV) is performed analogously to the reaction of compounds (III) with the same hydrazines (IV).

When, in the compounds of formula (I'), A' and/or B' are different from A and/or B, the removal of the protective group for the primary and/or secondary amino functions is carried out following the procedures well known to those skilled in the art. Useful teachings can be found in Green, T. W., Wuts, P.G.M., "Protective Groups in Organic Synthesis", second Edition, John Wiley & Sons, 1991.

For example, the removal of the N-(tert-butoxycarbonyl) protective group can be performed by treatment of a compound of formula (I') with an excess of anhydrous hydrochloric acid in a solvent such as a ($C_1$–$C_4$) alkanol, dichloromethane, chloroform, or mixtures thereof, at a temperature of 0° C. to the reflux temperature of the solvent and for a time ranging from several minutes to a few hours. Preferably the reaction is performed in ethanol or in chloroform using from 10 to 20 molar equivalents of anhydrous hydrochloric acid at a temperature of from 20° C. to 50° C., and is generally complete in four hours.

The removal of the benzyl and p-methoxybenzyl protective groups for the phenolic functionality optionally present in compounds (I') is generally performed by catalytic hydrogenation (benzyl protective group) or treatment with organic or inorganic acids (p-methoxybenzyl protective group).

Compounds of formula (III) where one of X, Y, Z, and T are the N-oxide functionality N(O) are prepared by oxidation of a compound of formula (VII):

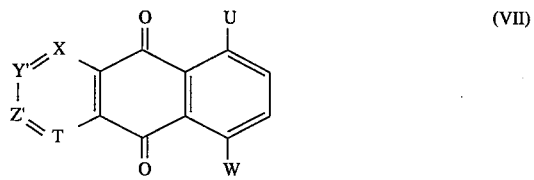

where Y' and Z' have the same meanings as Y and Z in formula (I) with the exception of N(O), with oxidizing agents such as peracids, peroxides and salts thereof.

The oxidation of compounds (VII) is generally carried out using a stoichiometric amount or a slight excess of an oxidizing agent in a solvent such as chloroform, methylene chloride, 1,2-dichloroethane, acetic acid, optionally in the presence of an alkaline or alkaline-earth metal carbonate or bicarbonate, at a temperature from 0° C. to the reflux temperature of the solvent and for a time ranging from a few hours to some days, depending on the experimental conditions.

Examples of the oxidizing agents which can effectively be used to oxidize compounds of formula (VII) to the related N-oxides include hydrogen peroxide; peracids such as peracetic, trifluoroperacetic, perbenzoic, or m-chloroperbenzoic acids; monoperoxyphthalic acid or the magnesium salt thereof; persuccinic acid. The reaction is preferably effected using an organic peracid such as m-chloroperbenzoic acid in a solvent such as methylene chloride.

The compounds of formula (VII) where X, Y', Z' and T are as above defined and U and W are both fluorine, namely compounds of formula (VII'):

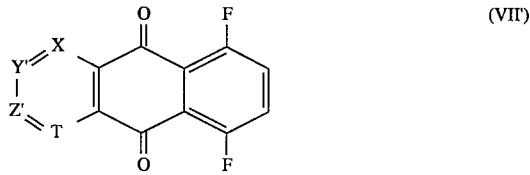

can be prepared by a multistep procedure, depicted in scheme 3, involving:

the Friedel and Craft acylation of 1,4-difluorobenzene with a compound of formula (VIII) (step e):

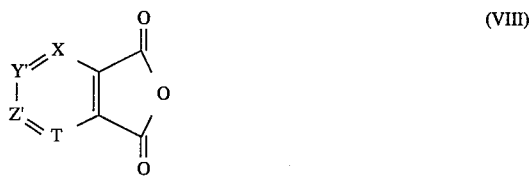

wherein X, Y', Z' and T are as above defined, in the presence of $AlCl_3$ (110° C., 22 h) which leads to the regioisomeric keto-acids (IXa) and (IXb); alternatively, the regioisomeric keto-acids (IXa) and (IXb) can be obtained by reaction of the compounds of formula (VIII) with 1-lithio-2,5-difluorobenzene (step F), prepared by reaction of 1,4-difluorobenzene with an alkyllithium reagent such as for example secbutyl lithium in THF at low temperature;

cyclization of the mixture of the regioisomeric keto-acids (IXa) and (IXb) with 20% oleum at 130°–140° C. (step g) to give the compound of formula (VII) wherein U and W are both fluorine (compounds (VII')), The compounds of formula (VII) where X is C(R), T is CH, Y',Z', W and R are as above defined, and U is OTs, namely compounds (VII"):

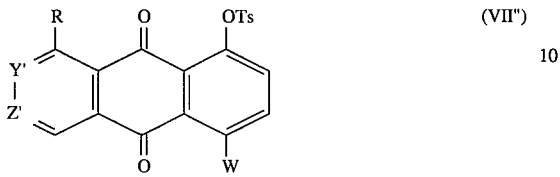

can be prepared by a multistep procedure, depicted in scheme 4, involving:

- reaction of the ketoacids (IXa) and (IXb) obtained according to scheme 3 and where X is C(R), T is CH, Y', Z', W and R are as above defined, namely compounds (IX'a) and (IX'b), with sodium methoxide in methanol (8.5 h, reflux) leading to the regioisomeric methoxy-substituted ketoacids (Xa) and (Xb) (step h); compounds (Xa) and (Xb) where R is hydrogen can be reacted as such in the following step; when R is different from hydrogen, compound (Xa) is purified by crystallization and reacted as pure regioisomer;
- reduction of compounds (Xa) (R different from hydrogen) with Zn/Cu couple in 75% aqueous formic acid (15' room temperature, then then 80° C., 2 h) leading to (XI) (step i); when R is hydrogen, the acids (XIa) and (XIb) can be separated by chromatography yielding the pure isolated regioisomers (XIa) and (XIb);
- cyclization of the appropriate acid (XI) by heating a suspension of the compound in polyphosphoric acid at 110°–120° C. for 2 h leading to the benzo[g]isoquinolines (XII) (step j);
- oxidation of the compounds (XII) to the corresponding dione (XIII) by cerium ammonium nitrate in a mixture of acetonitrile and water (60° C., 2 h) (step k);
- removal of the methoxy group of the dione (XIII) by aluminum chloride in methylene chloride (room temperature 2 h, then reflux temperature 1.5 h), leading to compounds (XIV) which correspond to a mixture of 9-fluoro-6-hydroxy- and 9-chloro-6-hydroxy-5,10-diones (XIV) due to partial substitution of the leaving fluoride by means of AlCl₃ (step l); and
- the final functionalization of the free hydroxy group of (XIV) by means of p-toluenesulfonyl chloride in pyridine at room temperature, leads to the desired compounds (VII) wherein Z=OTs [compounds (VII")] (step m).

In a preferred embodiment of this invention, the preparation of intermediates (XIII) is carried out by a multistep procedure, depicted in scheme 5, involving the following reactions:

- cyclization of the mixture of the regioisomeric keto-acids (IXa) and (IXb) with 20% oleum at 130°–140° C. to give the 6,9-difluorobenzo[g]isoquinolines (XV) (step n);
- reaction of (XV) with one equivalent of sodium methylate in a solvent such as methanol to give a mixture of intermediates (XIII) which is separated into the single pure compounds (XIIIa) and (XIIIb) by recrystallization from a solvent and/or column chromatography (step o).

The compounds of formula (VII) where X, Y', Z' and T are as above defined, one of U or W is fluorine and the other is chlorine, namely compounds (VII'''):

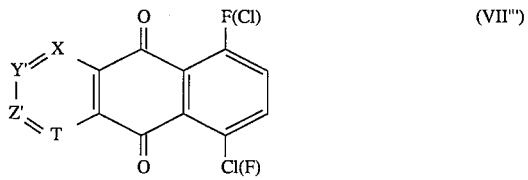

can be prepared by a multistep procedure depicted in scheme 6, involving:

- the Friedel and Craft acylation (step p) of 1-chloro-4-fluorobenzene with a compound of formula (VIII) in the presence of AlCl₃ (110° C., 22 h) which leads to the regioisomeric keto-acids (XVIa) and (XVIb) which can be used as such for the next step or they can be separated into the pure regioisomers by fractional crystallization or sublimation; alternatively, the regioisomeric keto-acids (XVIa) and (XVIb) can be obtained (step q) by reaction of the compounds of formula (VIII) with 1-lithio-2-fluoro-5-chlorobenzene, prepared by reaction of 1-chloro-4-fluorobenzene with an alkyl-lithium reagent such as for example sec-butyl lithium in THF at low temperature;
- cyclization of the mixture of the regioisomeric keto-acids (XVIa) and (XVIb) with 20% oleum at 130°–140° C. to give the compound of formula (VII) wherein one of U or W is fluorine and the other is chlorine [compounds (VII''')] (step r).

The preferred process of this invention which provides the compounds of formula (VII) where X is C(R), Y' and T are CH, Z' is N, U is fluorine and W is chlorine, namely the 9-chloro-6-fluorobenzo[g]isoquinoline-5,10-diones of formula (VII''''):

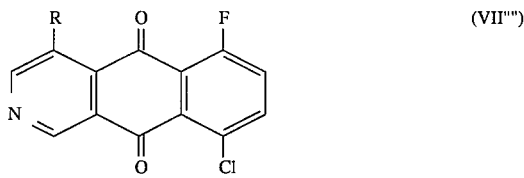

is depicted in scheme 7 and involves the following reactions:

- lithiation (step s) of 1-chloro-4-fluorobenzene with an alkyllithium reagent such as sec-butyllithium in THF at −75° C. to give 1-lithio-5-chloro-2-fluorobenzene;
- acylation (step t) of 1-lithio-5-chloro-2-fluorobenzene, generated in situ according to the above step, with pyridine-3,4-dicarboxylic anhydrides (VIII; X=C(R); Y', T=CH; Z'=N) to give the mixture of keto-acids (XVIIa) and (XVIIb) which can be separated into the single pure compounds by recrystallization from a solvent or by sublimation;
- reduction (step u) of the pure keto-acid (XVIIa) with Zn/Cu couple or Zn powder in 75% aqueous formic acid (15' at room temperature, then 80° C., 2 hrs) leading to (XVIII);
- oxidative cyclization (step v) of (XVIII) with fuming sulfuric acid (20–30% SO₃, 10', 130° C.) to give the 9-chloro-6-fluorobenzo[g] isoquinoline-5,10-diones of formula (VII''').

The intermediates of formula (VII) where X is C(O—P), Z' is N, Y' and T are CH, U is fluorine and W is chlorine, namely 4-substituted-6-fluoro-9-chlorobenzo[g]isoquinoline-5,10-diones of formula (VII''''):

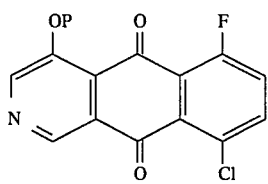 (VII'''')

are preferably prepared by the multistep process, depicted in scheme 8, involving the following reactions:

Friedel and Crafts acylation of 1-cloro-4-fluorobenzene with maleic anhydride (step x) to give (E)-4-(2'-fluoro-5'-chlorophenyl)-4-oxo-butenoic acid (XIX);

esterification of compound (XIX) with methanol (step y) to give the intermediate methyl-(E)-4-(2'-fluoro-5'-chlorophenyl)-4-oxo-butenoate (XX);

Diels-Alder reaction of intermediate (XX) with the known 5-ethoxyoxazole-2-carboxylic acid (XXI) (step w) to give methyl 5-hydroxy-4-(2'-fluoro-5'-chlorobenzoyl)nicotinate (XXII);

saponification (step z) of the methylester of (XXII) to give 5-hydroxy-4-(2'-fluoro-5'-chlorobenzoyl)nicotinic acid (XXIII);

reduction (step aa) of the pure keto-acid (XXIII) with Zn/Cu couple or Zn powder in 75% aqueous formic acid leading to 5-hydroxy-4-(2'-fluoro-5'-chlorobenzyl)nicotinic acid (XXIV);

oxidative cyclization (step ab) of (XXIV) with fuming sulfuric acid to give the 4-hydroxy-9-chloro-6-fluorobenzo[g]isoquinoline-5,10-dione of formula (XXV);

protection of the 4-hydroxy group of compounds of formula (XXV) as the methyl, benzyl or, preferably, p-methoxybenzyl ether by reaction with diazomethane, phenyldiazomethane or O-(p-methoxybenzyl)-N,N'-diisopropylurea respectively (step ac) to give the compounds of formula (VII'''').

The compounds of formula VIII can be prepared by compounds of formula (XXIV):

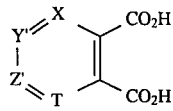 (XXVI)

wherein X, Y', Z', and T are as defined in formula (VIII), by reaction with an appropriate dehydrating agent such as carboxylic acid anhydrides (e.g. acetic or trifluoracetic anhydride), carbodiimides such as N,N'-dicyclohexylcarbodiimide, and the like.

Acetic anhydride at a temperature from 80° C. to the solvent's reflux temperature or N, N'-dicyclohexylcarbodiimide in an aprotic solvent are preferred reaction conditions.

Compounds XXIV are known or commercially available.

BIOLOGICAL ACTIVITY OF COMPOUNDS OF THE INVENTION

The evaluation of the biological activity for the compounds of this invention was performed in vitro and in vivo following the protocols developed by the U.S. National Cancer Institute.

The evaluation of the in vitro cytotoxic activity of the compounds of the invention was performed using a human colon adenocarcinoma cell line (LoVo) isolated from a metastatic nodule, and a subline expressing multidrug resistance. The subline is resistant to a number of antitumor agents, among which are doxorubicin, VP-16, and vincristine. This subline (named LoVo/DX) shows reduced accumulation of doxorubicin and overexpression of a protein (Grandi, M., Geroni, C., Giuliani, F. C., British J. Cancer, (1986), 54, 515). The compounds were tested according to the MTT assay (Mosman, T. "Rapid Colorimetric assay for cellular growth and survival: application to proliferation and cytotoxicity assay", J. Immunol. Methods, (1983), 65, 55–63; Green, L. M., "Rapid colorimetric assay for cell viability; application to the quantitation of cytotoxic and growth inhibitory lymphokines", J. Immunol. Methods, (1984), 70, 257–268) in comparison with mitoxantrone, and doxorubicin.

In general, representative compounds of this invention were more cytotoxic than doxorubicin and as cytotoxic as mitoxantrone in the LoVo cell line. When mitoxantrone was tested in the LoVo/DX cell line, a resistance index RI (defined a the ratio of the $IC_{50}$ for the resistant line cell to the $IC_{50}$ for the sensitive cell line) as high as 22.5 was found, showing that this subline does have an acquired resistance to mitoxantrone. On the other hand, some compounds of this invention, when tested in the same resistant subline, show no cross resistance with mitoxantrone as reported in Table 3. The in vitro evaluation of representative compounds of this invention suggests that representative compounds of this invention may be useful in order to overcome the multidrug resistance-mediated mechanism of tumor resistance.

Studies of the biological activity in vivo of representative compounds of the invention were performed using the P388 murine leukemia model. P388 murine leukemia cells were leukemia cells were intravenously (iv) injected in CD2Fl mice. Treatment was initiated approximately 24 hours after tumor transplantation and dosages of the drug were administered iv (P388 iv/iv) according to preestablished protocols, usually at 3-day (P388 iv/iv) intervals. The studies were done over a 60-day period and the date of death for each animal was recorded. The % T/C was determined using the mean survival time (MST) for each group according to the formula % T/C=[(MST treated)/(MST control)]×100

Representative compounds of this invention were able to increase the survival time of treated animals significantly more than mitoxantrone, leading to higher T/C % values at well tolerated dosages. Moreover, the above representative compounds of the invention showed antileukemic activity over a wide range of well tolerated dosages, and, in particular, were active at dosages which were lower than their maximum tolerated dose, providing indication for more favorable therapeutic index in comparison to mitoxantrone.

Since representative compounds of this invention show good results against this significative in vivo model of murine P388 leukemia, which is considered to be predictive of antitumor activity in humans, the compounds disclosed herein are expected to be operative against human leukemias and solid tumors sensitive to treatment with antitumor antibiotics.

The compounds of the present invention may therefore be used as active ingredients of therapeutic compositions to induce regression and/or palliation of cancers in mammals when administered in amounts ranging from about 1 mg to about 0.4 g per kilogram of body weight. A preferred dosage regimen would be from about 1 mg to about 50 mg per kilogram of body weight per day. Unit dosage may be employed so that from about 70 mg to about 3.5 g of the active compound for a subject of about 70 kg of body weight are administered in a 24-hour period. The dosage may be adjusted to be compatible to other treatment regimens, such as radiation therapy.

TABLE 3

| Antitumor activity of representative compounds of the invention | | | | P 388 i.v./i.v. + 1, 4, 7 | | |
|---|---|---|---|---|---|---|
| Structure | Comp. number (see tab. 2) | I.C.$_{50}$ ± S.D. (μg/mL) | | Dose (mg/Kg) | T/C % | Tox. |
| (structure) | 15 (a) | LoVo<br>LoVo/Dx<br>R.I. | 0.35 ± 0.17<br>1 ± 0.53<br>2.8 | 3<br>4<br>6<br>12 | 329, 338<br>381<br>212, 219<br>135 | 0/16<br>0/8<br>15/16<br>8/8 |
| (structure) | 13 (a) | LoVo<br>LoVo/Dx:<br>R.I. | 0.16 ± 0.09<br>4.3 ± 1.4<br>27 | 1.3<br>2<br>3<br>6<br>12 | 175<br>213<br>171, 238<br>124<br>100 | 0/8<br>0/8<br>8/16<br>8/8<br>8/8 |
| (structure) | 45 (a) | LoVo<br>LoVo/Dx<br>R.I. | 0.4<br>0.7<br>1.7 | 3<br>4<br>6 | 150<br>175<br>194 | 0/8<br>0/8<br>0/8 |
| (structure) | 46 (a) | LoVo<br>LoVo/Dx<br>R.I. | 1.9<br>2.7<br>1.4 | 6<br>12<br>24<br>36<br>54 | 150<br>188<br>256, 256<br>306<br>119 | 0/8<br>0/8<br>0/16<br>2/8<br>7/8 |
| (structure) | 25 (b) | LoVo<br>LoVo/Dx<br>R.I. | 0.3 ± 0.17<br>15.9 ± 8<br>53 | 3<br>4<br>6<br>9<br>12 | 141<br>169<br>182, 188<br>231<br>176 | 0/8<br>0/8<br>0/16<br>0/8<br>8/8 |

TABLE 3-continued

| Structure | Dose | Cell line | IC50 | Dose (mg/Kg) | T/C % | Tox. |
|---|---|---|---|---|---|---|
| 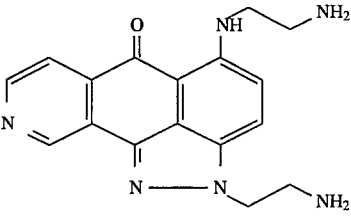 | 23 (b) | LoVo<br>LoVo/Dx<br>R.I. | 0.86 ± 0.06<br>15.4 ± 8.9<br>18 | 3<br>6<br>7.5<br>10<br>12 | 150<br>181, 181<br>194<br>231<br>181 | 0/8<br>0/16<br>0/8<br>8/8<br>8/8 |
| 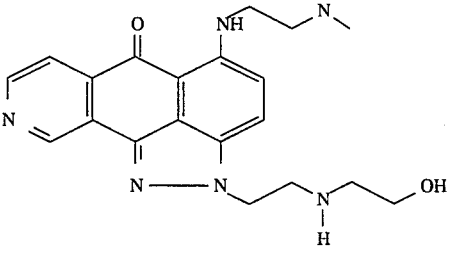 | 5 (a) | LoVo<br>LoVo/Dx<br>R.I. | 0.5<br>33.1<br>66.2 | 3<br>6<br>12 | 138<br>156<br>200 | 0/8<br>0/8<br>0/8 |
| 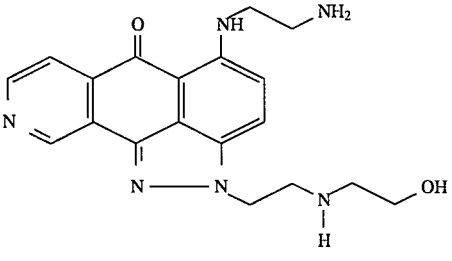 | 3 (b) | LoVo<br>LoVo/Dx<br>R.I. | 2.9<br>10<br>3.4 | 18<br>27 | 231<br>113 | 0/8<br>7/7 |
| 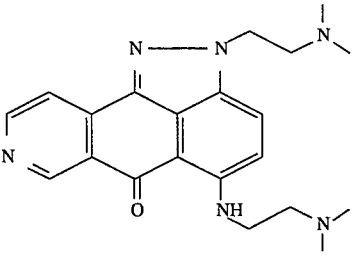 | 20 (a) | LoVo<br>LoVo/Dx<br>R.I. | 3.1 ± 1.6<br>6.2 ± 2.3<br>2 | 3<br>40 | 100<br>153 | 0/8<br>0/8 |
| 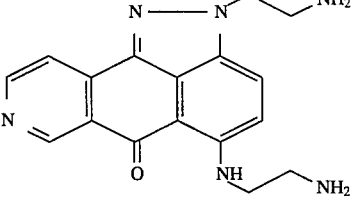 | 40 (b) | LoVo<br>LoVo/Dx<br>R.I. | 12.8 ± 4.2<br>100<br>9 | 18<br>27 | 125<br>150 | 0/8<br>0/8 |
| 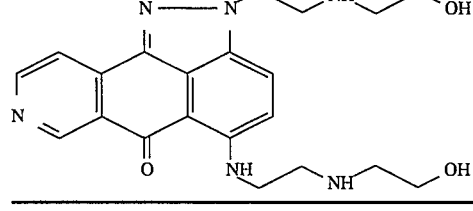 | 6 (c) | LoVo<br>LoVo/Dx<br>R.I. | 10<br>50<br>5 | not<br>tested | — | — |

P 388 i.v./i.v. 1, 4, 7

| Compound | Dose (mg/Kg) | T/C % | Tox. | Compound | Dose (mg/Kg) | T/C % | Tox. |
|---|---|---|---|---|---|---|---|
| Mitoxantrone | 2<br>3 | 176<br>197 | 0/130<br>14/188 | Doxorubicin | 4.6<br>6 | 162<br>176 | 0/8<br>0/39 |

TABLE 3-continued

| | | | | | |
|---|---|---|---|---|---|
| 4 | 147 | 45/56 | 7.5 | 201 | 0/72 |
| | | | 9 | 201 | 8/40 |

(a) Dimaleate salt
(b) Trihydrochloride salt

The pharmaceutical composition may be in the form of tablets, capsules, gel capsules, suppositories, lyophilized powders and solutions for intravenous administration. The invention is illustrated by the following non-limiting examples, and variations which are readily apparent to those skilled in the art.

SYNTHESIS OF COMPOUNDS OF THE INVENTION

PREPARATIVE EXAMPLE 1

Pyridine-3,4-dicarboxylic acid anhydride

A mixture of pyridine 3,4-dicarboxylic acid (15.0 g) and acetic anhydride (30 mL) is refluxed for two hours. The excess acetic anhydride is removed by distillation and the anhydride is collected and purified by sublimation (123° C. at 3 mm Hg) to yield pyridine 3,4-dicarboxylic acid anhydride as a white solid (10.1 g).

m.p.: 74°–76° C.

$^1$H-NMR (CDCl$_3$): 7.94 (d, 1H); 9.24 (d, 1H); 9.39 (s, 1H).

PREPARATIVE EXAMPLE 2

Following the procedure described in Preparative Example 1 and using commercially available pyridine-2,3-dicarboxylic or pyrazine-2,3-dicarboxylic acid as starting materials the following compounds are prepared:

pyridine-2,3-dicarboxylic acid anhydride, m.p. 134°–136° C.;

pyrazine-2,3-dicarboxylic acid anhydride, m.p. 190° C. (dec).

PREPARATIVE EXAMPLE 3

4-(2,5-difluorobenzoyl)nicotinic acid and 3-(2,5-difluorobenzoyl) isonicotinic acid A mixture of pyridine 3,4-dicarboxylic acid anhydride (5.0 g) and aluminum chloride (17.5 g) in 1,4-difluorobenzene (65 mL) is heated in an oil bath at 110° C. for 22 hours. The excess 1,4-difluorobenzene is recovered by distillation. The residue is cooled in an ice-bath and quenched with ice-water (75 mL) and concentrated hydrochloric acid (6.3 mL). The precipitated solid is filtered and dried to yield an approximately 4/1 mixture of 4(2,5-difluorobenzoyl)nicotinic acid and 3-(2,5-difluorobenzoyl) isonicotinic acid respectively, as a white powder (7.7 g) which can be recrystallized from acetonitrile and water.

m.p.: 214°–217° C.

$^1$H-NMR (DMSO-d$_6$): 7.4(m); 7.5(m); 7.90 (m); 8.80 (d); 9.15 (s). Recrystallization of this material (15.97 g) from absolute ethanol (360 mL) yields almost pure 3-(2,5-difluorobenzoyl) isonicotinic acid (

PREPARATIVE EXAMPLE 4

Following the procedure described in Preparative Example 3 and using as starting materials the compounds of Preparative Example 2 the following compounds are prepared:

3-(2',5'-difluorobenzoyl)pyridine-2-carboxylic acid 2-(2',5'-difluorobenzoyl)nicotinic acid (mixture);

2-(2',5'-difluorobenzoyl)pyrazine-3-carboxylic acid, m.p. 151°–153° C.

PREPARATIVE EXAMPLE 5

4-(2',5'-difluorobenzoyl)pyridazine-5-carboxylic acid

Sec-butyllithium (1.32 M in cyclohexane; 1.25 mL) is added dropwise via syringe over 0.25 h to a stirred solution of 1,4-difluorobenzene (0.162 g) in tetrahydrofuran (THF) (5 mL) at –84° C. under a nitrogen atmosphere. The yellow mixture is stirred for an additional 45 min at –80° C. and then added via a canula over 5 min to a stirred solution of pyridazine 4,5-dicarboxylic acid anhydride (0.22 g; prepared according to J.Het Chem. 14, 1099, (1977)) in THF at –80° C. by nitrogen pressure. The mixture is warmed to room temperature overnight and neutralized with amonium chloride. After removal of THF at reduced pressure the resultant tan solid is treated with an aqueous sodium bicarbonate solution (10 mL) and washed with diethyl ether (10 mL). The aqueous phase is acidified with aqueous hydrochloric acid. The precipitate is collected by filtration, washed with cold water (3×10 mL) and dried to give 4-(2',5'-difluorobenzoyl)pyridazine-5-carboxylic acid (0.23 g) as an off-white solid, m.p. 202°–205° C.

PREPARATIVE EXAMPLE 6

Following the procedure described in Preparative Example 3 and using 1-chloro-4-fluorobenzene as starting material for the Friedel-Craft reaction of pyridine-2,3-dicarboxylic acid anhydride or pyrazine-2,3-dicarboxylic acid anhydride, the following compounds are prepared:

3-(2'-fluoro-5'-chlorobenzoyl)pyridine-2-carboxylic acid and 2-(2'-fluoro-5'-chlorobenzoyl)nicotinic acid (mixture);

2-(2'-fluoro-5'-chlorobenzoyl)pyrazine-3-carboxylic acid.

PREPARATIVE EXAMPLE 7

4-(2-methoxy-5-fluorobenzoyl)nicotinic acid and 3-(2-methoxy-5-fluorobenzoyl)isonicotinic acid The mixture of 4-(2,5-difluorobenzoyl)nicotinic acid and 3-(2,5-difluorobenzoyl)isonicotinic acid of Preparative Example 3 (14.1 g) is added to a solution of sodium methylate, prepared by portionwise addition of sodium (6.8 g) to dry methanol (140 mL). The reaction mixture is allowed to react at the reflux temperature for 8.5 hours and at room temperature overnight. The reaction mixture is concentrated to about one third of its volume, water (100 mL) is added and the remaining methanol is removed by distillation. Concentrated HCl (25 mL) is slowly added to the residue while cooling at 10° C. and the obtained precipitate is recovered by suction and washed with 0.1 N HCl, to give an approximately 4:1 mixture of 4-(2-methoxy-5-fluorobenzoyl) nicotinic acid and 3-(2-methoxy-5-fluorobenzoyl)isonicotinic m.p.: >230° C.

$^1$H-NMR (DMSO-d$_6$): 3.40 (s); 7.15 (m); 7.37 (d); 7.42–7.63 (m); 7.26 (d); 8.60 (s); 8.83 (d); 9.07 (s), 13.55 (br.s.).

PREPARATIVE EXAMPLE 8

4-(2-methoxy-5-fluorobenzyl)nicotinic acid (and 3-(2-methoxy-5-fluorobenzyl) isonicotinic acid)

Zinc-copper couple (L.F. Fieser and M. Fieser, Reagents for Organic Synthesis, Vol. 1, page 1292) (1.5 g) is added to a stirred suspension of the mixture of 4-(2-methoxy-5-fluorobenzoyl)nicotinic acid and 3-(2-methoxy-5-fluorobenzoyl) isonicotinic acid of Preparative Example 7 (1.222 g) in formic acid (15 mL) and water (5 mL). After 15 minutes at room temperature the reaction mixture is heated for two hours in a oil bath held at 80° C. After cooling to room temperature the reaction mixture is filtered through a sintered glass filter and the solids are thoroughly washed with 75% aqueous formic acid (10 mL) and then with ethyl acetate (10 mL). The combined filtrates are concentrated to about 5 mL, treated with 0.5N HCl (15 mL) and extracted with ethyl acetate (3×20 mL); finally they are saturated with sodium chloride and further extracted with ethyl acetate/1,2-dimethoxyethane 3/1 (2×20 mL). The combined organic phases are dried over anhydrous sodium sulphate and the solvent removed under reduced pressure to give a yellowish residue. Subjecting this material to silica-gel column chromatography (eluant: ethyl acetate/methanol/acetic acid from 96/4/0 to 90/10/1 v/v/v) 4-(2-methoxy-5-fluorobenzyl) nicotinic acid (0.805 g) is obtained as a yellowish white solid.

m.p.: >220° C.

$^1$H-NMR (DMSO-d$_6$): 3.70 (s,3H); 4.33(s, 2H); 6.91–7.12 (m, 3H); 7.21 (d, 1H); 8.61 (d, 1H); 8.97 (s, 1H). From the above column-chromatography some 3-(2-methoxy-5-fluorobenzyl)isonicotinic acid may also be recovered.

PREPARATIVE EXAMPLE 9

9-fluoro-10-hydroxy-6-methoxybenzo[g]isoquinoline

A mixture of 4-(2-methoxy-5-fluorobenzyl) nicotinic acid (0.63 g) and polyphosphoric acid (15 g) is heated at 110°–120° C. for two hours under stirring. The heating is removed and water (50 mL) is added to the reaction mixture while it is still warm (60° C.). The mixture is cooled to 0° C., neutralized with 20% sodium hydroxide and allowed to stir at room temperature for 1.5 hours; finally it is extracted with 4% methanol in chloroform (4×75 mL). The combined organic phases are washed with brine, dried over anhydrous sodium sulphate and the solvents removed under reduced pressure to give 9-fluoro-10-hydroxy -6-methoxybenzo[g] isoquinoline (0.40 g) as a purple-red solid.

m.p.: >210° C. (from ethanol).

$^1$H-NMR (DMSO-d$_6$):.3.87 (S, 3H); 6.70 –6.83 (m, 2H); 6.92–7.00 (m, 1H); 7.30(d, 1H); 7.50(d, 1H); 8.75 (s, 1H); 12.30 (br.s,1H).

UV (ethanol): lambda max. (nm) (E$_{1\%}$) (cm): 539 (204); 3.98 (513); 3.78(452);266(1232).

IR (KBr): 729, 1245, 1499, 1528, 1620, 1644, and 2838 cm$^{-1}$.

PREPARATIVE EXAMPLE 10

9-fluoro-6-methoxybenzo[g]isoquinoline-5,10-dione

A solution of cerium ammonium nitrate (CAN; 13.70 g) in water (50 mL) is added during twenty minutes to a stirred suspension of 9-fluoro-10-hydroxy-6-methoxybenzo[g]isoquinoline in acetonitrile (150 mL). At the end of the addition the obtained suspension is heated at 60° C. for two hours to give a clear, dark solution which is cooled to room temperature and diluted with water (100 mL). Following removal of acetonitrile by distillation at reduced pressure the aqueous phase is saturated with sodium chloride and extracted with methylene chloride (3×150 mL). The combined organic solutions are dried over anhydrous sodium sulphate and the solvent is removed at reduced pressure. The obtained residue is purified by silica-gel column chromatography (eluant: methylene chloride/ethyl acetate from 85/15 to 75/25 v/v) to give 9-fluoro-6-methoxybenzo[g] isoquinoline5,10-dione as a brown-yellow solid (0.48 g).

m.p.: >220° C.

$^1$H-NMR (CDCl$_3$): 4.05 (s, 3H); 7.38 (dd,J=3.39, 9.39 Hz, 1H); 7.55 (dd, J=10.37, 9.39 Hz, 1H), 8.00 (dd, J=5.09, 0.78 Hz, 1H); 9.07 (d, J=5.09 Hz, 1H); 9.45 (d, J=0, 78 Hz, 1H).

PREPARATIVE EXAMPLE 11

6,9-difluorobenzo[g]isoquinoline-5,10-dione

A solution of the mixture of 4-(2,5-difluorobenzoyl)nicotinic acid and 3-(2,5-difluorobenzoyl)isonicotinic acid of Preparative Example 3 (61.07 g) in 20% oleum (100 mL) is heated at 140° C. while 20% oleum is added in four portions (13.2 mL each) at 20 min-intervals. After the fourth addition the mixture is heated for 20 min, then it is cooled to room temperature and quenched with a mixture of ice (1,500 g), water (1,500 mL) and 35% NaOH (350 mL). The mixture is extracted four times with methylene chloride (1×1,000 mL followed by 3×500 mL). The combined organic solutions are washed with water (2×1,000 mL), dried (Na$_2$SO$_4$) and the solvent removed by roto-evaporation. The dark-red solid obtained (56.0 g) is dissolved in boiling THF (840 mL) and decolorizing charcoal (8.40 g) is added. After 30 min the mixture is filtered while hot and the filtrate concentrated to 200 mL. The precipitate obtained is collected by suction filtration to give 6,9-difluorobenzo[g]isoquinoline-5,10-dione (43.00 g).

m.p.: 201°–203° C.

Concentration of the mother liquor to 70 mL yields a second crop of product (3.35 g), m.p. 200°–202° C.

PREPARATIVE EXAMPLE 12

Following the procedure described in Preparative Example 11 and using as starting materials the compounds of Preparative Examples 4, 5, and 6, the following compounds are obtained:

6,9-difluorobenzo[g]quinoline-5,10-dione, yellow solid, m.p. 251°–252° C.;
6,9-difluorobenzo[g]quinoxaline-5,10-dione, yellow solid, m.p. 230° C. (dec);

6,9-difluorobenzo[g]phthalazine-5,10-dione, yellow solid, m.p. 255°–258° C.;
6-chloro-9-fluorobenzo[g]quinoline-5,10-dione;
6-fluoro-9-chlorobenzo[g]quinoline-5,10-dione;
6-chloro-9-fluorobenzo[g]quinoxaline-5,10-dione.

PREPARATIVE EXAMPLE 13

9-fluoro-6-methoxybenzo[g]isoquinoline-5,10-dione and 6-fluoro-9-methoxybenzo [g]isoquinoline-5,10-dione A solution of sodium methylate is prepared under a nitrogen atmosphere in a dropping addition funnel from dry methanol (97.6 mL) and sodium (2.024 g) portionwise added. When all the sodium disappears the solution is dropped during 2 h, 35 min to a stirred solution of 6,9-difluorobenzo[g]isoquinoline-5,10-dione of Preparative Example 11 (19.615 g) in dry THF (883 mL) at 20° C. At the end of the addition the solution is concentrated to half its volume by roto-evaporation, then it is cooled to 18° C. for 30 min. The solid which separates is recovered by suction filtration and washed with THF (100 mL); then it is suspended in water (80 mL) under stirring overnight and filtered again to give the solid A (7.4 g).

The mother THF solution is concentrated to dryness. The obtained solid is suspended in water (78 mL) under stirring for 1 hour and filtered to give the solid B (12.9 g).

The solid A (9.30 g) in methylene chloride (45 mL) is heated to reflux for 30 min. After cooling to room temperature the solid is recovered by suction filtration, washed with methylene chloride (5×3 mL) and dried vacuum at 40° C. to give 6-methoxy-9-fluorobenzo[g]isoquinoline-5,10-dione (8.65 g) as a pure compound.

m.p.: 248°–250° C.

$^1$H-NMR(CDCl$_3$): 4.05 (s, 3H); 7.40 (dd (J=9.39, 3.91 Hz) 1H); 7.55(dd, J=10.37, 9.39 Hz, 1H); 8.00 (dd,J =5.09, 0.78 HZ, 1H);9.05 (d, J=5.09 Hz, 1H); 9.48(d, J=0.78 Hz, 1H).

The solid B (14.0 g) is dissolved in methylene chloride (140 mL) and the insoluble portion is removed by filtration. The methylene chloride solution is applied on a silica gel (630 g) column chromatography, which is eluted at ambient pressure with methylene chloride. When the yellow chromatographic bands appear well separated the column is eluted with mixtures of methylene chloride/ethyl acetate from 10/1 to 8/2 , to 1/1 to give a 94/6 mixture (HPLC evaluation) of 9-methoxy-6-fluorobenzo[g] isoquinoline-5,10-dione and 6-methoxy-9-fluorobenzo[g] isoquinoline-5,10-dione respectively (6.50 g).

m.p.: 168°–170° C.

PREPARATIVE EXAMPLE 14 a)
9-fluoro-6-hydroxybenzo[g]isoquinoline-5,10-dione and 9-chloro-6-hydroxy benzo[g]isoquinoline-5,10-dione (1/1 mixture: small scale reaction)

A mixture of 9-fluoro-6-methoxybenzo[g]isoquinoline-5, 10-dione (0.072 g) and aluminum trichloride (0.112 g) in dry methylene chloride (40 mL) is stirred at room temperature for 4 hours under a nitrogen atmosphere. An additional portion of aluminum chloride (0.190 g) is added and the mixture is allowed to react at reflux for 1.5 hrs and at room temperature overnight. Following addition of brine (15 mL) the aqueous phase is separated and extracted with methylene chloride (3×5 mL). The combined organic solutions are dried over anhydrous sodium sulphate and the solvent is removed by distillation at reduced pressure to give an approximately 1:1 mixture (0.070 g) of 9-fluoro-6-hydroxybenzo[g]isoquinoline-5,10-dione (slower moving yellow spot on silica gel TLC plate, eluant methylene chloride/ethyl acetate 70/30) and 9-chloro-6-hydroxybenzo[g]isoquinoline-5,10-dione (faster moving yellow spot on the above chromatographic system) which is used without further purification for the next step.

9-fluoro-6-hydroxybenzo[g]isoquinoline-5,10-dione has the following $^1$H-NMR spectrum (CDCl$_3$): 7.38 (dd, 1H); 7.53 (dd, 1H); 8.09 (dd, 1H); 9.15 (d, 1H); 9.57(d, 1H); 12.56 (s, 1H).

9-chloro-6-hydroxybenzo[g]isoquinoline-5,10-dione has the following $^1$H-NMR spectrum (CDCl$_3$): 7.91 (d, 1H); 7.75 (d, 1H); 8.07 (dd, 1H); 9.13 (d, 1H); 9.58 (d, 1H); 12.95 (s, 1H). b) 9-fluoro-6-hydroxybenzo[g]isoquinoline-5,10-dione and 9-chloro-6-hydroxy benzo[g]isoquinoline-5,10-dione (9/1 mixture: multigram preparation):

Aluminum chloride (19.05 g) is added in one portion to a stirred refluxing solution of 6-methoxy-9-fluorobenzo[g] isoquinoline-5,10-dione (7.20 g) in methylene chloride (432 mL). After refluxing for 4 hours the reaction mixture is cooled and poured in water (1,300 mL). Methylene chloride (200 mL) is added and after stirring for 10 min the organic phase is separated. The aqueous solution is saturated with NaCl and further extracted with methylene chloride (3×400 mL). The combined organic solutions are washed with brine (1,000 mL), dried and the solvent removed by roto-evaporation. The brown solid obtained (6.5 g) is recrystallized from ethyl acetate/n-hexane 1/1 (65 mL) to yield a 9/1 mixture ($^1$H-NMR evaluation) of 9-fluoro-6-hydroxybenzo [g]isoquinoline-5,10-dione and 9-chloro-6-hydroxybenzo [g]isoquinoline-5,10-dione respectively (6.00 g).

m.p.: partial melting at 179°–181° C., complete melting at 193°–195° C.

PREPARATIVE EXAMPLE 15 a)
9-fluoro-6-(p-toluenesulfonyloxy)benzo[g]isoquinoline-5,10-dione and
9-chloro-6-(p-toluenesulfonyloxy)benzo[g]isoquinoline-5,10-dione 1/1 mixture; small scale preparation)

The 1:1 mixture of 9-fluoro-6-hydroxybenzo[g]isoquinoline-5,10-dione and 9-chloro-6-hydroxybenzo[g]isoquinoline-5,10-dione, of Preparative Example 14a, (0.060 g) is dissolved in dry pyridine (2 mL) and p-toluenesulfonyl chloride (0.095 g) is added. After stirring at room temperature for one hour, triethylamine (0.25 mL) is added and stirring is continued for one additional hour. The reaction mixture is concentrated almost to dryness and partitioned between 1 N HCl (4 mL)-20% ammonium sulfate (6 mL) and ethyl acetate (10 mL). The aqueous phase is separated, extracted with ethyl acetate (3×5 mL) and discarded. The combined organic solutions are dried over anhydrous sodium sulphate and concentrated to dryness to give an approximately 1:1 mixture (0.095 g) of 9-fluoro-6-(p-toluenesulfonyloxy)benzo[g]isoquinoline-5,10-dione and 9-chloro-6-(p-toluenesulfonyloxy)benzo[g]isoquinoline-5, 10-dione which is sued without further purification for the next step.

The pure single compounds can be obtained by silica-gel column chromatography of this mixture (eluant: methylene chloride/n-hexane/ethyl acetate from 50/45/5 to 50/40/10 v/v/v) and they have the following analytical data:

9-fluoro-6-(p-toluenesulfonyloxy)benzo[g]iso-quinoline-5,10-dione: m.p. 173°–174° C.
$^1$H-NMR (CDCl$_3$): 2.45 (s, 3H), 7.35 (d, 2H); 7.50–7.57 (m, 2H); 7.82–7.94 (m, 3H); 9.08 (d, 1H); 9.48 (s, 1H).

9-chloro-6-(p-toluenesulfonyloxy)benzo[g]isoquinoline-5,10-dione:
m.p.: 180°–181° C.
$^1$H-NMR (CDCl$_3$): 2.45 (s, 3H), 7.35 (d, 2H); 7.47 (d, 1H); 7.78–7.91 (m, 4H), 9.07 (d, 1H); 9.48 (s, 1H).

b)
9-fluoro-6-(p-toluenesulfonyloxy)benzo[g]isoquinoline-5,10-dione and
9-chloro-6-(p-toluenesulfonyloxy)benzo[g]isoquinoline-5,10-dione (9/1 mixture; multigram preparation):

Triethylamine (8.20 mL) is added to a stirred suspension of the 9/1 mixture of 9-fluoro-6-hydroxybenzo[g]isoquinoline-5,10-dione and 9-chloro-6-hydroxybenzo [g]isoquinoline-5,10-dione respectively of Preparative Example 14b (5.53 g) and p-toluenesulfonylchloride (8.47 mL) in methylene chloride (166 mL). The reddish-violet solution obtained is left at room temperature under a nitrogen atmosphere for 1 hour and then it is poured into water (500 mL). The organic phase is separated and the aqueous solution is further extracted with methylene chloride (100 mL). The combined organic solutions are dried (Na$_2$SO$_4$) and concentrated to dryness. The obtained solid is suspended in n-hexane (100 mL) for 1 hour and filtered to give a 9:1 mixture ($^1$H-NMR evaluation) of 9-fluoro-6-(p-toluenesulfonyloxy)benzo [g]isoquinoline-5,10-dione and 9-chloro-6-(p-toluenesulfonyloxy)benzo[g]iso quinoline-5,10-dione respectively (8.85 g).
m.p.: 156°–158° C.

PREPARATIVE EXAMPLE 16

6-fluoro-9-hydroxybenzo[g]isoquinoline-5,10-dione and 6-chloro-9-hydroxybenzo [g]iso quinoline-5,10-dione Following the procedure of Preparative Example 14 and using 6-fluoro-9-methoxybenzo[g]isoquinoline-5,10-dione obtained in Preparative Example 13 as starting material, an approximately 2:1 mixture of 6-fluoro-9-hydroxybenzo[g] isoquinoline-5,10-dione and 6-chloro-9-hydroxybenzo[g] iso quinoline-5,10-dione is obtained as a yellow powder, m.p. 175–177/188°–190° C.

PREPARATIVE EXAMPLE 17

6-fluoro-9-(p-toluenesulfonyloxy)benzo[g]isoquinoline-5,10-dione and
6-chloro-9-(p-toluenesulfonyloxy)benzo[g]isoquinoline-5,10-dione Following the procedure of Preparative Example 15 and using the mixture of 6-fluoro-9-hydroxybenzo[g]isoquinoline-5,10-dione and 6-chloro-9-hydroxybenzo [g]isoquinoline-5,10-dione obtained in Preparative Example 16 as starting material, an approximately 60/40 mixture of 6-fluoro-9-(p-toluenesulfonyloxy)benzo [g]isoquinoline-5,10-dione and 6-chloro-9-(p-toluenesulfonyloxy)benzo[g]isoquinoline-5,10-dione is obtained as a yellow powder, m.p. 193°–195° C. (from methylene chloride).

PREPARATIVE EXAMPLE 18

3-(5-chloro-2-fluorobenzoyl)isonicotinic acid and 4-(5-chloro-2-fluorobenzoyl) nicotinic acid Sec-butyllithium (1.3M in cyclohexane; 6.0 mL) is added dropwise via a syringe to a stirred solution of 1-chloro-4-fluorobenzene (0.97 g) in THF (70 mL) at –75° C. which is kept under a nitrogen atmosphere. After stirring for additional 30 min, the yellow mixture is transferred dropwise via a jacketed canula into a stirred mixture of pyridine-3,4-dicarboxylic acid anhydride (1.00 g) in THF (100 mL) at –78° C. under a nitrogen blanket. The pale yellow solution is allowed to warm to –20° C. for 4 hours. The THF is removed at reduced pressure. The yellow solid obtained is dissolved in water (10 mL), cooled to 0° C., and acidified with dilute HCl in an ice-bath and the resulting precipitate is collected by filtration. Upon heating the white solid with acetone (30 mL), an insoluble material remains (0.095 g), which by $^1$H-NMR analysis is a 94/4 mixture of 3-(5-chloro-2-fluorobenzoyl)isonicotinic acid and 4-(5-chloro-2-fluorobenzoyl)nicotinic acid, respectively.
m.p.: 289°–291° C.

After centrifugation, the supernate is removed and roto-evaporated to give crystals of a 94/6 mixture (by $^1$H-NMR analysis) of 4-(5-chloro-2-fluorobenzoyl)nicotinic acid and 3-(5-chloro-2-fluorobenzoyl)isonicotinic acid respectively (0.947 g).
m.p.: 236°–237° C.

Sublimation of this mixture (0.025 g) at 180°–205° C./0.5 mm Hg gives a white solid with a 98/2 ratio of 4-(5-chloro-2-fluorobenzoyl)nicotinic acid and 3-(5-chloro-2-fluorobenzoyl)isonicotinic acid respectively (20 mg).

4-(5-chloro-2-fluorobenzoyl)nicotinic acid: $^1$H-NMR (CDCl$_3$/CD$_3$OD 9/1): 6.96 (m, 1H); 7.21 (d, 1H); 7.45 (m, 1H); 7.86 (m, 1H); 8.76 (d, 1H); 9.18 (s, 1H).
3-(5-chloro-2-fluorobenzoyl)isonicotinic acid: $^1$H-NMR (DMSO-d$_6$): 7.37 (m, 1H); 7.75 (m, 2H); 7.83 (d, 1H); 8.77 (s, 1H); 8.90 (d, 1H).

PREPARATIVE EXAMPLE 19

4-(5-chloro-2-fluorobenzyl)nicotinic acid

Zinc-copper couple (0.75 g) is added to a stirred mixture of 4-(5-chloro-2-fluorobenzoyl)nicotinic acid and 3-(5-chloro-2-fluorobenzoyl)isonicotinic acid of Preparative Example 18 (94/6 on a molar base; 0.60 g) in 75% formic acid. The exothermic and effervescent reaction mixture is stirred for 15 min before heating to 80° C. for 2 hours. After cooling to 40° C., the mixture is filtered through a sintered glass funnel. The solid is washed with 75% formic acid (1×5 mL) and ethyl acetate (2×5 mL). The mixture is concentrated by roto-evaporation to about 2 mL. The orange oil obtained is dissolved in 0.5N HCl (3 mL) and extracted with ethyl acetate (3×10 mL), then saturated with NaCl and extracted with ethyl acetate/1,2-dimethoxyethane (2×5 mL). The combined extracts are dried with Na$_2$SO$_4$ and the solvents removed by roto-evaporation to yield a yellow foam. The foam (0.541 g) is recrystallized in hot acetonitrile (1 mL) to yield 4-(5-chloro-2-fluorobenzyl)nicotinic acid (0.142 g).

m.p.: 174°–176° C.

$^1$H-NMR (CDCl$_3$/CD$_3$OD 9/1): 4.43 (s, 2H); 6.79 (m, 1H); 6.86 (m, 1H); 6.95 (m, 1H); 7.11 (d, 1H); 8.55 (d, 1H); 9.12 (s, 1H).

PREPARATIVE EXAMPLE 20

9-chloro-6-fluorobenzo[g]isoquinoline-5,10-dione

Fuming sulfuric acid (30% SO$_3$; 0.31 mL) is added to 4-(5-chloro-2-fluorobenzyl)nicotinic acid of Preparative Example 19. The dark mixture is heated quickly to 130° C. for 10 min in a flask fitted with a cotton filled drying tube. After cooling to room temperature, the reaction mixture is quenched with ice (3 g) and extracted with methylene chloride (4×7 mL). The combined extracts are dried with Na$_2$SO$_4$ and the solvent is removed by roto-evaporation to yield 9-chloro-6-fluorobenzo[g]isoquinoline-5,10-dione as a yellow solid (0.045 g; 82% yield).

m.p.: 204°–206° C.

$^1$H-NMR (CDCl$_3$): 7.45 (m, 1H); 7.83 (m, 1H); 7.98 (d, 1H); 9.08 (d, 1H); 9.49 (s, 1H)

PREPARATIVE EXAMPLE 21

9-fluoro-6-(p-toluenesulfonyloxy)benzo[g]isoquinoline-5,10-dione-2-oxide

A solution of 3-chloroperoxybenzoic acid (3.92 g; 55% titre) in dichloromethane (50 mL) is dropped during 5 min into a mixture of 9-fluoro-6-(p-toluenesulfonyloxy)benzo[g]isoquinoline-5,10-dione (1.98 g) in dichloromethane (20 mL). Care is taken to avoid the addition of the aqueous layer that separates from the dichloromethane solution of 3-chloroperoxybenzoic acid. An exothermic reaction ensues, and at the end of the addition the mixture is refluxed overnight. After cooling to room temperature the reaction mixture is diluted with dichloromethane (50 mL) and the organic solution is washed with water (3×30 mL). After drying over sodium sulfate the organic solution is concentrated to a volume of about 20 mL, diluted with absolute ethanol (30 mL) and concentrated to a small volume. After stirring at 0° C. for 1 h a yellow solid separates which is filtered, to give 9-fluoro-6-(p-toluenesulfonyloxy)benzo[g]isoquinoline-5,10-dione-2-oxide (1.35 g).

m.p. 234°–236° C.;

PREPARATIVE EXAMPLE 22

Following the procedure of preparative example 21 and using as starting materials the mixture of 6-fluoro-9-(p-toluenesulfonyloxy)benzo[g]isoquinoline-5,10-dione and 6-chloro-9-(p-toluenesulfonyloxy)benzo[g]isoquinoline-5,10-dione of Preparative Example 17 or 9-chloro-6-fluorobenzo[g]isoquinoline-5,10-dione of Preparative Example 20, the following compounds are prepared:

6-fluoro-9-(p-toluenesulfonyloxy)benzo[g]isoquinoline-5,10-dione-2-oxide;
6-chloro-9-(p-toluenesulfonyloxy)benzo[g]isoquinoline-5,10-dione-2-oxide;
9-chloro-6-fluorobenzo[g]isoquinoline-5,10-dione-2-oxide;

PREPARATIVE EXAMPLE 23

4-(2'-fluoro-5'-chlorophenyl)-4-oxo-2E-butenoic acid

Finely pulverized maleic anhydride (3.0 g) is added portionwise to a mixture of 1-chloro-4-fluorobenzene (24.6 g) and anhydrous aluminium chloride (11.56 g). A gas bubbler is attached to the top of the condenser and the mixture is heated in an oil bath at 80°–85° C. for 2 hours at which time little hydrogen chloride gas evolution is evident. The mixture is cooled and the excess 1-chloro-4-fluorobenzene is recovered by distillation at water aspirator pressure. The resultant mixture is quenched with ice and then steam distilled to remove the last traces of the 1-chloro-4-fluorobenzene. Concentrated hydrochloric acid (10 mL) is added to the cooled mixture and the resultant solid collected by filtration (9.2 g). This material is taken up in boiling benzene (50 mL), treated with decolorizing charcoal and filtered through a celite bed. On standing overnight, the yellow solid is collected by filtration (2.45 g). A second recrystallization from benzene (40 mL) leads to 4-(2'-fluoro-5'-chlorophenyl)-4-oxo-2E-butenoic acid (2.1 g) as pure regioisomer.

m.p. 146°–147° C.

$^1$H NMR (CDCl$_3$) δ7.81 (dd, J$_{HH}$=15.4 Hz, J$_{HF}$=3.3 Hz, 1H), 7.79 (dd, J$_{HF}$=6.1 Hz, J$_{HH}$=2.7 Hz, 1H), 7.54 (m, J$_{HH}$=10 Hz, J$_{HF}$=4.7 Hz, J$_{HH}$=2.7 Hz, 1H), 7.15 (dd, J$_{HH}$=10 Hz, J$_{HF}$=9 Hz, 1H), 6.85 (dd, J$_{HH}$=15.4 Hz, J$_{HF}$=1.2 Hz, 1H).

PREPARATIVE EXAMPLE 24

Methyl 4-(2'-fluoro-5'-chlorophenyl)-4-oxo-2E-buteonate

A methanol (90 mL) solution of 4-(2'-fluoro-5'-chlorophenyl)-4-oxo-2E-buteonic acid of Preparative Example 23 (4.6 g) containing concentrated sulfuric acid (20 drops) is heated under reflux for 2 h. The mixture is cooled to room temperature and the removal of the methanol by rotary evaporation yields a pale yellow oil. Ice water is added to the residue and the solid is collected by filtration and washed several times with ice water. The solid is taken up in pentane (100 mL) and the solution dried over sodium sulfate. The drying agent is removed and the pentane solution placed in the freezer for three days. The pure methyl 4-(2'-fluoro-5'-chlorophenyl)-4-oxo-2E-buteonate is collected by filtration (3.2 g).

mp 42°–43° C.;

$^1$H NMR (CDCl$_3$) δ7.78 (dd, J$_{HF}$ 6.1 Hz, J$_{HH}$=2.7 Hz, 1H), 7.70 (dd, J$_{HH}$=15.6 Hz, J$_{HF}$=3,3 Hz, 1H), 7.51 (m, J$_{HH}$=9.8 Hz, J$_{HF}$=4.5 Hz, J$_{HH}$=2.7 Hz, 1H), 7.13 (dd, J$_{HH}$=9.8 Hz, J$_{HF}$=8.9 Hz, 1H), 6.84 (dd, J$_{HH}$=15.6 Hz, J$_{HF}$=1.3 Hz, 1H) 3.84 (s, 3H).

PREPARATIVE EXAMPLE 25

Methyl 4-(2'-fluoro-5'-chlorobenzoyl)-5-hydroxynicotinate

A mixture of methyl 4-(2'-fluoro-5'-chlorophenyl)-4-oxo-2E-buteonate of Preparative Example 24 (2.0 g) and 5-ethoxyoxazole-2-carboxylic acid (1.5 g; prepared according to Rec. Trav. Chim. des Pays-Bas, (1913), 32, 144) is heated at 90° C. for 1.75 h at which time carbon dioxide evolution has ceased. The cooled reaction mixture (orange-red solid) is washed with ethyl acetate (5 mL). The pale yellow solid is collected by filtration (1.43 g). Additional methyl 4-(2'-fluoro-5'-chlorobenzoyl)-5-hydroxynicotinate can be obtained from the filtrate (0.4 g; total recovery 1.82 g). Recrystallization from ethyl acetate (7 mL) gives colorless crystals.

mp 163°–164° C.;

$^1$H NMR (CDCl$_3$) δ8.71 (s, 1H), 8.55 (s, 1H), 7.86 (dd, $J_{HH}$=2.7 Hz, $J_{HF}$=6.2 Hz, 1H), 7.50 (m, $J_{HH}$=10.1 Hz, $J_{HF}$=4.4 Hz, $J_{HH}$=2.7 Hz, 1H), 7.04 (dd, $J_{HH}$=10.1 Hz, $J_{HF}$=8.8 Hz, 1H), 3.71 (s, 3H). X-ray analysis unambiguously establishes the regiochemistry of the Diels-Alder reaction.

PREPARATIVE EXAMPLE 26

4-(2'-fluoro-5'-chlorobenzoyl)-5-hydroxynicotinic acid

Methyl 4-(2'-fluoro-5'-chlorobenzoyl)-5-hydroxynicotinate of Preparative Example 25 (1.2 g) is added to a solution of sodium hydroxide (0.67 g) in water (4 mL) and methanol (12 mL). A yellow solution is obtained after 5 min. The mixture is stirred at room temperature for 1.25 h. The resulting solution is acidified with 1N hydrochloric acid (14 mL) to pH=2 and the mixture is allowed to stand overnight. The white solid is collected by filtration and washed with water (3×5 mL) and dried to yield 4-(2'-fluoro-5'-chlorobenzoyl)-5-hydroxynicotinic acid (1.04 g).

m.p. 262°–264° C.;

$^1$H NMR (DMSO-d$_6$) δ13.60 (s, 1H), 10.70 (s, 1H), 8.60 (s, 1H), 8.45 (s, 1H), 7.75 (m, 2H), 7.36 (t, 1H J=9.4 Hz).

PREPARATIVE EXAMPLE 27

4-(2'-fluoro-5'-chlorobenzyl)-5-hydroxynicotinic acid

To a stirred suspension of zinc dust (>230 mesh; 100 mg) in 75% formic acid (1.3 mL), at 80° C. (external bath temperature), 4-(5'-chloro-2'-fluorobenzoyl)-5-hydroxynicotinic acid of Preparative Example 26 (100 mg) is added portionwise during 5 minutes. Three further portions of zinc dust (3×50 mg) are subsequently added every 30 min. Stirring is continued for further 10 minutes after the last addition of zinc dust and the reaction mixture is then partitioned between ethyl acetate (10 mL) and 0.5N HCl (10 mL). The aqueous phase is extracted three times with ethyl acetate (3×10 mL), saturated with NaCl and further extracted with ethyl acetate (10 mL). The combined organic phases are washed with brine (10 mL), dried over Na$_2$SO$_4$ and concentrated to dryness. The residue is triturated in acetone (2 mL) and allowed to crystallize overnight. The white solid is collected by filtration, washed with methyl tert-butyl ether and dried under vacuum at 100° C. 4-(2'-fluoro-5'-chlorobenzyl)-5-hydroxynicotinic acid is obtained as a white solid (47 mg).

m.p.>280° C.

$^1$H NMR (DMSO-d$_6$) d13.25 (s, 1H), 10.34 (s, 1H), 8.47 (s, 1H), 8.30 (s, 1H), 7.25 (m, 2H), 6.80 (dd, 1H), 4.27 (s, 2H).

PREPARATIVE EXAMPLE 28

9-chloro-6-fluoro-4-hydroxybenzo[g]isoquinoline-5,10-dione

A mixture of 4-(5'-chloro-2'-fluorobenzyl)-5-hydroxynicotinic acid of Preparative Example 27 (0.15 g) and 20% oleum (2 mL) is stirred for 45 minutes at 125°–130° C. (external bath temperature). The reaction mixture is then allowed to cool at room temperature and poured over 20 g of crushed ice and the resultant mixture neutralized with solid sodium bicarbonate to pH=7. The dione is extracted with dichloromethane (4×20 mL) and the combined organic phases are dried over MgSO$_4$ and concentrated to dryness. The product is obtained as a yellow-tan solid (0.12 g) which darkens on standing in air.

m.p. 227°–228° C.;

$^1$H NMR (CDCl$_3$) d 11.48 (s, 1H), 9.02 (s, 1H), 8.86 (s, 1H), 7.88 (dd, $J_{HH}$=9.1 Hz, $J_{HF}$=4.5 Hz, 1H), 7.47 (dd, $J_{HF}$=10.2 Hz, $J_{HH}$=9.1 Hz, 1H).

PREPARATIVE EXAMPLE 29

9-chloro-6-fluoro-4-(p-methoxybenzyloxy)benzo[g]isoquinoline-5,10-dione

Step a)

Anhydrous cupric chloride (8 mg) is added to a mixture of 4-methoxybenzyl alcohol (2.76 g) and 1,3-diisopropylcarbodiimide (3.13 mL) under a nitrogen atmosphere. The reaction is quite exothermic and it is cooled with an ice bath for 1 h. The mixture is then heated for 3.5 h at 60° C. The product was purified by distillation to give O-p-methoxybenzyl-N,N'-diisopropylisourea (4 g).

bp 98°–100° C. (0.05 mm).

$^1$H NMR (CDCl$_3$) d 7.32 (d, $J_{HH}$=9 Hz, 2H), 6.86 (d, $J_{HH}$=9 Hz, 2H), 5.02 (s, 2H), 3.80 (s, 3H), 4.40 (m, 1H), 3.20 (m, 1H), 1.12 (dd, overlapping, 12H).

Step b)

A solution of 9-chloro-6-fluoro-4-hydroxybenzo[g]isoquinoline-5,10-dione of Preparative Example 28 (0.050 g) and O-p-methoxybenzyl-N,N'-diisopropylisourea prepared in Step a (0.095 gs) in dichloromethane (1 mL) is stirred at room temperature for 3.5 h under a nitrogen blanket. The dark reddish-brown mixture is purified by flash chromatography over silica gel using gradient elution commencing with 100:2 (300 mL) followed by 100:4 (300 mL) mixtures of chloroform: tert-butyl methyl ether. Removal of the eluent yields 9-chloro-6-fluoro-4-(p-methoxy benzyloxy)benzo[g]isoquinoline-5,10-dione as a yellow-brown solid (0.032 g.)

m.p. 155°–157° C.;

$^1$NMR (CDCl$_3$) d 9.06 (s, 1H), 8.78 (s, 1H), 7.75 (dd, $J_{HH}$=9.0 Hz, $J_{HF}$=4.6 Hz, 1H), 7.45 (d, $J_{HH}$8.3 Hz, 2H), 7.38 (t, $J_{HF}$=9.8 Hz, $J_{HH}$=9.0 Hz, 1H),, 6.93 (d, $J_{HH}$=8.3 Hz, 2H), 5.36 (s, 2H), 3.82 (s, 3H).

PREPARATIVE EXAMPLE 30

9-Fluoro-6-(p-toluenesulfonyloxy)benzo[g]phthalazine-5,10-dione or
9-Fluoro-6-(p-toluenesulfonyloxy)benzo[g]quinoxaline-5,10-dione Following the procedure of Preparative Example 13 and using 6,9-difluorobenzo[g]phthalazine-5,10-dione or 6,9-difluorobenzo[g]quinoxaline-5,10-dione of Preparative Examples 12, 9-fluoro-6-methoxybenzo[g]phthalazine-5,10-dione or 9-fluoro-6-methoxybenzo[g]quinoxaline-5,10-dione are prepared, respectively.

These latter intermediates are reacted according to the procedure of Preparative Example 14 to give 9-fluoro-6-hydroxybenzo[g]phthalazine-5,10-dione or 9-fluoro-6-hydroxybenzo[g]quinoxaline-5,10-dione, in mixture with some of the respective 9-chloro-derivatives.

Reaction of these intermediates with p-toluenesulfonylchloride according to Preparative Example 15 gives 9-fluoro-6-(p-toluenesulfonyloxy)benzo[g]phthalazine-5,10-dione or 9-fluoro-6-(p-toluenesulfonyloxy)benzo[g]quinoxaline-5,10-dione.

EXAMPLE 1

5-(p-toluenesulfonyloxy)-2-methylisoquino[8,7,6-cd]indazole-6(2H)-one

The 1:1 mixture of 9-fluoro-6-(p-toluenesulfonyloxy)benzo[g]isoquinoline-5,10-dione and 9-chloro-6-(p-toluenesulfonyloxy)benzo[g]isoquino line-5,10-dione, of Preparative Example 15a, (0.041 g) is dissolved in dry pyridine (2 mL) and a freshly prepared 1M solution of N-methyhydrazine in pyridine (0.183 mL) is added. After stirring for three hours at room temperature the reaction mixture is concentrated to dryness and added with water (5 mL), with $NaH_2PO_4$ saturated solution (5 mL) and extracted several times with methylene chloride (50 mL). The combined organic solutions are dried ever anhydrous sodium sulfate and the solvent is removed at reduced pressure. The obtained residue is purified by silica-gel column chromatography (eluant: methylene chloride/ethyl acetate 90/10 v/v (50 mL), then 75/25 (50 mL), then 60/40 (50 mL) and finally 40/60 (50 mL) to give 2-methyl-5-(p-toluenesulfonyloxy)isoquino [8,7,6-cd]indazole-6(2H)-one.

$^1$H-NMR ($CDCl_3$): 2.42 (s, 3H); 4.25 (s, 3H); 7.33 (d, 2H); 7.53 (d, 1H); 7.63 (d, 1H); 7.95 (d, 2H); 8.07 (d, 1H) 8.80 (d, 1H); 9.50 (s, 1H).

EXAMPLE 2

2-[2-(dimethylamino)ethyl)]-5-(p-toluenesulfonyloxy)isoquino[8,7,6-cd]indazole-6(2H)-one Under a nitrogen atmosphere a solution of N-[2-(dimethylamino)ethyl]hydrazine (J. Med. Chem. 7, 493, 1964) (1.86 g) in anhydrous THF (6.0 mL) is added during 30' to the stirred 9:1 mixture of 9-fluoro-6-(p-toluenesulfonyloxy) benzo[g]isoquinoline-5,10-dione and 9-chloro-6-(p-toluenesulfonyloxy) benzo [g]isoquinoline-5,10-dione of Preparative Example 15b (2.4 g) in THF (24 mL) containing N,N-diisopropylethylamine (1.10 mL). A slightly exothermic reaction ensures, and the reaction temperature increases from 20° C. to 25° C. After one hour at room temperature the reaction mixture is poured in water (240 mL) and the suspension obtained is stirred for 30'. The solid is separated by suction, washed with water and dried at 40° C. to give 2-[2-(dimethylamino)ethyl)]-5-(p-toluenesulfonyloxy)isoquino[8,7,6-cd]indazole-6(2H)-one (1.44 g).

m.p.: 139°–141° C.

$^1$H-NMR ($CDCl_3$): 2.35 (s, 6H); 2.45 (s, 3H); 2.95 (t, 2H); 4.65 (t, 2H); 7.35 (d, 2H); 7.52 (d, 1H); 7.80 (d, 1H); 7.95 (d, 2H); 8.10 (d, 1H); 8.80 (d, 1H); 9.55 (s, 1H).

EXAMPLE 3

2-[2-(N-tert-butoxycarbonylamino)ethyl]-5-(p-toluenesulfonyloxy)isoquino[8,7,6-cd]indazole-6(2H)-one (2-N-tert-butoxycarbonylaminoethyl)hydrazine is prepared by reaction of N-t-butoxycarbonyl-2-chloro-ethylamine with hydrazine following a procedure adapted from J. Med. Chem. 7, 493, (1964). Under a nitrogen atmosphere a solution of (2-N-tert-butoxycarbonylaminoethyl)hydrazine (9.2 g) in anhydrous THF (10 mL) is added during 30' to the stirred 9:1 mixture of 9-fluoro-6-(p-toluenesulfonyloxy)benzo[g]isoquinoline-5,10-dione and 9-chloro-6-(p-toluenesulfonyloxy)benzo [g]isoquinoline-5,10-dione of Preparative Example 15b (3.0 g) in THF (25 mL) containing N,N-diisopropylethylamine (1.38 mL). A slightly exothermic reaction ensues, and the reaction temperature increases from 21° C. to 24° C. After stirring for one hour at room temperature the obtained precipitate is recovered by suction, washed with THF/n-hexane 1/1 (15 mL) and dried at 40° C. under vacuum, to give 2-[2-(N-tert-butoxycarbonylamino)ethyl[-5-(p-toluenesulfonyloxy)iso-quino[8,7,6-cd]indazole-6(2H)-one (1.33 g).

m.p.: 206°–208° C.

$^1$H-NMR ($CDCl_3$): 1.4 (s, 9H); 2.45 (s, 3H); 3.75 (q, 2H); 4.70 (t, 2H); 4.92 (br, 1H); 7.35 (d, 2H); 7.50 (d, 1H); 7.75 (d, 1H); 7.95 (d, 2H); 8.09 (d, 1H); 8.78 (d, 1H); 9.50 (s, 1H).

EXAMPLE 4

2-[2-[(2-hydroxyethyl)amino]ethyl]-5-(p-toluenesulfonyloxy)isoquino[8,7,6-c]indazole-6(2H)-one A solution of N-[2-[(2-hydroxyethylamino)ethyl]]hydrazine (J. Het. Chem., 26, 85, (1989); 0.179 g) in absolute ethanol (0.5 mL) is dropped into a stirred solution of the 9:1 mixture of 9-fluoro-6-(p-toluenesulfonyloxy)benzo[g]isoquinoline-5,10-dione and 9-chloro-6-(p-toluenesulfonyloxy)benzo [g]isoquinoline-5,10-dione of Preparative Example 15b (0.200 g) in THF (2.0 mL) containing triethylamine (0.073 mL). After stirring for 2 hours at room temperature an additional amount of N-[2-[(2-hydroxyethylamino)ethyl]]hydrazine (0.179 g) in absolute ethanol (0.5 mL) is added and after two additional hours the reaction mixture is concentrated to the volume of about 1 mL. Water (20 mL) is added and the mixture is allowed to stir at room temperature overnight. The precipitate is collected by suction filtration, dried under vacuum at 40° C. and finally sludged in boiling ethyl acetate to give 2-[2-[(2-hydroxyethyl)amino[ethyl]-5-(p-toluenesulfonyloxy)isoquino[8,7,6-c]indazole-6(2H)-one (0.060 g).

m.p.: 131°–133° C.

$^1$H-NMR (DMSO-$d_6$/$D_2O$): 2.45 (s, 3H); 2.62 (t, 2H); 3.13 (t, 2H); 3.40 (t, 2H); 4.65 (t, 2H); 7.25 (d, 1H); 7.40 (d, 2H); 7.75 (d, 2H); 7.95 (d, 1H); 8.15 (d, 1H); 8.80 (d, 1H); 9.40 (s, 1H).

EXAMPLE 5

Preparation of 2-(aminoalkyl)-5-(p-toluenesulfonyloxy) isoquino[8,7,6-cd]indazole-6(2H)-ones Using the procedure of Examples 1–4, the following compounds are obtained by reaction of the mixtures of 9-fluoro-6-(p-toluenesulfonyloxy) benzo[g] isoquinoline-5,10-dione and 9-chloro-6-(p-toluenesulfonyloxy)benzo[g] isoquinoline-5,10-dione of Preparative Example 15, with a substituted hydrazine selected from the group of N-[2-(diethylamino)ethyl]hydrazine [J. Med. Chem., 7, 493, (1964)], N-[3-dimethyl amino)propyl]hydrazine [J. Het. Chem., 23, 1491, (1986)], N-(2-amino ethyl)hydrazine [J. Het. Chem., 23, 1491, (1986)], N-[2-(methylamino) ethyl] hydrazine, N-(2-hydroxyethyl)hydrazine, N-(3-aminopropyl)hydrazine [J. Het. Chem., 23, 1491, (1986)]:

2-[2-(diethylamino)ethyl]-5-(p-toluenesulfonyloxy)isoquino[8,7,6-cd]indazole-6(2H)-one;
2[3-(dimethylamino)propyl]-5-(p-toluenesulfonyloxy)isoquino[8,7,6-cd]indazole-6(2H)-one;
2-[2-(amino)ethyl]-5-(p-toluenesulfonyloxy)isoquino[8,7,6-cd]indazole-6(2H)-one;
2-[2-(methylamino)ethyl]-5-(p-toluenesulfonyloxy)isoquino [8,7,6-cd]indazole-6(2H)-one;
2-[3-(amino)propyl]-5-(p-toluenesulfonyloxy)isoquino[8,7,6-cd]indazole-6(2H)-one;
2-[2-(hydroxy)ethyl]-5-(p-toluenesulfonyloxy)isoquino[8,7,6-cd]indazole-6(2H)-one, m.p. 211°–213° C.

EXAMPLE 6

2-(aminoalkyl)-5-(p-toluenesulfonyloxy)isoquino[5,6,7-cd]indazole-6(2H)-ones

Using the procedure of Examples 1–4, the following compounds are obtained by reaction of the mixture of 6-fluoro-9-(p-toluenesulfonyloxy)benzo[g]isoquinoline-5,10-dione and 6-chloro-9-(p-toluenesulfonyloxy)benzo[g]isoquinoline-5,10-dione of Preparative Example 17 with the properly selected substituted-hydrazines:

2-[2-(dimethylamino)ethyl)]-5-(p-toluenesulfonyloxy)isoquino[5,6,7-cd]indazole-6(2H)-one, m.p. 168°–170° C.;
2-[2-(N-tert-butoxycarbonylamino)ethyl]-5-(p-toluenesulfonyloxy)isoquino[5,6,7-cd]indazole-6(2H)-one, m.p. 169°–171° C.;
2-[2-[(2-hydroxyethyl)amino]-5-(p-toluenesulfonyloxy)isoquino[5,6,7-cd]indazole-6(2H)-one, m.p. 83°–85° C.;
2-[2-(hydroxy)ethyl]-5-(p-toluenesulfonyloxy)isoquino[5,6,7-cd]indazole-6(2H)-one.

EXAMPLE 7

5-chloro-2-methylisoquino[5,6,7-cd]indazole-6(2H)-one

A solution of methyl hydrazine (0.76M; 0.021 g) in pyridine (0.6 mL) is added dropwise over two min to a stirred solution of 9-chloro-6-fluoro benzo[g]isoquinoline-5,10-dione of Preparative Example 20 in pyridine (0.5 mL) cooled with an ice-bath. A yellow precipitate appears in the dark solution after 6 min. After 1.3 h the reaction mixture is reduced to half its volume by a gentle stream of nitrogen and quenched with ice (5 g). The pale yellow precipitate is collected by suction filtration and washed with ice-water (2×1 mL) and dried under vacuum. The yellow solid is purified by silica gel column chromatography (eluant: chloroform/methanol 96/4 v/v) to yield 5-chloro-2-methylisoquino[5,6,7-cd]indazole-6(2H)-one (0.033 g; 71% yield) as a yellow solid.

m.p.: 244°–245° C.
$^1$H-NMR (CDCl$_3$): 4.25 (s, 3H); 7.59 (dd, 2H); 7.92 (d, 1H); 8.84 (d, 1H); 9.55 (s, 1H).

EXAMPLE 8

Preparation of 2-(aminoalkyl)-5-chloroisoquino[5,6,7-cd]indazole-6(2H)ones

Using the procedure of Example 7 the following compounds are obtained by reaction of 9-chloro-6-fluorobenzo[g]isoquinoline-5,10-dione of Preparative Example 20 with a substituted hydrazine selected from the group of (2-N-tert-butoxycarbonylaminoethyl) hydrazine, N-[2-(dimethylamino)ethyl]hydrazine [J. Med. Chem., 7, 493, (1964)], N-[2-(diethylamino)ethyl]hydrazine [J. Med. Chem., 7, 493, (1964)], N-[2-[(2-hydroxyethylamino)ethyl]]hydrazine (J. Het. Chem., 26, 85, (1989)], N-[3-(dimethylamino)propyl]hydrazine [J. Het. Chem., 23, 1491, (1986)]N-(2-aminoethyl)hydrazine [J. Het. Chem., 23, 1491, (1986)], N-[2-(methylamino)ethyl]hydrazine, N-(2-hydroxyethyl)hydrazine, N-(3-aminopropyl) hydrazine [J. Het. Chem., 23, 1491, (1986)]:

2-[2-(N-tert-butoxycarbonylamino)ethyl)]-5-chloroisoquino [5,6,7-cd]indazole-6(2H)-one;

m.p.: 226°–228° C.
$^1$H-NMR (CDCl$_3$+CD$_3$OD): 1.30 (s, 9H); 3.58 (t, 2H); 4.63 (t, 2H); 7.54 (d, 1H); 7.70 (d, 1H); 7.90 (dd, 1H); 8.70 (d, 1H); 9.40 (s, 1H);

2-[2-(dimethylamino)ethyl]-5-chloroisoquino[5,6,7-cd]indazole-6(2H)-one;

m.p.: 160°–161° C. $^1$H-NMR (CDCl$_3$): 2.32 (s, 6H); 2.95 (t, 2H); 4.65 (t, 2H); 7.60 (d, 1H); 7.69 (d, 1H); 8.00 (dd, 1H); 8.88 (d, 1H); 9.60 (s, 1H);

2-[2-(diethylamino)ethyl]-5-chloroisoquino[5,6,7-cd] indazole-6(2H)-one;
2-[2-(diethylamino)ethyl]-5-chloroisoquino[5,6,7-cd] indazole-6(2H)-one 2-[2-[(2-hydroxyethyl)amino]ethyl]-5-chloroisoquino[5,6,7-cd]indazole-6(2H)-one;

m.p.: 148°–152.5° C.
$^1$H-NMR (CDCl$_3$+CD$_3$OD): 2.75 (t, 2H); 3.43 (t, 2H); 3.60 (t, 2H); 4.63 (t, 2H) 7.55 (d, 1H); 7.75 (d, 1H); 7.98 (dd, 1H); 8.73 (d, 1H); 9.40 (s, 1H);

2-[3-(dimethylamino)propyl]-5-chloroisoquino[5,6,7-cd] indazole-6(2H)-one;
2-[2-(amino)ethyl]-5-chloroisoquino[5,6,7-cd]indazole-6 (2H)-one;
2-[2-(methylamino)ethyl]-5-chloroisoquino[5,6,7-cd] indazole-6(2H)-one;
2-[2-(hydroxy)ethyl]-5-chloroisoquino[5,6,7-cd]indazole-6 (2H)-one;
2-[3-(amino)propyl]-5-chloroisoquino]5,6,7-cd]indazole-6 (2H)-one;

EXAMPLE 9

2-[2-(dimethylamino)ethyl)]-5-(p-toluenesulfonyloxy)isoquino[8,7,6-cd]indazole-6(2H)-one-9-oxide Under a nitrogen atmosphere a solution of N-[2-(dimethylamino)ethyl]hydrazine (0.805 g) in THF (10.75 mL) is added to a stirred suspension of 9-fluoro-6-(p-toluenesulfonyloxy)benzo[g]isoquinoline-5,10-dione-2-oxide of Preparative Example 21 (1.075 g) in THF (10.75 mL). After stirring for 2 h, the mixture is heated to 40° C. for 1 h. After cooling to room temperature the mixture is poured in water (150 mL) and the obtained suspension is stirred for 2 h. The precipitate is recovered by filtration and recrystallized from ethyl acetate/n-hexane to give 2-[2-(dimethylamino)ethyl)] -5-(p-toluenesulfonyloxy)isoquino[8,7,6-cd]indazole- 6(2H)-one-9-oxide (0.31 g).

m.p. 212°–214° C.

$^1$H-NMR (CDCl$_3$): 2.32 (s, 6H); 2.49 (s, 3H); 2.95 (t, 2H); 4.63 (t, 2H); 7.38 (d, 2H); 7.55 (d, 1H); 7.80 (d, 1H); 8.0 (d, 2H); 8.20 (m, 2H); 8.95 (d, 1H).

EXAMPLE 10

Following the procedure of Example 9 the following compounds are prepared by reaction of benzo[g]isoquinoline-5,10-dione-2-oxides of Preparative Example 21 and Preparative Example 22 with the properly selected substituted-hydrazines:

2-methyl]-5-(p-toluenesulfonyloxy)isoquino[8,7,6-cd]indazole-6(2H)-one-9-oxide;

2-[2-(N-tert-butoxycarbonylamino)ethyl]-5-(p-toluenesulfonyloxy)isoquino[8,7,6-cd]indazole-6(2H)-one-9-oxide;

2-[2-(dimethylamino)ethyl)]-5-(p-toluenesulfonyloxy)isoquino[5,6,7-cd]indazole-6(2H)-one-8-oxide;

2-[2-(N-tert-butoxycarbonylamino)ethyl]-5-(p-toluenesulfonyloxy)isoquino[5,6,7-cd]indazole-6(2H)-one-8-oxide;

2-[2-[(2-hydroxyethyl)amino]ethyl]-5-(p-toluenesulfonyloxy)isoquino[5,6,7-cd]indazole-6(2H)-one-8-oxide.

EXAMPLE 11

10-(p-Methoxybenzyloxy)-5-chloro-2-methylisoquino[5,6,7-cd]indazole-6(2H)-one

A solution of methyl hydrazine (0.015 g) in pyridine (0.6 mL) is added over a 2 minute period to a solution of 9-chloro-6-fluoro-4-(p-methoxy benzyloxy)benzo[g]isoquinoline-5,10-dione of Preparative Example 29 (0.055 g) in pyridine (0.5 mL) at 0° C. and the mixture is stirred for 1 h 20 min. The pyridine is removed by a slow nitrogen stream and the resultant residue is placed under vacuo for 2 h. The residue is purified by radial chromathography (2 mm silica gel plate) using gradient elution commencing with chloroform (100 mL), then 1% methanol/99% chloroform (75 mL) followed by 2% methanol/98% chloroform (175 mL). Upon removal of the last eluents 10-(p-methoxybenzyloxy)-5-chloro-2-methylisoquino[5,6,7-cd]indazole-6(2H)-one is obtained as a bright yellow solid (25 mg).

m.p. 181°–183° C.

$^1$H NMR (CDCl$_3$) δ9.28 (s, 1H), 8.62 (s, 1H), 7.66 (d, J$_{HH}$=8.3 Hz, 1H), 7.62 (d, J$_{HH}$=8.4 Hz, 2H), 7.57 (d, J$_{HH}$=8.3 Hz, 1H), 6.94 (d, J$_{HH}$=8.4 Hz, 2H), 5.44 (s, 2H), 4.31 (s, 3H), 3.83 (s, 3H). From the 1% methanol/99% chloroform fraction, starting material is recovered (10 mg).

EXAMPLE 12

5-chloro-2-[2-(dimethylamino)ethyl]-10-(p-methoxybenzyloxy)isoquino[5,6,7-cd]indazole-6(2H)-one A solution of N-[2-(dimethylamino)ethyl]hydrazine (8.5 mg) in pyridine (0.5 mL) is added to 9-chloro-6-fluoro-4-(p-methoxybenzyloxy) benzo[g]isoquinoline-5,10-dione of Preparative Example 29 (13 mg) over a period of 2 minutes at 0° C. under a nitrogen blanket and the mixture is stirred for 2 h. The excess pyridine and some excess hydrazine are removed under a nitrogen stream. The residue is placed under vacuum overnight. The product is purified by thick layer chromathography (silica gel, 10 cm by 20 cm) using 4% methanol/96% dicloromethane. The major yellow band is scraped from the plate and the yellow compound extracted into 25% methanol/75% dicloromethane. Removal of the solvent gives 5-chloro-2-[2-(dimethylamino)ethyl]-10-(p-methoxybenzyloxy) isoquino[5,6,7-cd]indazole-6(2H)-one (3 mg) as an amorphous solid.

EXAMPLE 13

Following the procedure of Example 12 the following compound is prepared by reaction of 9-chloro-6-fluoro-4-(p-methoxybenzyloxy)benzo[g]isoquinoline-5,10-dione of Preparative Example 29 with the properly selected hydrazine derivative:

2-[2-(tert-butoxycarbonylamino)ethyl]-5-chloro-10-(p-methoxybenzyloxy)isoquino [5,6,7-cd]indazole-6(2H)-one.

EXAMPLE 14

The following compounds are prepared by reaction of 6-fluoro-9-chlorobenzo[g]quinoline-5,10-dione or 6-chloro-9-fluorobenzo[g]quinoline-5,10-dione of Preparative Example 12 with the properly selected substituted-hydrazine:

2-methyl-5-chloroquino[8,7,6-cd]indazole-6(2H)-one;

2-methyl-5-chloroquino[5,6,7-cd]indazole-6(2H)-one;

2-[2-(dimethylamino)ethyl]-5-chloroquino[8,7,6-cd]indazole-6(2H)-one;

2-[2-(dimethylamino)ethyl]-5-chloroquino[5,6,7-cd]indazole-6(2H)-one;

EXAMPLE 15

The following compounds are prepared by reaction of 9-fluoro-6-(p-toluenesulfonyloxy)benzo[g]phthalazine-5,10-dione or 9-fluoro-6-(p-toluenesulfonyl oxy)benzo[g]quinoxaline-5,10-dione of Preparative Example 30 with the properly selected substituted-hydrazines:

2-[2-(dimethylamino)ethyl)]-5-(p-toluenesulfonyloxy)phthalazino[5,6,7-cd]indazole-6(2H)-one;

2-methyl-5-(p-toluenesulfonyloxy)phthalazino[5,6,7-cd]indazole-6(2H)-one;

2-[2-(dimethylamino)ethyl)]-5-(p-toluenesulfonyloxy)quinoxalino[5,6,7-cd]indazole-6(2H)-one;

2-methyl-5-(p-toluenesulfonyloxy)quinoxalino[5,6,7-cd]indazole-6(2H)-one;

EXAMPLE 16

Under a nitrogen atmosphere a solution of N-(terz-butoxy carbonyl)ethylenediamine (prepared according to Synt. Comm., 20, 2559, (1990); 0.327 g) in pyidine (0.40 mL) is added during 2 min to a suspension of 6,9-difluorobenzo[g] quinoline-5,10-dione of Preparative Example 12 (0.25 g) in pyridine (2.5 mL). After stirring at room temperature for 18 h the purple mixture is partitioned between water (50 mL) and ethyl acetate (100 mL). The organic layer is washed with water (50 mL), with brine (50 mL) and dried over sodium sulphate. Removal of the solvent left a purple residue which is purified by silica gel column chromatography with gradient elution with mixtures of dichloromethane/methyl-tert-butyl ether from 85/15 to 75/25 followed by mixtures of dichloromethane/ethyl acetate from 60/40 to 20/80.

6-[[2-(N-terz-butoxycarbonylamino)ethyl]amino]-9-fluorobenzo[g]quinoline-5,10-dione (0.115 g) and 9-[[2-(N-terz-butoxycarbonylamino)ethyl]amino]-6-fluoro benzo[g]quinoline-5,10-dione (0.173 g) are obtained as pure amorphous compounds.

EXAMPLE 17

9-chloro-6-[(2-dimethylaminoethyl)amino]-4-(p-methoxybenzyloxy)benzo[g]iso quinoline-5,10-dione A pyridine solution (0.4 mL) of N, N-dimethylethylenediamine (0.049 g) is added to 9-chloro-6-fluoro-4-(p-methoxybenzyloxy)benzo[g]isoquinoline-5,10-dione of Preparative Example 29 (0.011 g) and the resultant solution is stirred under a nitrogen atmosphere for 1.75 h at room temperature. The excess amine and pyridine are removed under a slow stream of nitrogen. The residue is placed under vacuun for 3 h and purified by silica gel column chromathography commencing with 1% to 2% methanol in dichloromethane. The removal of the eluents yields 9-chloro-6-[(2-dimethylaminoethyl)amino]-4-(p-methoxybenzyloxy)benzo[g]isoquinoline-5,10-dione as a purple solid (10 mg).

m.p. 127°–128° C.;

$^1$H NMR (CDCl$_3$) δ10.08 (m, 1H), 9.07 (s, 1H), 8.72 (s, 1H), 7.50 (m, 3H), 7.02 (d,J=9.4 Hz, 1H), 6.93 (d,J=8.6 Hz, 1H), 5.34 (s, 2H), 3.82 (s, 3H), 3.42 (q,J=6.3 Hz, 2H), 2.67 (t,J=6.3 Hz, 2H), 2.37 (s, 6H).

EXAMPLE 18

5-[[2-(dimethylamino)ethyl]amino]-2-methylisoquino[8,7,6-cd]indazole-6(2H)-one

A 1M solution of N,N-dimethylethylenediamine in pyridine (0.10 mL) is added to a stirred suspension of 2-methyl-5-(p-toluenesulfonyloxy)isoquino[8,7,6-cd]indazole-6(2H)-one of Example 1 (0.02 g) in dry pyridine (2 mL). After stirring at room temperature for one hour the reaction mixture is heated at 70° C. for 13 hours while additional amounts of N,N-dimethylethylenediamine solution (0.1; 0.05; 0.05 mL) are added after 2, 4 and 11 hours respectively. Pyridine and excess N,N-dimethylethylenediamine are removed by distillation at reduced pressure and the obtained residue is partitioned between CH$_2$Cl$_2$ (50 mL) and brine (10 mL) to which NaHCO$_3$ saturated solution is added (1 mL). The organic solution is dried over anhydrous Na$_2$SO$_4$ and the solvent removed by distillation. The orange residue obtained is purified by silica-gel column chromatography (eluant: CHCl$_3$/MeOH 95/5 (30 mL) followed by CHCl$_3$/MeOH/NH$_4$OH 90/15/0.5 (50 mL) to give 2-methyl-5-[[2-(dimethylamino)ethyl]amino]isoquino[8,7,6-cd]indazole-6(2H)-one (0.011 g) as a reddish orange solid.

m.p.: 208°–215° C.(dec.).

$^1$H-NMR (CDCl3): 2.40 (s, 3H); 2.75 (t, 2H); 3.57 (q, 2H); 4.25 (s, 3H); 6.97 (d, 1H); 7.63 (d, 1H); 8.30 (dd, 1H) 8.79 (d, 1H); 9.30 (br.t, 1H); 9.62 (d, 1H).

EXAMPLE 19

2-[2-(dimethylamino)ethyl]-5-[[2-(dimethylamino)ethyl]amino]isoquino[8,7,6-cd]indazole-6(2H)-one A solution of 2-[2-(dimethylamino)ethyl]-5-(p-toluenesulfonyloxy) isoquino[8,7,6-cd]indazole-6(2H)-one of Example 2 (0.463 g) and 2-(dimethylamino)ethylamine (0.80 mL) in dry pyridine (4.63 mL) is heated at 80° C. for 1 h, 30' under a nitrogen blanket. The solution is then concentrated to dryness and the dark residue obtained is partitioned between brine (30 mL) and ethyl acetate (4×25 mL). The combined organic solutions are dried over Na$_2$SO$_4$ and concentrated to about 3 mL. After addition of n-hexane (12 mL) and stirring for one hour the precipitate is collected by suction and dried at 40° C. under vacuum to give 2-[2-(dimethylamino)ethyl]5-[[2-(dimethylamino)ethyl]amino]isoquino[8,7,6-cd]indazole-6(2H)-one (0.23 g).

m.p.: 150°–152° C.

$^1$H-NMR (CDCl$_3$): 2.32 (s, 6H); 2.40 (s, 6H); 2.70 (t, 2H); 2.95 (t, 2H); 3.60 (q, 2H); 4.65 (t, 2H); 6.98 (d, 1H); 7.70 (d, 1H); 8.30 (d, 1H); 8.80 (d, 1H); 9.30 (br, 1H); 9.65 (s, 1H).

EXAMPLE 20

2-[2-(N-tert-butoxycarbonylamino)ethyl]-5-[[2-(N-tert-butoxycarbonylamino)ethyl]amino]isoquino[8,7,6-cd]indazole-6(2H)-one A suspension of 2-[2-(N-tert-butoxycarbonylamino)ethyl]-5-(p-toluenesulfonyl oxy)isoquino[8,7,6cd]indazole-6(2H)-one Example 3 (0.535 g) and N-(tert-butoxycarbonyl)ethylenediamine (1.12 g) in dry pyridine (5.35 mL) is heated at 80° C. The dark solution obtained is held at this temperature for 5 hours, then it is concentrated to dryness and partitioned between brine (30 mL) and ethyl acetate (2×25 mL). The orange-red solid insoluble in the biphasic mixture is separated by suction filtration and dried at 40° C. under vacuum (0.43 g).

This material (0.60 g) is purified by column chromatography (SiO$_2$; eluant methylene chloride/methanol from 90/10 to 70/30 v/v). The fractions containing the product are pooled and concentrated to about 20 mL and 2-[2-(N-tert-butoxycarbonylamino)ethyl]5-[[2-(N-tert-butoxycarbonylamino)ethyl]amino]isoquino[8,7,6-cd]indazole-6(2H)-one separates as red-orange crystals (0.45 g).

m.p.: 211°–213° C.

$^1$H-NMR (CDCl$_3$/DMSO-d$_6$9/1): 1.3 (s, 9H); 1.4 (s, 9H); 3.32 (q, 2H); 3.58 (m, 4H); 4.58 (t, 2H); 6.20 (br, 1H); 6.40 (br, 1H); 7.05 (d, 1H); 7.70 (d, 1H); 8.15 (d, 1H); 8.65 (d, 1H); 9.20 (br, 1H); 9.49 (s, 1H).

EXAMPLE 21

2-[2-(N-tert-butoxycarbonylamino)ethyl]-5-[[(2-(dimethylamino)ethyl]amino]isoquino[8,7,6-cd]indazole-6(2H)-one A suspension of 2-[2-(N-tert-butoxycarbonylamino)ethyl]-5-(p-toluene sulfonyloxy) isoquino[8,7,6-cd]indazole-6(2H)-one of Example 3 (0.056 g) and 2-dimethylamino)ethylamine (0.080 mL) in dry pyridine (0.50 mL) is heated at 80° C. The dark solution obtained is held at this temperature for 1 hour, then it is left at room temperature overnight. The dark precipitate obtained is separated by suction and purified by column chromatography (SiO$_2$; eluant ethyl acetate and then methylene chloride/methanol 9/0.5 v/v) to give 2-[2-(N-tert-butoxycarbonylamino)ethyl[-5-[[2-(dimethylamino)ethyl]amino]isoquino[8,7,6-cd]indazole-6(2H)-one (0.024 g) as a red-orange solid.

m.p.: 225°–227° C. (from methylene chloride).

$^1$H-NMR (CDCl$_3$): 1.43 (s, 9H); 2.40 (s, 6H); 2.7 (t, 2H); 3.55 (q, 2H); 3.78 (m, 2H); 4.65 (t, 2H); 5.23 (br.m, 1H); 6.87 (d, 1H); 7.62 (d, 1H); 8.28 (dd, 1H); 8.76 (d, 1H); 9.6 (s, 1H).

EXAMPLE 22 isoquino[8,7,6-cd]indazole-6(2H)-ones

Following the procedures of Examples 18–21, the following compounds are prepared by reaction of 2-[2-(dimethylamino)ethyl]-5-(p-toluenesulfonyl oxy)isoquino[8,7,6-cd]indazole-6(2H)-one of Example 2,2-[2-(N-tert-butoxycarbonylamino)ethyl]-5-(p-toluenesulfonyloxy)isoquino[8,7,6-cd]indazole-6(2H)-one of Example 3, or 2-[2-[(2-hydroxyethyl)amino]ethyl]-5-(p-toluenesulfonyloxy)isoquino[8,7,6-c]indazole-6(2H)-one of Example 4 with the properly selected amine:

2-[2-[(2-hydroxyethyl)amino]ethyl]-5-[[2-[(2-hydroxyethyl)amino]ethyl]amino]isoquino[8,7,6-cd]indazole-6(2H)-one;

$^1$H-NMR (CDCl$_3$): 3.25 (m, 6H); 3.61 (t, 4H); 3.71 (m, 4H); 3.98 (q, 2H); 4.65 (t, 2H); 5.31 (br, 2H); 7.08 (d, 1H); 7.70 (d, 1H); 8.30 (d, 1H); 8.83 (d, 1H); 9.30 (br, 1H); 9.69 (s, 1H).

2-[2-[(2-hydroxyethyl)amino]ethyl]-5-[[3-(amino)propyl]amino]isoquino]8,7,6-cd]indazole-6(2H)-one;

$^1$H-NMR (CDCl$_3$): 2.05 (m, 2H); 3.18 (m, 4H); 3.58 (t, 2H); 3.65 (t, 2H); 3.78 (q, 2H); 4.62 (t, 2H); 5.20 (br, 3H); 7.10 (d, 1H); 7.69 (d, 1H); 8.30 (d, 1H); 8.85 (d, 1H); 9.15 (br, 1H); 9.30 (t, 1H); 9.71 (s, 1H).

2-[2-[(2-hydroxyethyl)amino]ethyl]-5-[[2-(amino)ethyl]amino]isoquino [8,7,6-cd]indazole-6-(2H)-one;

$^1$H-NMR (CDCl$_3$): 3.20 (m, 4H), 3.58 (t, 2H); 3.66 (t, 2H); 3.86 (q, 2H); 4.61 (t, 2H); 5.15 (br, 3H); 7.12 (d, 1H); 7.69 (d, 1H); 8.30 (d, 1H); 8.85 (d, 1H); 9.15 (br, 1H); 9.30 (t, 1H); 9.71 (s, 1H).

2-[2-[(2-hydroxyethyl)amino]ethyl]-5-[[2-(methylamino)ethyl]amino]isoquino[8,7,6-cd]indazole-6(2H)-one;

$^1$H-NMR (CDCl$_3$): 2.61 (s, 3H); 3.06 (t, 2H); 3.20 (t, 2H); 3.58 (t, 2H); 3.67 (t, 2H); 3.88 (q, 2H); 4.65 (t, 2H); 5.10 (t, 1H); 7.05 (d, 1H); 7.70 (d, 1H); 8.33 (d, 1H); 8.81 (d, 1H); 8.99 (br, 2H); 9.35 (t, 1H); 9.66 (s, 1H).

2-[2-[(2-hydroxyethylamino]ethyl]-5-[[2-(dimethylamino)ethyl]amino]isoquino [8,7,6-cd]indazole-6(2H)-one;

$^1$H-NMR (CDCl$_3$): 2.42 (s, 6H); 2.75 (t, 2H); 3.18 (t, 2H); 3.58 (q, 2H); 3.63 (t, 2H); 3.68 (t, 2H); 4.61 (t, 2H); 5.15 (t, 1H); 6.99 (d, 1H); 7.66 (d, 1H); 8.31 (d, 1H); 8.80 (d, 1H); 9.11 (br, 1H); 9.35 (t, 1H), 9.65 (s, 1H).

2-[2-[(2-hydroxyethyl)amino]ethyl]-5-[[2-(N-tert-butoxycarbonylamino) ethyl]amino]isoquino[8,7,6-cd]indazole-6 (2H)-one;

$^1$H-NMR (CDCl$_3$+CD$_3$OD): 1.40 (s, 9H); 3.31 (m, 4H); 3.52 (q, 2H); 3.63 (t, 2H); 3.85 (t, 2H); 4.71 (t, 2H); 7.03 (d, 1H); 7.70 (d, 1H); 8.21 (dd, 1H); 8.76 (d, 1H); 9.61 (s, 1H).

2-[2-(N-tert-butoxycarbonylamino)ethyl)]-5-[[2-[(2-hydroxyethyl)amino]ethyl]amino]isoquino[8,7,6-cd]indazole-6(2H)-one;

$^1$H-NMR (CDCl$_3$): 1.45 (s, 9H); 2.95 (t, 2H); 3.14 (t, 2H); 3.60 (q, 2H); 3.80 (m, 4H); 4.63 (t, 2H); 5.40 (m, 1H, exchangeable with D$_2$O); 6.85 (d, 1H); 7.58 (d, 1H); 8.15 (dd, 1H); 8.65 (d, 1H); 9.42 (br. t, 1H, exchangeable with D$_2$O); 9.52 (s, 1H);

2-[2-(dimethylamino)ethyl]-5-[[2-[(2-hydroxyethyl)amino]ethyl]amino]isoquino [8,7,6-cd]indazole-6(2H)-one;

m.p.: 156°–157° C.

$^1$H-NMR (CDCl$_3$): 2.30 (s, 6H); 2.91 (m, 4H); 3.08 (t, 2H); 3.60 (t, 2H); 3.75 (m, 2H); 4.60 (t, 2H); 6.90 (d, 1H); 7.60 (d, 1H); 8.25 (dd, 1H); 8.75 (d, 1H); 9.45 (br, 1H); 9.60 (s, 1H).

2-[2-(dimethylamino)ethyl]-5-[[2-(amino)ethyl]amino]isoquino[8,7,6-cd]indazole-6(2H)-one;

$^1$H-NMR (CDCl$_3$+CD$_3$OD): 2.30 (s, 6H); 2.95 (t, 2H); 3.13 (t, 2H); 3.65 (t, 2H); 4.58 (t, 2H); 7.04 (d, 1H); 7.70 (d, 1H); 8.18 (dd, 1H); 8.66 (d, 1H); 9.51 (s, 1H).

2-[2-(N-tert-butoxycarbonylamino)ethyl)]-5-[[2-(N-tert-butoxycarbonyl-N-methylamino)ethyl]amino]isoquino[8,7,6-cd]indazole-6(2H)-one;

$^1$H-NMR (CDCl$_3$): 1.45 (s, 9H); 1.49 (s, 9H); 2.97 (s, 3H); 3.68 (m, 6H); 4.64 (t, 2H); 5.19 (br., 1H); 7.05 (m, 1H); 7.68 (d, 1H); 8.22 (d, 1H); 8.75 (d, 1H); 9.25 (t, 1H); 9.60 (s, 1H).

2-[2-(dimethylamino)ethyl]-5-[[2-(hydroxy)ethyl]amino] isoquino[8,7,6-cd]indazole-6(2H)-one;

2-[2-[(2-hydroxyethyl)amino]ethyl]-5-[[2-(N-tert-butoxycarbonyl-N-methylamino)ethyl]amino]isoquino[8,7,6-cd]indazole-6(2H)-one;

$^1$H-NMR (CDCl$_3$): 1.49 (s, 9H); 2.85 (t, 2H); 2.94 (s, 3H); 3.30 (t, 2H); 3.61 (m, 2H); 4.66 (t, 2H); 7.09 (m, 1H); 7.70 (d, 1H); 8.27 (d, 1H); 8.80 (d, 1H); 9.29 (t, 1H); 9.64 (s, 1H).

2-[2-(dimethylamino)ethyl]-5-[[3-(dimethylamino)propyl]amino]isoquino[8,7,6-cd]indazole-6(2H)-one;

$^1$H-NMR (CDCl$_3$): 1.98 (m, 2H); 2.28 (s, 6H); 2.33 (s, 6H); 2.48 (t, 2H); 2.93 (t, 2H); 3.58 (q, 2H); 4.65 (t, 2H); 7.08 (d, 1H); 7.72 (d, 1H); 8.31 (d, 1H); 8.80 (d, 1H); 9.29 (t, 1H); 9.69 (s, 1H).

2-[2-(dimethylamino)ethyl]-5-[[2-(4'-morpholinyl)ethyl]amino]isoquino[8,7,6-cd]indazole-6(2H)-one;

$^1$H-NMR (CDCl$_3$): 2.35 (s, 6H); 2.60 (m, 4H); 2.80 (t, 2H); 2.95 (t, 2H); 3.61 (q, 2H); 3.83 (m, 4H); 4.65 (t, 2H); 7.01 (d, 1H); 7.74 (d, 1H); 8.34 (d, 1H); 8.81 (d, 1H); 9.37 (t, 1H); 9.67 (s, 1H).

2-[2-(dimethylamino)ethyl]-5-[[2-(diethylamino)ethyl]amino]isoquino[8,7,6-cd]indazole-6(2H)-one;

$^1$H-NMR (CDCl$_3$): 1.12 (t, 6H); 2.35 (s, 6H); 2.67 (q, 4H); 2.86 (t, 2H); 2.95 (t, 2H); 3.56 (q, 2H); 4.64 (t, 2H); 7.02 (d, 1H); 7.74 (d, 1H); 8.34 (d, 1H); 8.80 (d, 1H); 9.33 (br., 1H); 9.67 (s, 1H).

2-[2-(dimethylamino)ethyl]-5-[[2-(methylamino)ethyl]
amino]isoquino[8,7,6-cd]indazole-6(2H)-one;

¹H-NMR (CDCl₃): 2.32 (s, 6H); 2.56 (s, 3H); 2.92 (t, 2H); 3.02 (t, 2H); 3.62 (q, 2H); 4.61 (t, 2H); 7.01 (d, 1H); 7.70 (d, 1H); 8.28 (d, 1H); 8.78 (d, 1H); 9.35 (t, 1H); 9.64 (s, 1H).

2-[2-(dimethylamino)ethyl]-5-[[3-(amino)propyl]amino]
isoquino[8,7,6-cd]indazole-6(2H)-one;

¹H-NMR (CDCl₃): 1.86 (m, 2H); 2.34 (s, 6H); 2.96 (m, 4H); 3.61 (q, 2H); 4.65 (t, 2H); 7.05 (d, 1H); 7.74 (d, 1H); 8.31 (d, 1H); 8.81 (d, 1H); 9.34 (t, 1H); 9.69 (s, 1H).

2-[2-(hydroxy)ethyl]-5-[[2-(dimethylamino)ethyl]amino]
isoquino[8,7,6-cd]indazole-6(2H)-one;
2-[2-(hydroxy)ethyl]-5-[[2-(N-tert-butoxycarbonylamino)ethyl]amino]isoquino[8,7,6-cd]indazole-6(2H)-one;

m.p. 178°–180° C.;

2-[2-(hydroxy)ethyl]-5-[[2-(amino)ethyl]amino]isoquino[8,7,6-cd]indazole-6(2H)-one;
2-[3-(dimethylamino)propyl]-5-[[2-(dimethylamino)ethyl]amino]isoquino[8,7,6-cd]indazole-6(2H)-one;
2-[2-(dimethylamino)ethyl]-5-[[2-(1'-imidazolyl)ethyl]amino]isoquino[8,7,6-cd]indazole-6(2H)-one;
2-[2-(dimethylamino)ethyl]-5-[[2-[N-bis(2-hydroxyethyl)amino]ethyl]amino]isoquino[8,7,6-cd]indazole-6(2H)-one;
2-[2-(N-terz-butoxycarbonylamino)ethyl]-5-[[2-[N-bis(2-hydroxyethyl)amino]ethyl]amino]isoquino[8,7,6-cd]indazole-6(2H)-one;
2-[2-(dimethylamino)ethyl]-5-[[2-(1'-piperidinyl)ethyl]amino]isoquino[8,7,6-cd]indazole-6(2H)-one;
2-[2-(dimethylamino)ethyl]-5-[[2-(1'-piperazinyl)ethyl]amino]isoquino[8,7,6-cd]indazole-6(2H)-one;
2-[2-(N-terz-butoxycarbonylamino)ethyl]-5-[[2-(diethylamino)ethyl]amino]isoquino[8,7,6-cd]indazole-6(2H)-one;
2-[2-(N-terz-butoxycarbonylamino)ethyl]-5-[[2-(4'-morpholinyl)ethyl]amino]isoquino[8,7,6-cd]indazole-6(2H)-one.

EXAMPLE 23

5-[[2-(dimethylamino)ethyl]amino]-2-methylisoquino[5,6,7-cd]indazole-6(2H)-one 5-chloro-2-methylisoquino[5,6,7-cd]indazole-6 (2H)-one of Example 7 (0.013 g) is added to 2-(dimethylamino)ethylamine (0.34 mL). The yellow mixture is heated quickly to reflux for 1 hour. The excess diamine is removed from the orange solution by a gentle stream of nitrogen. The orange mixture obtained is purified by silica gel column chromatography with a gradient elution (1% methanol/chloroform (25 mL), 2% methanol/chloroform (25 mL), 4% methanol/chloroform (25 mL), 8% methanol/chloroform (25 mL), 12% methanol/chloroform (25 mL), 16% methanol/chloroform (25 mL), 24% methanol/chloroform (50 mL)) to yield 5-[[2-(dimethylamino)ethyl]amino]-2-methylisoquino[5,6,7-cd]indazole-6(2H)-one (0.010 g) as a reddish orange solid.
m.p.: 212°–216° C.

¹H-NMR (CDCl₃): 2.36 (s, 6H); 2.69 (t, 2H); 3.54 (q, 2H); 4.21 (s, 3H); 6.91 (d, 1H); 7.54 (d, 1H); 8.00 (d, 1H); 8.79 (d, 1H); 9.19 (br, 1H); 9.67 (s, 1H).

EXAMPLE 24

2-[2-(dimethylamino)ethyl)]-5-[[2-(dimethylamino)ethyl]amino]isoquino[5,6,7-cd]indazole-6(2H)-one Under a nitrogen atmosphere N,N-dimethylethylenediamine (1.79 mL) is added to a stirred solution of 2-[2-(dimethylamino)ethyl]-5-chloroisoquino[5,6,7-cd]indazole-6(2H)-one of Example 8 (0.539 g) in pyridine (6.80 mL) and the resulting solution is heated at 80° C. for 12 hours. The pyridine and excess N,N-dimethylethylenediamine are removed by roto-evaporation and the obtained residue is purified by silica gel column chromatography eluting first with methylene chloride, then with methylene chloride/methanol 95/5 and finally with methylene chloride/methanol/concd. ammonia from 95/5/0.5 to 95/5/1 v/v/v. The fractions containing the yellow desired product are pooled and the solvents roto-evaporated. The obtained residue (0.529 g) is crystallized from diisopropylether to give 2-[2-(dimethylamino)ethyl)]-5-[[2-(dimethylamino)ethyl]amino]isoquino[5,6,7-cd]indazole-6(2H)-one as a yellow powder (0.291 g).

m.p.: 110°–111° C.

¹H-NMR (CDCl₃): 2.31 (s, 6H); 2.38 (s, 6H); 2.71 (t, 2H); 2.92 (t, 2H); 3.55 (q, 2H); 4.65 (t, 2H); 7.01 (d, 1H); 7.69 (d, 1H); 8.10 (dd, 1H); 8.83 (d, 1H); 9.30 (br.t., 1H); 9.71 (s, 1H).

EXAMPLE 25 isoquino[5,6,7-cd]indazole-6(2H)-ones

Using the procedures of Example 23 or 24, the following compounds are prepared by reaction of 2-[2-(N-tert-butoxycarbonylamino)ethyl]-5-chloroisoquino [5,6,7-cd]indazole-6(2H)-one, 2-[2-(dimethylamino)ethyl]-5-chloroisoquino[5,6,7-cd]indazole-6(2H)-one, or 2-[2-[(2-hydroxyethyl)amino]ethyl]-5-chloroisoquino [5,6,7-cd]indazole-6(2H)-one of Example 8:

2-[2-(N-tert-butoxycarbonylamino)ethyl-5-[[2-(N-tert-butoxycarbonylamino) ethyl]amino]isoquino[5,6,7-cd]indazole-6(2H)-one;

m.p.: 211°–213° C.
¹H-NMR (CDCl₃): 1.40 (s, 9H); 1.46 (s, 9H); 3.55 (q, 2H); 3.65 (q, 2H); 3.77 (q, 2H); 4.69 (t, 2H); 5.55 (br, 2H); 7.00 (d, 1H); 7.60 (d, 1H); 7.93 (dd, 1H); 8.70 (d, 1H); 9.10 (br.t., 1H); 9.38 (s, 1H).

2-[2-(N-tert-butoxycarbonylamino)ethyl]-5-[[2-(amino)ethyl]amino]isoquino[5,6,7-cd]indazole-6(2H)-one; (reaction performed at 50° C. in DMSO as the solvent)

m.p.: 221°–222° C.
¹H-NMR (CDCl₃): 1.43 (s, 9H); 3.13 (t, 2H); 3.58 (q, 2H); 3.75 (q, 2H); 3.67 (t, 2H); 5.05 (br, 1H); 7.00 (d, 1H); 7.65 (d, 1H); 8.05 (dd, 1H); 8.60 (d, 1H); 9.30 (br., 1H); 9.75 (s, 1H).

2-[2-(N-tert-butoxycarbonylamino)ethyl)]-5-[[2-[(2-hydroxyethyl)amino]ethyl]amino]isoquino[5,6,7-cd]indazole-6(2H)-one;

¹H-NMR (CDCl₃+CD₃OD): 1.48 (s, 9H); 3.25 (m, 4H); 3.74 (q, 2H); 3.80 (m, 4H); 4.68 (t, 2H); 7.01 (d, 1H); 7.72 (d, 1H); 8.09 (dd, 1H); 8.80 (d, 1H); 9.75 (s, 1H).

2-[2-(N-tert-butoxycarbonylamino)ethyl)]-5-[[2-(dimethylamino)ethyl]amino]isoquino[5,6,7-cd]indazole-6(2H)-one;

¹H-NMR (CDCl₃): 1.44 (s, 9H); 2.31 (s, 6H); 2.75 (t, 2H); 3.68 (q, 2H); 3.75 (q, 2H); 4.68 (t, 2H); 5.10 (br.m.,H); 7.03 (d, 1H); 7.70 (d, 1H); 8.15 (dd, 1H); 8.85 (d, 1H); 9.33 (br.t., 1H); 9.71 (s, 1H).

2-[2-(dimethylamino)ethyl]-5-[[2-[2-hydroxyethyl)amino]ethyl]amino]isoquino[5,6,7-cd]indazole-6(2H)-one;

¹H-NMR (CDCl₃+CD₃OD): 2.40 (s, 6H); 2.95 (t, 2H); 3.23 (m, 4H); 3.82 (m, 4H); 4.70 (t, 2H); 7.05 (d, 1H); 7.70 (d, 1H); 8.13 (dd, 1H); 8.85 (d, 1H); 9.70 (s, 1H).

2-[2-(dimethylamino)ethyl]-5-[[2-(amino)ethyl]amino]isoquino[5,6,7-cd]indazole-6(2H)-one;

¹H-NMR (CDCl₃): 2.39 (s, 6H); 2.95 (t, 2H); 3.15 (t, 2H); 3.68 (q, 2H); 4.68 (t, 2H); 7.00 (d, 1H); 7.65 (d, 1H); 8.12 (dd, 1H); 8.85 (d, 1H); 9.33 (br.t., 1H); 9.72 (s, 1H).

2-[2-[(2-hydroxyethyl)amino]ethyl]-5-[[2[(2-hydroxyethyl)amino]ethyl]amino]isoquino[5,6,7-cd]indazole-6(2H)-one; (reaction performed at 52° C. in DMSO as solvent)

m.p.: 148°–151° C.
¹H-NMR (D₂O): 2.75 (m, 6H); 2.95 (m, 2H); 3.12 (m, 2H); 3.70 (m, 4H); 4.05 (m, 2H); 6.10 (d, 1H); 6.65 (d, 1H); 6.90 (d, 1H); 7.83 (s, 1H); 7.95 (d, 1H).

2-[2-[(2-hydroxyethyl)amino]ethyl]-5-[[2-(amino)ethyl]amino]isoquino[5,6,7-cd]indazole-6(2H)-one;

¹H-NMR (CDCl₃+CD₃OD): 2.97 (t, 2H); 3.30 (m, 4H); 3.68 (t, 2H); 3.85 (t, 2H); 4.66 (t, 2H); 7.00 (d, 1H); 7.69 (d, 1H); 8.10 (dd, 1H); 8.83 (d, 1H); 9.76 (s, 1H).

2-[2-[(2-hydroxyethyl)amino]ethyl]-5-[[3-(amino)propyl]amino]isoquino[5,6,7-cd]indazole-6(2H)-one;
¹H-NMR (CDCl₃+CD₃OD): 2.09 (m, 2H); 2.57 (t, 2H); 3.30 (m, 4H); 3.53 (t, 2H); 3.82 (t, 2H); 4.66 (t, 2H); 7.01 (d, 1H); 7.68 (d, 1H); 8.05 (dd, 1H); 8.80 (d, 1H); 9.68 (s, 1H).

2-[2-[(2-hydroxyethyl)amino]ethyl]-5-[[2-(methylamino)ethyl]amino]isoquino[5,6,7-cd]indazole-6(2H)-one;

¹H-NMR (CDCl₃+CD₃OD): 2.48 (s, 3H); 2.83 (t, 2H); 3.28 (m, 4H); 3.58 (t, 2H); 3.83 (t, 2H); 4.67 (t, 2H); 7.01 (d, 1H); 7.68 (d, 1H); 8.03 (dd, 1H); 8.80 (d, 1H); 9.67 (s, 1H).

2-[2-[(2-hydroxyethyl)amino]ethyl]-5-[[2-(dimethyamino)ethyl]amino]isoquino[5,6,7-cd]indazole-6(2H)-one;

¹H-NMR (CDCl₃+CD₃OD): 2.31 (s, 6H); 2.72 (t, 2H); 3.33 (m, 4H); 3.57 (t, 2H); 3.87 (t, 2H); 4.71 (t, 2H); 7.00 (d, 1H); 7.71 (d, 1H); 8.09 (dd, 1H); 8.81 (d, 1H); 9.70 (s, 1H).

2-[2-[(2-hydroxyethyl)amino]ethyl]-5-[[2-(N-tert-butoxycarbonylamino)ethyl]amino]isoquino[5,6,7-cd]indazole-6(2H)-one;

¹H-NMR (CDCl₃+CD₃OD): 1.41 (s, 9H); 3.29 (m, 4H); 3.56 (t, 2H); 3.79 (t, 2H); 3.83 (t, 2H); 4.68 (t, 2H); 7.05 (d, 1H); 7.68 (d, 1H); 8.08 (dd, 1H); 8.80 (d, 1H); 9.68 (s, 1H).

EXAMPLE 26

2-[2-(dimethylamino)ethyl)]-5-[[2-(dimethylamino)ethyl]amino]isoquino[8,7,6-cd]indazole-6(2H)-one-9-oxide A mixture of 2-[2-(dimethylamino)ethyl)]-5-(p-toluenesulfonyloxy)isoquino[8,7,6-cd]indazole-6(2H)-one-9-oxide of Example 9 (0.05 g) and N,N-dimethylethylenediamine (0.115 mL) in dry pyridine (0.5 mL) is stirred at room temperature for 6 days and then it is heated to 70° C. for 3 h. After cooling to room temperature the mixture is partitioned between dichloromethane (23 mL) and water (10 mL). The organic layer is separated and the aqueous phase is furtherly extracted with dichloromethane (2×10 mL). The combined organic solutions are washed with a saturated solution of sodium chloride (20 mL) and dried over sodium sulphate. Removal of the solvent yields a residue which is purified by silica gel column chromatography, eluting with mixtures of dichloromethane/methanol/concd. ammonium hydroxide from 95/5/0.2 (150 mL) to 92.5/7.5/0.3 (300 mL) to 90/10/0.4 (100 mL).

2-[2-(dimethylamino)ethyl)]-5-[[2-(dimethylamino)ethyl]amino]isoquino[8,7,6-cd]indazole-6(2H)-one-9-oxide (0.017 g) is obtained as a red-brick solid.

m.p. 175°–176° C. (from tert-butyl methyl ether).

EXAMPLE 27

Following the procedure of Example 26 the following compounds are prepared by reaction of isoquinoindazole-N-oxides of Example 10 with the properly selected amines.

2-methyl-5-[[2-(dimethylamino)ethyl]amino]isoquino[8,7,6-cd]indazole-6(2H)-one-9-oxide;
2-[2-(N-tert-butoxycarbonylamino)ethyl]-5-[[2-(dimethylamino)ethyl]amino]isoquino[8,7,6-cd]indazole-6(2H)-one-9-oxide;
2-[2-(N-tert-butoxycarbonylamino)ethyl]-5-[(2-aminoethyl)amino]isoquino]8,7,6-cd]indazole-6(2H)-one-9-oxide;
2-[2-(N-tert-butoxycarbonylamino)ethyl]-5-[[2-(dimethylamino)ethyl]amino]isoquino[8,7,6-cd]indazole-6(2H)-one-9-oxide;
2-[2-(N-tert-butoxycarbonylamino)ethyl]-5-[[2-(dimethylamino)ethyl]amino]isoquino[5,6,7-cd]indazole-6(2H)-one-8-oxide
2-[2-(dimethylamino)ethyl)]-5-[[2-(amino)ethyl]amino]isoquino[8,7,6-cd]indazole-6(2H)-one-9-oxide
2-[2-(dimethylamino)ethyl]-5-[[2-(dimethylamino)ethyl]amino]isoquino[5,6,7-cd]indazole-6(2H)-one-8-oxide.

EXAMPLE 28

10-p-Methoxybenzyloxy-5-[[2-(dimethylamino)ethyl]amino]-2-methylisoquino[5,6,7-cd]indazole-6(2H)-one A solution of 10-(p-methoxybenzyloxy)-5-chloro-2-methylisoquino[5,6,7-cd]indazole-6(2H)-one of Example 11 (0.053 g) and N,N-dimethylethylenediamine (0,115 g) in pyridine (0.5 mL) is heated at 120° C. for 3.5 h under a nitrogen atmosphere. The excess diamine and pyridine are removed by a slow stream of nitrogen gas and the resultant dark orange residue is placed under vacuo for 3 h. The crude material is purified by radial chromathography (silica gel, 2 mm thickness) using gradient elution commencing with 2% methanol/98% chloroform (100 mL) to mixtures containing 4% methanol (75 mL) to 6% methanol (60 mL). Upon removal of the 4% methanol (96% chloroform eluent, starting material is recovered (10 mg). Removal of the 6% methanol/94% chloroform eluent led to 10-p-methoxybenzyloxy-5-[[2-(dimethylamino)ethyl]amino]-2-methylisoquino[5,6,7-cd]indazole-6(2H)-one as a pure product (22 mg).

m.p.=231°–232° C.;

$^1$H NMR (CDCl$_3$) δ9.42 (s, 1H), 9.35 (t, 1H), 8.55 (s, 1H), 7.66 (d, $J_{HH}$=9.1 Hz, 1H), 7.61 (d, $J_{HH}$=8.5 Hz, 2H), 7.0 (d, $J_{HH}$=9.1 Hz, 1H), 6.93 (d, $J_{HH}$=8.5 Hz, 2H), 5.45 (s, 2H), 4.31 (s, 3H), 3.82 (s, 3H), 3.56 (q, $J_{HH}$=6.5 Hz, $J_{HH}$ 6.2 Hz, 2H), 2.71 (t, $J_{HH}$=6.5 Hz, 2H), 2.37 (s, 6H).

EXAMPLE 29

Using the procedure of Example 28 the following compounds are prepared by reaction of 2-(substituted)-5-chloro-10-(p-methoxybenzyloxy) isoquino[5,6,7-cd]indazole-6(2H)-ones of Example 12 or Example 13 with the appropriate amine:

2-[2-(dimethylamino)ethyl]-5-[[2-(dimethylamino)ethyl]amino]-10-(p-methoxybenzyloxy)isoquino[5,6,7-cd]indazole-6(2H)-one;

2-[2-(dimethylamino)ethyl]-5-[[2-(amino)ethyl]amino]-10-(p-methoxybenzyloxy)isoquino[5,6,7-cd]indazole-6(2H)-one;

2-[2-(tert-butoxycarbonylamino)ethyl]-5-[[2-(tert-butoxycarbonylamino)ethyl]amino]-10-(p-methoxybenzyloxy)isoquino[5,6,7-cd]indazole-6(2H)-one.

EXAMPLE 30

2-(substituted)-5-[(substituted-alkyl)amino]phthalazino[5,6,7-cd]indazole-6-(2H)-ones The following compounds are obtained from the reaction of 2-[2-(dimethylamino)ethyl)]-5-(p-toluenesulfonyloxy)phthalazino[5,6,7-cd]indazole-6(2H)-one or 2-methyl-5-(p-toluenesulfonyloxy)phthalazino[5,6,7-cd]indazole-6(2H)-one of Example 15 with N,N-dimethylethylenediamine:

2-methyl-5-[[2-(dimethylamino)ethyl]amino]phthalazino[5,6,7-cd]indazole-6(2H)-one 2-[2-(dimethylamino)ethyl]-5-[[2-(dimethylamino)ethyl]amino]phthalazino[5,6,7-cd]indazole-6(2H)-one

EXAMPLE 31

2-(substituted)-5-[(substituted-alkyl)amino]quinoxalino[5,6,7-cd]indazole-6(2H)-ones The following compounds are obtained from the reaction of 2-[2-(dimethylamino)ethyl)]-5-(p-toluenesulfonyloxy)quinoxalino[5,6,7-cd]indazole-6(2H)-one or 2-methyl-5-(p-toluenesulfonyloxy)quinoxalino[5,6,7-cd]indazole-6(2H)-one of Example 15 with N,N-dimethylethylenediamine:

2-methyl-5-[[2-(dimethylamino)ethyl]amino]quinoxalino[5,6,7-cd]indazole-6(2H)-one 2-[2-(dimethylamino)ethyl]-5-[[2-(dimethylamino)ethyl]amino]quinoxalino[5,6,7-cd]indazole-6(2H)-one.

EXAMPLE 32

2-(substituted)-5-[(substituted-alkyl)amino]quinoindazole-6-(2H)-ones

The following compounds are obtained from the reaction of 2-substituted-5-chloroquinoindazoles of Example 14 with the properly selected amines:

2-methyl-5-[[2-(dimethylamino)ethyl]amino]quino[5,6,7-cd]indazole-6(2H)-one;

2-methyl-5-[[2(dimethylamino)ethyl]amino]quino[8,7,6-cd]indazole-6(2H)-one;

2-[2-(dimethylamino)ethyl]-5-[[2-(dimethylamino)ethyl]amino]quino[8,7,6-cd]indazole-6(2H)-one;

2-[2-(dimethylamino)ethyl]-5-[[2-(dimethylamino)ethyl]amino]quino[5,6,7-cd]indazole-6(2H)-one;

EXAMPLE 33

Under a nitrogen atmosphere a solution of N-[2(-dimethylamino) ethyl]hydrazine (40 mg) in dry pyridine (0.2 mL) is added to a solution of 9-[[2-(N-terz-butoxycarbonylamino)ethyl]amino]-6-fluoro benzo[g]quinoline-5,10-dione of Example 16 (50 mg) in pyridine (0.70 mL). After stirring for 5 h at room temperature the mixture is partitioned between dichloromethane (20 mL) and water (20 mL). The organic layer is separated and washed with water (2×30 mL), the water washings are re-extracted with dichloromethane (5 mL) and the combined organic solutions are dried over sodium sulphate.

After concentration to small volume (1 mL) the dichloromethane solution is applied to the top of a silica gel chromatographic column. Gradient elution with mixtures of dichloromethane/methanol/concd. ammonium hydroxide from 95/5/0.2 (100 mL) to 90/10/0.4(100 mL) to 88/12/0.5 (100 mL) yields a first fraction which is subjected to a second silica gel chromathographic purification by gradient elution with mixtures of 1,2-dimethoxyethane/concd. ammonium hydroxide from 100/0.2 to 100/0.7.

Removal of the eluates containing the slower-moving red orange band leaves a brown oil which is partitioned between dichloromethane (7 mL) and water (7 mL). The organic solution is washed with water (2×7 mL) and dried over sodium sulfate. Removal of the solvent yields 2-[2-(dimethylamino)ethyl]-5-[[2 -(N-terz-butoxy carbonylamino)ethyl]amino]quino[5,6,7-cd]indazole-6(2H)-one as a red-orange amorphous solid (3 mg).

$^1$H-NMR (CDCl$_3$-TMS): 1.45(s,9H); 2.35(s,6H); 3.05(t, 2H); 3.48(m, 2H); 3.68(m, 2H); 4.68(t, 2H); 5.10(br.t, 1H); 7.10(d, 1H); 7.50(m, 1H); 7.70(d, 1H); 8.75(d, 1H); 8.95(m, 2H); 9.20(br.t, 1H).

EXAMPLE 34

Repetition of the procedure of Example 33 and using 6-[[2-(N-terz-butoxycarbonylamino) ethyl]amino]-9-fluorobenzo[g]quinoline-5,10-dione of Example 16 as starting material in the reaction with N-[2-(dimethylamino) ethyl] hydrazine gives 2-[2-(dimethylamino)ethyl]-5-[[2-(N-terzbutoxycarbonyl amino)ethyl]amino]quino[8,7,6-cd]indazole-6(2H)-one.

EXAMPLE 35

Removal of the t-butoxycarbonyl protective group

Under a nitrogen atmosphere an ethanolic solution of anhydrous HCl (5N; 0.40 mL) is dropped into a stirred suspension of 2-[2-(N-tert-butoxycarbonylamino) ethyl]-5-[[2-(N-tert-butoxycarbonylamino) ethyl]amino]isoquino[8,7,6-cd]indazole-6(2H)-one of Example 20 (0.104 g) in absolute ethanol (2.1 mL). Initial dissolution of the starting material followed by precipitation of a dark-red solid is observed during the addition of ethanolic HCl. This solid is redissolved with absolute ethanol and the solution is heated to 40° C. for 2 h, 30'. The gradual formation of a redamaranth precipitate is observed during the heating. After cooling to room temperature diethyl ether (10 mL) is added and the precipitate is collected by suction filtration under a nitrogen blanket, to give 2-[2-(amino)ethyl]-5-[[2-(amino)ethyl]amino]isoquino[8,7,6-cd]indazole-6(2H)-one trihydrochloride (0.070 g).

m.p.: 247°–250° C.

$^1$H-NMR (D$_2$O): 3.40(t, 2H); 3.70(t, 2H); 3.95(t, 2H); 4.87(t, 2H); 7.05(d, 1H); 7.78(d, 1H); 8.04(dd, 1H); 8.62(d, 1H); 9.10(s, 2H).

UV (H$_2$O): $\lambda_{max}$ (E$_{1\%}$)=230 nm (650 cm); 240 nm (555 cm); 370 nm (244 cm); 591 nm(342 cm).

EXAMPLE 36

Following the procedure of Example 35, the following compounds are prepared as the trihydrochloride salt starting from the appropriate N-tert-butoxycarbonyl derivatives:

2-[2-[(2-hydroxyethyl)amino]-ethyl]-5-[[2-(amino)ethyl] amino]isoquino[8,7,6-cd]indazole-6(2H)-one;

m.p.>250° C.

$^1$H-NMR (D$_2$O): 3.31(t, 2H); 3.34(t, 2H); 3.80(t, 2H); 3.88(t, 2H); 3.95(t, 2H); 4.93(t, 2H), 7.10(d, 1H); 7.88(d, 1H); 8.25(dd, 1H); 8.69(d, 1H); 9.28(s, 1H).

UV (H$_2$O): $\lambda_{max}$(E$_{1\%}$)=236 nm (451 cm); 381 nm (187 cm); 508 nm (210 cm);

2-[2-(amino)ethyl]-5-[[2-[(2-hydroxyethyl)amino]ethyl] amino]isoquino]8,7,6-cd]indazole-6(2H)-one;

$^1$H-NMR (D$_2$O): 3.28(t, 2H); 3.31(m, 4H); 3.85(m, 4H); 4.90(t, 2H); 7.03(d, 1H); 7.70(d, 1H); 8.35(dd, 1H); 8.72(d, 1H); 9.77(s, 1H).

UV (H$_2$O): $\lambda_{max}$(E$_{1\%}$)=236 nm (485); 382 nm (198 cm); 507 nm (228 cm).

2-[2-(amino)ethyl)]-5-[[(2-(dimethylamino) ethyl]amino] isoquino[8,7,6-cd]indazole-6(2H)-one m.p.: 224° C. (dec.).

$^1$H-NMR (D$_2$O): 3.00(s, 6H); 3.60(t, 2H); 3.70(t, 2H); 4.07(t, 2H); 4.93(t, 2H); 7.20(d, 1H); 7.95(d, 1H); 8.43(dd, 1H); 8.77(d, 1H); 9.43(s, 1H).

UV (HCl 0.1N): $\lambda_{max}$ (E$_{1\%}$)=236 nm (485); 382 nm (205 cm); 507 nm (232 cm).

2-[2-(amino)ethyl]-5-[[2-(amino)ethyl]isoquino [5,6,7-cd] indazole-6(2H)-one m.p.: >260° C.

$^1$H-NMR (D$_2$O): 3.42(t, 2H); 3.75(t, 2H); 4.00(t, 2H); 5.05(t, 2H); 7.32(d, 1H); 8.09(d, 1H); 8.62(d, 1H); 8.87(d, 1H); 9.55(s, 1H)

UV (HCl 0.1N): $\lambda_{max}$ (E$_{1\%}$)=245 nm(622 cm); 275 nm (181 cm); 351 nm(258 cm); 472 nm (327 cm), 494 nm (353 cm).

2-[2-[(2-hydroxyethyl)amino]ethyl]-5-[[2-(methylamino)ethyl]amino]isoquino[8,7,6-cd ]indazole-6(2H)-one;

UV (HCl 0.01N): $\lambda_{max}$ (E$_{1\%}$)=236 nm (495 cm); 381 nm (198 cm); 501 nm (223 cm);

2-[2-[(2-hydroxyethyl)amino]ethyl]-5-[[2-[(2-hydroxyethyl)amino]ethyl]amino]isoquino[8,7,6-cd]indazole-6(2H)-one;

$^1$H-NMR (D$_2$O):3.32(m, 4H); 3.51(t, 2H); 3.87(m, 6H); 4.02(t, 2H); 4.96(t, 2H); 7.12(d, 1H); 7.91(d, 1H); 8.35(d, 1H); 8.74(d, 1H); 9.33(s, 1H).

UV (H$_2$O): $\lambda_{max}$ (E$_{1\%}$)=230 nm (489); 240 nm (424); 370 nm (185 cm); 492 nm (258); 470 nm (251 cm);

2-[2-(amino)ethyl)]-5-[[2 -(methylamino)ethyl]amino]isoquino[8,7,6-cd]indazole -6(2H)-one;

$^1$H-NMR (D$_2$O): 2.80 (s, 3H); 3.45 (t, 2H); 3.70 (t, 2H); 4.0 (t, 2H); 4.89 (t, 2H); 7.11 (d, 1H); 7.89 (d, 1H); 8.38 (d, 1H); 8.76 (d, 1H); 9.35 (s, 1H);

UV (H$_2$O): $\lambda_{max}$ (E$_{1\%}$)=230 nm (534 cm); 240 nm (458 cm); 368 nm (198 cm); 470 nm (274 cm); 491 nm (280 cm);

2-[2-(hydroxy)ethyl)]-5-[[2-(amino)ethyl]amino]isoquino [8,7,6-cd]indazole-6(2H)-one (dihydrochloride salt);

2-[2-(amino)ethyl]-5-[[2-[N-bis(2-hydroxyethyl)amino] ethyl]amino]isoquino[8,7,6-cd]indazole-6(2H)-one;

2-[2-(amino)ethyl]-5-[[2-(diethylamino)ethyl]amino]isoquino[8,7,6-cd]indazole-6(2H)-one;

2-[2-(amino)ethyl]-5-[[2-(4'-morpholinyl)ethyl]amino]isoquino[8,7,6-cd]indazole-6(2H)-one;

2-[2-(amino)ethyl)]-5-[[2-[(2-hydroxyethyl)amino]ethyl] amino]isoquino[5,6,7-cd]indazole-6(2H)-one;

2-[2-(amino)ethyl)]-5-[[2-(dimethylamino)ethyl]amino]isoquino[5,6,7-cd]indazole-6(2H)-one;

2-[2-aminoethyl]-5-[[2-(dimethylamino)ethyl]amino]isoquino[8,7,6-cd]indazole-6(2H)-one-9-oxide;

2-[2-aminoethyl]-5-[(2-aminoethyl)amino]isoquino[8,7,6-cd]indazole-6(2H)-one-9-oxide;

2-[2-aminoethyl]-5-[[2-(dimethylamino)ethyl ]amino]isoquino[8,7,6-cd]indazole-6(2H)-one-9-oxide;

2-[2-aminoethyl]-5-[[2-(dimethylamino) ethyl]amino]isoquino[5,6,7-cd]indazole-6(2H)-one-8-oxide 2-[2-(dimethylamino)ethyl]-5-[[2-(amino)ethyl]amino] quino[5,6,7-cd]indazole-6(2H)-one;

2-[2-(dimethylamino)ethyl]-5-[[2-(amino)ethyl]amino] quino[8,7,6-cd]indazole-6(2H)-one.

EXAMPLE 37

Removal of the p-methoxybenzyl protective group: 5-[ [2-(dimethylamino)ethyl]amino]-2-methyl-10-hydroxyisoquino[5,6,7-cd]indazole-6(2H)-one.

To a mixture of 10-(p-methoxybenzyloxy)-5-[[2-(dimethylamino)ethyl]amino]-2-methylisoquino[5,6,7-cd]indazole-6(2H)-one of Example 28(0.010 g) in dichloromethane (1 mL) trifluoroacetic acid is added upon which all solid is in solution. After 1 h the mixture is diluted with dichloromethane (3 mL) and a saturated solution of sodium bicarbonate (5 mL) is added. The dichloromethane layer is separated and the aqueous phase extracted with dichloromethane (3×8 mL). The extracts are dried over magnesium sulfate and removed under a slow nitrogen stream. The material is placed under vacuum for 2 h to give 5-[[2-(dimethylamino)ethyl]amino]-2-methyl-10-hydroxyisoquino[5,6,7-cd]indazole-6(2H)-one as an amorphous solid.

$^1$H NMR (CDCl$_3$)δ9.35(s, 1H), 9.15(t, 1H), 8.60(s, 1H), 7.61(d, 1H), 6.95(d, 1H), 4.25(s, 3H), 3.55(q, 2H), 2.75(t, 2H), 2.38(s, 6H).

EXAMPLE 38

Using the procedure of Example 37 the following compounds are prepared starting from the appropriate 4-(p-methoxybenzyloxy)-derivatives of Example 29:

2-[2-(dimethylamino)ethyl]-5-[[2-(dimethylamino)ethyl]amino]-10-hydroxyisoquino [5,6,7-cd]indazole-6(2H)-one;

2-[2-(dimethylamino)ethyl]-5-[[2-(amino)ethyl]amino]-10-hydroxyisoquino[5,6,7-cd]indazole-6(2H)-one;

2-[2-(amino)ethyl]-5-[[2-(amino)ethyl]amino]-10-hydroxy-isoquino[5,6,7-cd]indazole-6(2H)-one.

EXAMPLE 39

2-[2-(dimethylamino)ethyl]-5-[[2-(amino)ethyl]amino]isoquino[8,7,6-cd]indazole-6(2H)-one dimaleate A solution of maleic acid (0.030 g) in absolute ethanol (0.4 mL) is added drop-wise into a stirred solution of 2-[2-(dimethylamino) ethyl]-5-[[2-(amino) ethyl]amino]isoquino[8,7,6-cd]indazole-6(2H)-one of Example 22 (0.030 g) in absolute ethanol(1.5 ml) held at 50° C. After the addition is complete the reaction mixture is maintained at 50° C. for 3 minutes and then allowed to cool to room temperature. After one hour the red-amaranth crystalline material which separated is filtered, washed with ethanol and dried under vacuum at 40° C. to give 2-[2-(dimethylamino)ethyl]-5-[[2-(amino)ethyl]amino]isoquino[8,7,6-cd]indazole-6(2H)-one dimaleate (0.029 g).

m.p.: 175°–175.5° C.

$^1$H-NMR (D$_2$O): 3.00 (s, 6H); 3.40 (t, 2H); 3.80 (t, 2H); 3.93 (t, 2H); 4.90 (t, 2H); 6.00 (s, 4H); 7.00 (d, 1H); 7.70 (d, 1H); 7.80 (d, 1H); 8.55 (d, 1H); 9.00 (s, 1H).

UV (HCl 0.1N): $\lambda_{max}$ (E$_{1\%}$)=126 nm (436 cm); 382 nm (169 cm); 507 nm (190 cm).

EXAMPLE 40

Following the procedure of Example 39, the following maleate salts are prepared by salification of the appropriate isoquinoindazole-6(2H)-ones with maleic acid:

2-[2-(dimethylamino)ethyl)]-5-[[2-(dimethylamino)ethyl]amino]isoquino[8,7,6-cd]indazole-6(2H)-one dimaleate m.p.: 189°–191° C.

$^1$H-NMR (DMSO-d$_6$): 2.88 (s, 12H); 3.37 (t, 2H); 3.70 (t, 2H); 3.95 (q, 2H); 5.01 (t, 2H); 6.00 (s, 4H); 7.38 (d, 1H); 8.20 (dd, 1H); 8.85 (d, 1H); 9.20 (br.t., 1H); 9.55 (s, 1H).

UV (H$_2$O): $\lambda_{max}$ (E$_{1\%}$)=368 nm (154 cm); 469 nm (206 cm); 490 nm (211 cm).

2-[2-(dimethylamino)ethyl)]-5-[[2-(dimethylamino)ethyl]amino]isoquino[5,6,7-cd]indazole-6(2H)-one dimaleate m.p.: 142°–146° C.

$^1$H-NMR (D$_2$O): 3.00 (s, 6H); 3.05 (s, 6H); 3.60 (t, 2H); 3.92 (t, 2H); 4.08 (t, 2H); 5.07 (t, 2H); 6.15 (s, 4H); 7.20 (d, 1H); 7.95 (d, 1H); 8.20 (d, 1H); 8.75 (d, 1H); 9.30 (s, 1H).

UV (H$_2$O): $\lambda_{max}$ (E$_{1\%}$)=292 nm (108 cm); 352 nm (133 cm); 476 nm (215 cm).

2-[2-(dimethylamino)ethyl)]-5-[[2-[(2-hydroxyethyl)amino]ethyl]amino]isoquino [8,7,6-cd]indazole-6(2H)-one dimaleate m.p.: 145° C.

$^1$H-NMR (D$_2$O): 3.05 (s, 6H); 3.30 (m, 2H); 3.54 (t, 2H); 3.88 (m, 4H); 4.03 (t, 2H); 4.96 (t, 2H); 6.00 (s, 4H); 7.00 (d, 1H); 7.70 (d, 1H); 7.83 (dd, 1H); 8.57 (d, 1H); 9.05 (s, 1H)

UV (H$_2$O): $\lambda_{max}$ (E$_{1\%}$)=368 nm (1057 cm); 491 nm (210 cm).

2-[2-(dimethylamino)ethyl)]-5-[[3-(dimethylamino)propyl]amino]isoquino[8,7,6-cd]indazole-6(2H)-one dimaleate m.p. 139°–141° C.

$^1$H-NMR (D$_2$O): 2.24 (m, 2H); 2.94 (s, 6H); 3.00 (s, 6H); 3.35 (t, 2H); 3.67 (t, 2H); 3.83 (t, 2H); 4.87, t, 2H); 6.14 (s, 4H); 6.99 (d, 1H); 7.73 (d, 1H); 7.91 (d, 1H); 8.63 (d, 1H); 9.10 (s, 1H);

UV (H$_2$O): $\lambda_{max}$ (E$_{1\%}$)=366 nm (145 cm); 474 nm (201 cm); 499 nm (211 cm).

2-[2-(dimethylamino)ethyl)]-5-[[2-(4'-morpholinyl)ethyl]amino]isoquino[8,7,6-cd]indazole-6(2H)-one dimaleate m.p. 180°–182° C.

$^1$H-NMR (D$_2$O): 3.01 (s, 6H); 3.49 (m, 4H); 3.57 (t, 2H); 3.81 (t, 2H); 4.01 (m, 6H); 4.89 (t, 2H); 6.01 (s, 4H); 7.00 (d, 1H); 7.74 (d, 1H); 7.88 (d, 1H); 8.60 (d, 1H); 9.05 (s, 1H)

UV (H$_2$O): $\lambda_{max}$ (E$_{1\%}$)=367 nm (116 cm); 477 nm (173 cm); 500 nm (173 cm).

2-[2-(dimethylamino)ethyl)]-5-[[2-(diethylamino)ethyl]amino]isoquino[8,7,6-cd]indazole-6(2H)-one dimaleate m.p. 144°–145° C.

$^1$H-NMR (D$_2$O): 1.31 (t, 6H); 3.00 (s, 6H); 3.35 (q, 4H); 3.55 (t, 2H); 3.84 (t, 2H); 4.01 (t, 2H); 4.93 (t, 2H); 6.07 (s, 4H); 7.03 (d, 1H); 7.78 (d, 1H); 7.95 (d, 1H); 8.63 (d, 1H); 9.11 (s, 1H).

UV (H$_2$O): $\lambda_{max}$ (E$_{1\%}$)=368 nm (116 cm); 471 nm (168 cm); 491 nm (174 cm)

2-[2-(dimethylamino)ethyl)]-5-[[2-(methylamino)ethyl]amino]isoquino[8,7,6-cd]indazole-6(2H)-one dimaleate m.p. 166°–167° C.

$^1$H-NMR (D$_2$O): 2.80 (s, 3H); 3.04 (s, 6H); 3.44 (t, 2H); 3.82 (t, 2H); 3.95 (t, 2H); 4.90 (t, 2H); 5.99 (s, 4H); 6.98 (d, 1H); 7.74 (d, 1H); 7.89 (d, 1H); 8.59 (d, 1H); 9.04 (s, 1H);

UV (H$_2$O): $\lambda_{max}$ (E$_{1\%}$)=367 cm (150 cm); 470 nm (198 cm); 491 nm (203 cm).

2-[2-(dimethylamino)ethyl)]-5-[[3-(amino)propyl]amino]isoquino[8,7,6-cd]indazole-6(2H)-one dimaleate m.p. 175° C.

$^1$H-NMR (D$_2$O): 2.15 (m, 2H); 3.00 (s, 6H); 3.20 (t, 2H); 3.62 (t, 2H); 3.81 (t, 2H); 4.85 (t, 2H; D$_2$O overlapping); 6.09 (s, 4H); 6.94 (d, 1H); 7.68 (d, 1H); 7.82 (d, 1H); 8.59 (d, 1H); 9.02 (s, 1H).

UV (H$_2$O): $\lambda_{max}$ (E$_{1\%}$): 368 nm (156 cm); 475 nm (221 cm); 500 nm (234 cm)

2-[2-(hydroxy)ethyl)]-5-[[2-(dimethylamino)ethyl]amino]isoquino[8,7,6-cd]indazole-6(2H)-one dimaleate m.p. 105°–107° C.

$^1$H-NMR (D$_2$O): 3.00 (s, 6H); 3.48 (t, 2H); 3.82 (t, 2H); 4.0 (t, 2H); 4.32 (t, 2H); 6.09 (s, 2H); 6.62 (d, 1H); 7.28 (d, 1H); 7.44 (d, 1H); 8.20 (d, 1H); 8.42 (s, 1H).

2-[2-[(2-hydroxyethyl)amino]ethyl]-5-[[2-[(2-hydroxyethyl)amino]ethyl]amino]isoquino[5,6,7-cd]indazole-6(2H)-one m.p. 123°–126° C. (dec);

2-methyl-5-[[2-(dimethylamino)ethyl]amino]isoquino[8,7,6-cd]indazole-6(2H)-one-9-oxide maleate;

2-[2-(dimethylamino)ethyl]-5-[[2-(dimethylamino)ethyl]amino]isoquino[8,7,6-cd]indazole-6(2H)-one-9-oxide dimaleate;

2-[2-(dimethylamino)ethyl]-5-[[2-(dimethylamino)ethyl]amino]isoquino[5,6,7-cd]indazole-6(2H)-one-8-oxide dimaleate;

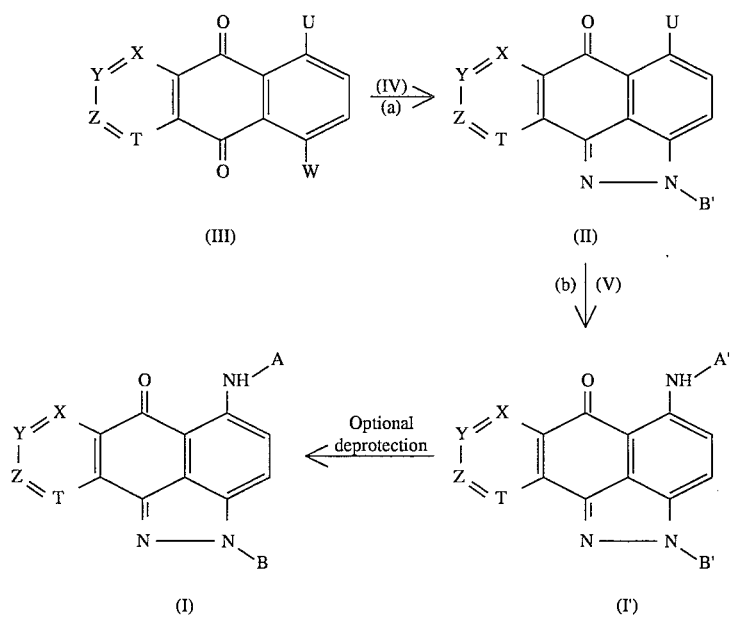

Scheme 1

Scheme 2
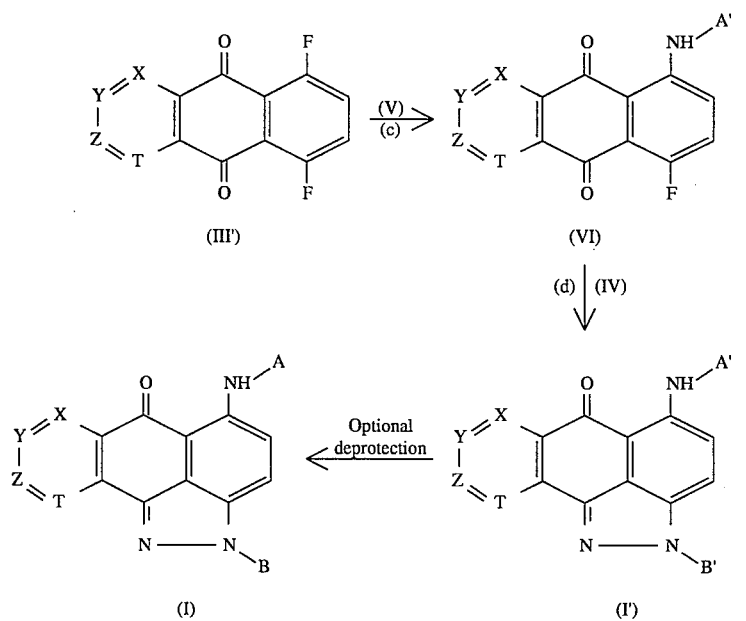
Scheme 3
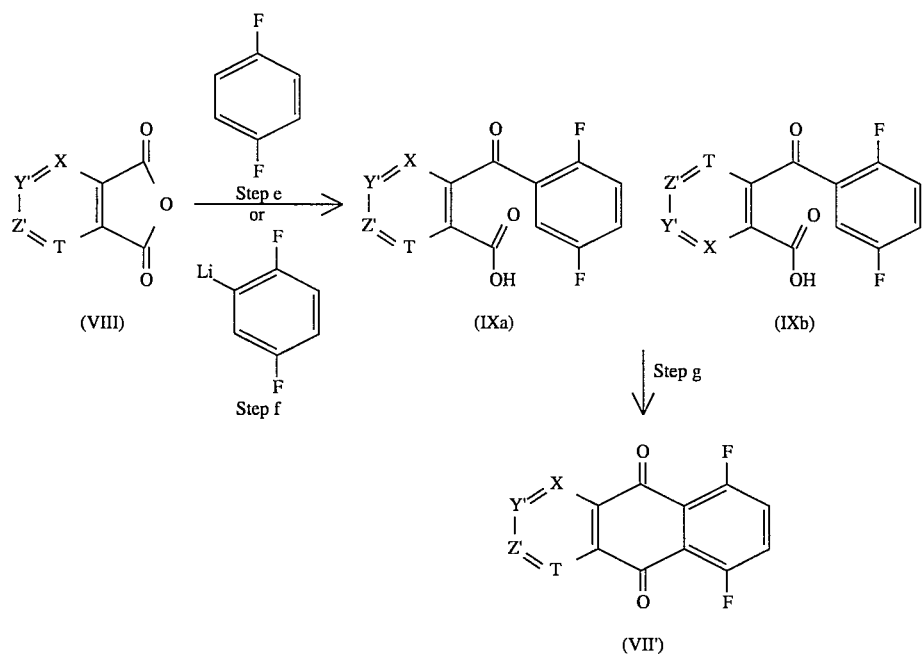

Scheme 4
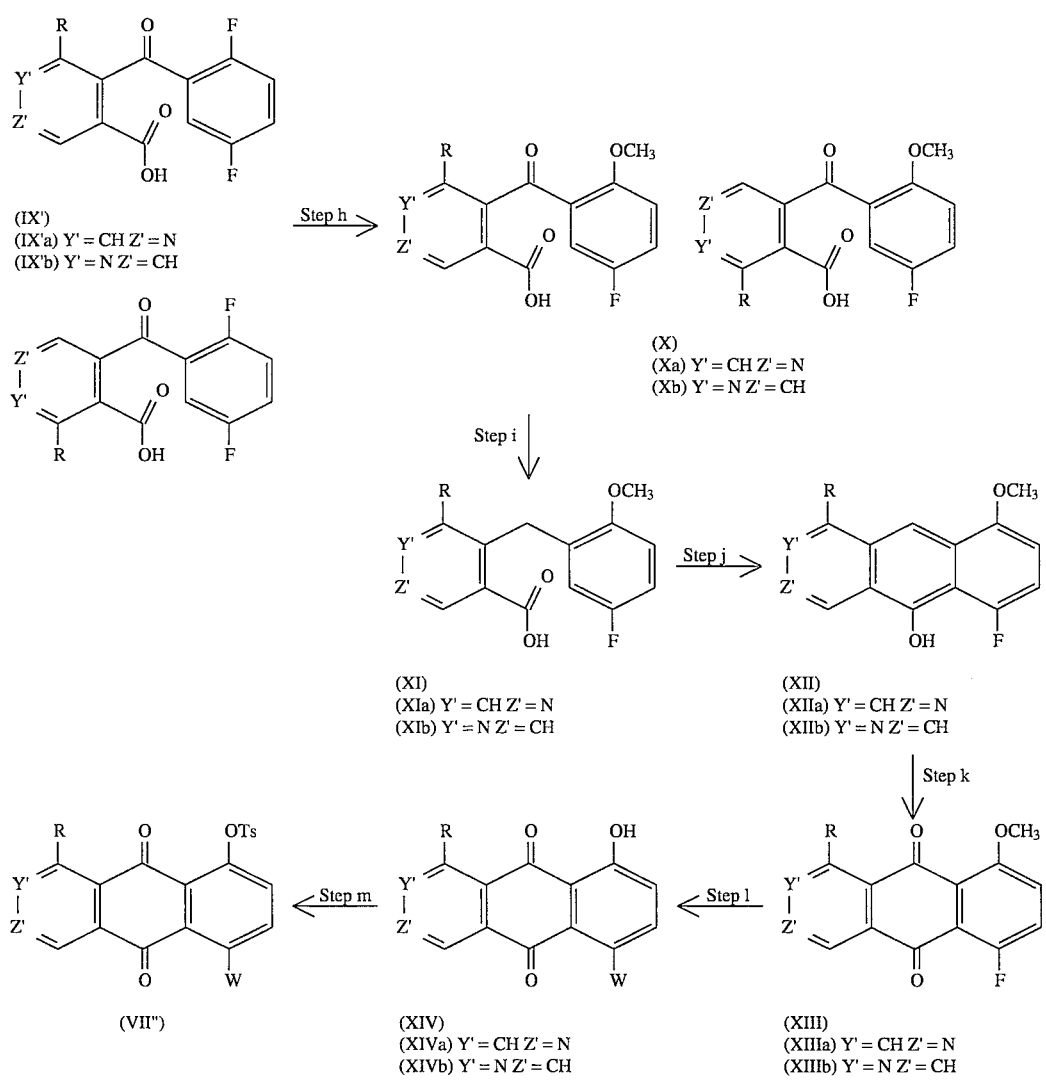

Scheme 5
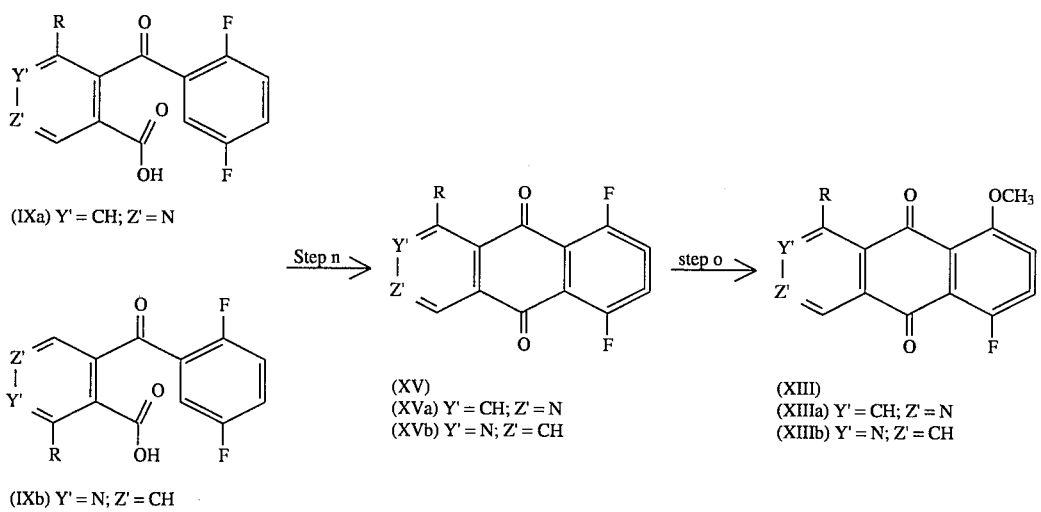
Scheme 6
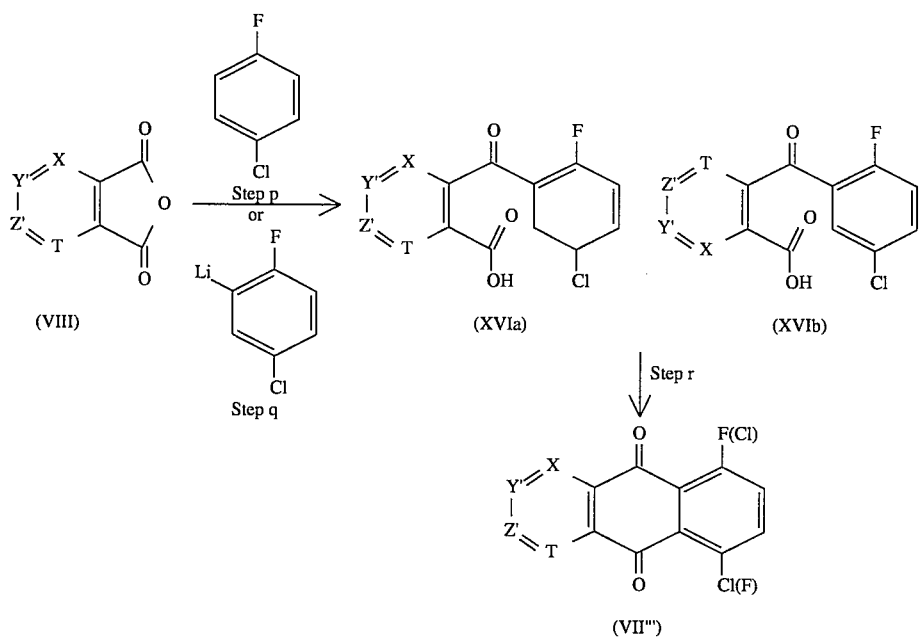

Scheme 7
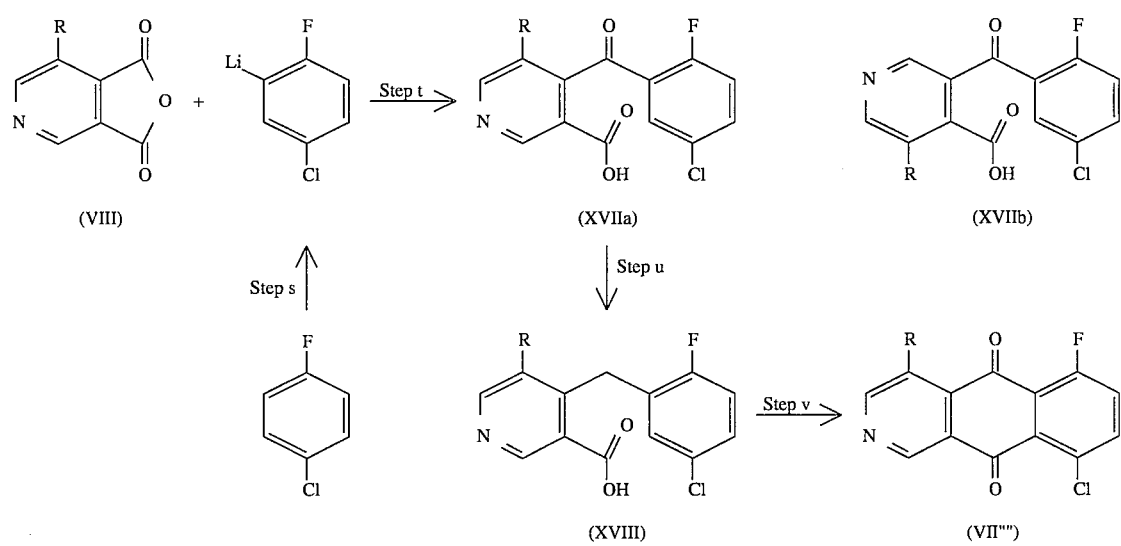
Scheme 8
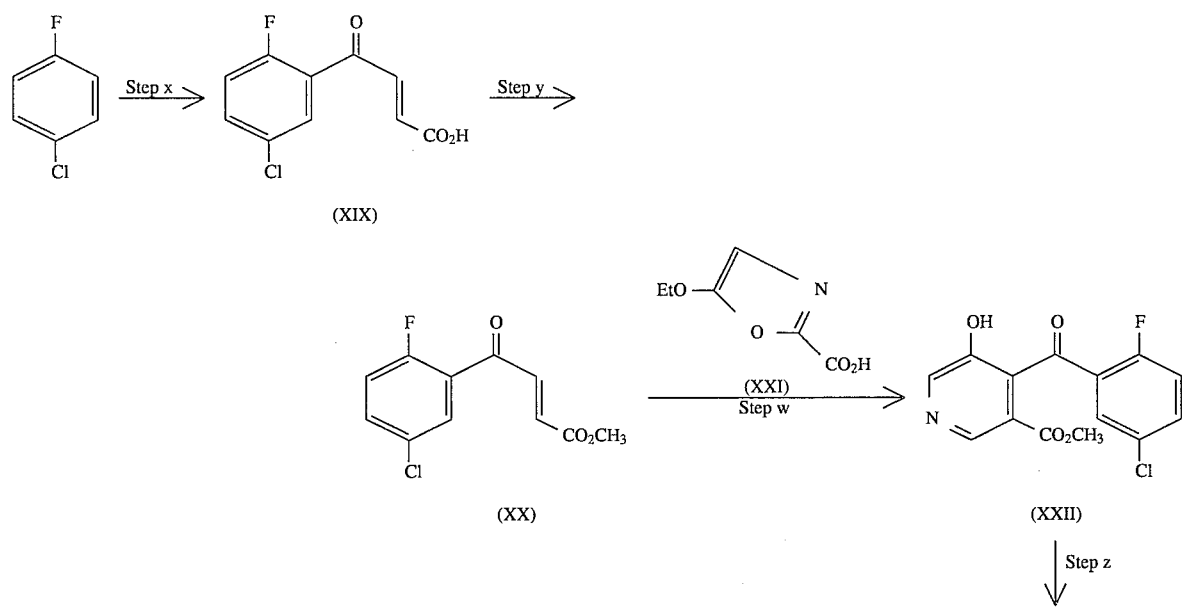

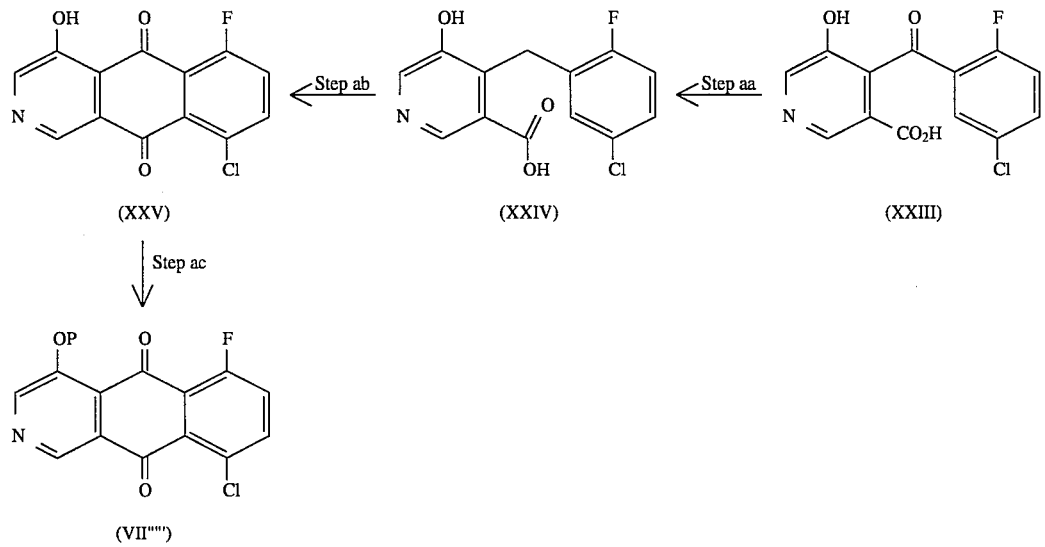

We claim:

1. A compound according to formula (I)

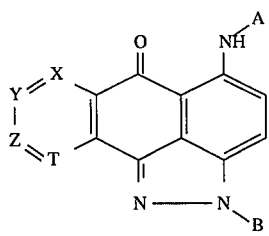

wherein:

Z is NO, X is C, Y is C and T is C;

P is selected from the group consisting of hydrogen, methyl, benzyl, 4-methoxybenzyl;

A and B are the same or different and are selected from the group consisting of $C_1$–$C_{10}$ alkyl; $C_2$–$C_{10}$ alkyl having one or two substituents selected from the group consisting of $OR_1$ and —$NR_2R_3$; $C_2$–$C_{10}$ alkyl interrupted by one or two oxygen atoms or by one —$NR_4$— group, and said $C_2$–$C_{10}$ alkyl is optionally substituted by one or two hydroxy (OH) or —$NR_2R_3$ groups;

$R_1$ is selected from the group consisting of hydrogen, $C_1$–$C_6$ alkyl, —$S(O_2)R_5$, $C_2$–$C_6$ alkyl optionally substituted by —$NR_2R_3$;

$R_2$ and $R_3$ may be the same or different and are selected from the group consisting of hydrogen, $C_1$–$C_{10}$ alkyl, $C_2$–$C_{10}$ alkyl substituted with one or two hydroxy (OH) groups, or $R_2$ and $R_3$ taken together with the nitrogen atom to which they are bound form an N-morpholinyl group;

$R_4$ is selected from the group consisting of hydrogen, $C_1$–$C_{10}$ alkyl, $C_2$–$C_{10}$ hydroxyalkyl, $C_2$–$C_{10}$ alkyl substituted with —$NR_2R_3$;

$R_5$ is selected from the group consisting of $C_1$–$C_{10}$ alkyl, phenyl, phenylalkyl, as free bases and their salts with pharmaceutically acceptable acids.

2. A pharmaceutical composition suitable for the treatment of tumors in a patient comprising a compound according to claim 1 and a pharmaceutically acceptable diluent or excipient.

3. A method of treatment of tumors susceptible to azanthrapyrazole treatment in a mammal requiring such treatment comprising administering to the mammal an effective anti-tumor amount of a compound according to claim 1.

4. The compound of claim 1 wherein Z=NO, X=C, Y=C and T=C.

5. A compound of claim 1 selected from the group consisting of 2-methyl-5-[[2-(dimethylamino)ethyl]amino]isoquino[8, 7, 6-cd]indazole-6(2H)-one-9-oxide;

2-[2-aminoethyl]-5-[[3-(dimethylamino)propyl]amino] isoquino[8, 7, 6-cd]indazole-6(2H)-one-9-oxide;

2-[2-(dimethylamino)ethyl]-5-[[2-(dimethylamino)ethyl] amino]isoquino[8, 7, 6-cd]indazole-6(2H)-one-9-oxide;

2-[2-aminoethyl]-5-[(2-aminoethyl)amino]isoquino[8, 7, 6-cd]indazole-6(2H)-one-9-oxide; and 2-[2-aminoethyl]-5-[[2-(dimethylamino)ethyl]amino]isoquino[8, 7, 6-cd]indazole-6(2H)-one-9-oxide, as free bases and their salts with pharmaceutically acceptable acids.

6. The compound of claim 5 which is

2-[2-(dimethylamino)ethyl]-5-[[2-(dimethylamino)ethyl] amino]isoquino[8, 7, 6-cd]indazole-6(2H)-one-9-oxide.

* * * * *

UNITED STATES PATENT AND TRADEMARK OFFICE
CERTIFICATE OF CORRECTION

PATENT NO. : 5,596,097
DATED : January 21, 1997
INVENTOR(S) : Krapcho et al.

It is certified that error appears in the above-indentified patent and that said Letters Patent is hereby corrected as shown below:

column 69, lines 39-40, please delete -- P is selected from the group consisting of hydrogen, methyl, benzyl, 4-methoxybenzyl; --

Signed and Sealed this

Twenty-fourth Day of June, 1997

Attest:

BRUCE LEHMAN

*Attesting Officer*  *Commissioner of Patents and Trademarks*